US010071108B2

(12) United States Patent
Andre et al.

(10) Patent No.: US 10,071,108 B2
(45) Date of Patent: *Sep. 11, 2018

(54) METHODS AND PHARMACEUTICAL COMPOSITIONS FOR THE TREATMENT OF HEPATITIS B VIRUS INFECTION

(71) Applicants: INSERM (INSTITUT NATIONAL DE LA SANTÉ ET DE LA RECHERCHE MEDICALE), Paris (FR); UNIVERSITÉ CLAUDE BERNARD—LYON 1, Villeurbanne (FR); ENS—ECOLE NORMALE SUPERIEURE DE LYON, Lyons (FR); CENTRE NATIONAL DE LA RECHERCHE SCIENTIFIQUE (CNRS), Paris (FR); EDELRIS, Lyons (FR); POXEL, Lyons (FR)

(72) Inventors: Patrice Andre, Lyons (FR); Vincent Lotteau, Lyons (FR); Pauline Radreau, Lyons (FR); Marine Gilardone, Millery (FR); Amaury Patin, Lausanne (CH); Didier Roche, Ecully (FR); Daniel Cravo, Montesson (FR); Sophie Hallakou-Bozec, Antony (FR)

(73) Assignees: INSERM (INSTITUT NATIONAL DE LA SANTE ET DE LA RECHERCHE MEDICALE), Paris (FR); UNIVERSITE CLAUDE BERNARD—LYON 1, Villeurbann (FR); ENS—ECOLE NORMALE SUPÉRIEURE DE LYON, Lyons (FR); CENTRE NATIONAL DE LA RECHERCHE SCIENTIFIQUE (CNRS), Paris (FR); EDELRIS, Lyons (FR); POXEL, Lyons (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/898,944

(22) Filed: Feb. 19, 2018

(65) Prior Publication Data
US 2018/0169115 A1 Jun. 21, 2018

Related U.S. Application Data

(63) Continuation of application No. 14/917,958, filed as application No. PCT/EP2014/069312 on Sep. 10, 2014, now Pat. No. 9,895,380.

(30) Foreign Application Priority Data

Sep. 11, 2013 (EP) .................... 13306245

(51) Int. Cl.
*A61K 31/575* (2006.01)
*A61K 31/42* (2006.01)
*A61K 31/4525* (2006.01)
*A61K 31/496* (2006.01)
*A61K 31/513* (2006.01)
*A61K 31/522* (2006.01)
*A61K 31/55* (2006.01)
*A61K 31/551* (2006.01)
*A61K 31/675* (2006.01)
*A61K 31/7072* (2006.01)
*A61K 45/06* (2006.01)
*A61K 38/21* (2006.01)

(52) U.S. Cl.
CPC ............ *A61K 31/575* (2013.01); *A61K 31/42* (2013.01); *A61K 31/4525* (2013.01); *A61K 31/496* (2013.01); *A61K 31/513* (2013.01); *A61K 31/522* (2013.01); *A61K 31/55* (2013.01); *A61K 31/551* (2013.01); *A61K 31/675* (2013.01); *A61K 31/7072* (2013.01); *A61K 38/212* (2013.01); *A61K 45/06* (2013.01)

(58) Field of Classification Search
CPC .. A61K 31/575; A61K 31/42; A61K 31/4525; A61K 31/496; A61K 31/513; A61K 31/522; A61K 31/55; A61K 31/551; A61K 31/675; A61K 31/7072; A61K 38/212; A61K 45/06
USPC ........................................................ 514/182
See application file for complete search history.

(56) References Cited

U.S. PATENT DOCUMENTS 7,138,390 B2    11/2006  Pellicciari

FOREIGN PATENT DOCUMENTS

| DE | 10 2010 012226 | 9/2011 |
| EP | 0 692 487 | 1/1996 |
| WO | WO 2006/044391 | 4/2006 |
| WO | WO 2008/002573 | 1/2008 |
| WO | WO 2010/069604 | 6/2010 |

OTHER PUBLICATIONS

Mencarelli, A., et al., "The Bile Acid Sensor Farnesoid X Receptor Is a Modulator of Liver Immunity in a Rodent Model of Acute Hepatitis," *The Journal of Immunology*, Nov. 15, 2009, vol. 183, No. 10, pp. 6657-6666.

(Continued)

*Primary Examiner* — Yevgeny Valenrod
(74) *Attorney, Agent, or Firm* — Saliwanchik, Lloyd & Eisenschenk

(57) ABSTRACT

The present invention relates to methods and pharmaceutical compositions for the treatment of hepatitis B virus infection. In particular, the present invention relates to farnesoid X receptor (FXR) agonists for use in a method for the treatment of hepatitis B virus infection in a subject in need thereof.

16 Claims, 10 Drawing Sheets

(56) References Cited

OTHER PUBLICATIONS

Ramière, C., et al., "Transactivation of the Hepatitis B Virus Core Promoter by the Nuclear Receptor FXRα," *Journal of Virology*, Nov. 2008, vol. 82, No. 21, pp. 10832-10840.
Written Opinion in International Application No. PCT/EP2014/069312, dated Jan. 8, 2015, pp. 1-8.
Liu, Y. et al. "Hepatoprotection by the farnesoid X receptor agonist GW4064 in rat models of intra- and extrahepatic cholestasis" *The Journal of Clinical Investigation*, Dec. 2003, pp. 1678-1687. vol. 112, No. 11.
Makishima, M. et al. "Identification of a Nuclear Receptor for Bile Acids" *Science*, May 21, 1999, pp. 1362-1365, vol. 284.
Parks, D. J. et al. "Bile Acids: Natural Ligands for an Orphan Nuclear Receptor" *Science*, May 21, 1999, pp. 1365-1368, vol. 284.
Wang, H. et al. "Endogenous Bile Acids Are Ligands for the Nuclear Receptor FXR/BAR" *Molecular Cell*, May 1999, pp. 543-553, vol. 3.
Chiang, J. Y. L. et al. "Farnesoid X Receptor Responds to Bile Acids and Represses Cholesterol 7α-Hydroxylase Gene (CYP7A1) Transcription" *The Journal of Biological Chemistry*, Apr. 14, 2000, pp. 10918-10924, vol. 275, No. 15.

METHODS AND PHARMACEUTICAL COMPOSITIONS FOR THE TREATMENT OF HEPATITIS B VIRUS INFECTION

CROSS-REFERENCE TO RELATED APPLICATIONS

This application is a continuation of U.S. application Ser. No. 14/917,958, filed Mar. 10, 2016, now U.S. Pat. No. 9,895,380, which is the U.S. national stage application of International Patent Application No. PCT/EP2014/069312, filed Sep. 10, 2014.

FIELD OF THE INVENTION

The present invention relates to methods and pharmaceutical compositions for the treatment of hepatitis B virus infection.

BACKGROUND OF THE INVENTION

HBV is an enveloped virus containing a 3.2-kb partially double stranded DNA genome with four open reading frames. These open reading frames encode the reverse transcriptase, precore, and core proteins; three surface antigen proteins (pre-S1, pre-S2, and S); and the X protein. Regulation of HBV transcription is under the control of four promoters (the core, pre-S1, pre-S2/S, and X promoters) and two enhancer regions (EN1 and EN2). Eight genotypes of HBV, designated A to H, have been determined, with some geographical distribution. The virus is non-cytopathic, with virus-specific cellular immunity being the main determinant for the outcome of exposure to HBV—acute infection with resolution of liver diseases within 6 months, or chronic HBV infection that is frequently associated with progressive liver injury. Detection of HBsAg in the serum, by conventional diagnostic immunoassays, is the key diagnostic marker for infection with HBV and persistent detection of HBsAg in serum for more than 6 months is the hallmark of chronic HBV infection. The best marker for clinically significant HBV replication is the level of HBV DNA in serum, as detected by sensitive polymerase chain reaction (PCR)-based assay. Worldwide more than 350 million people are chronically infected with HBV and are thus at increased risk of developing serious liver disease, such as chronic hepatitis, cirrhosis, liver failure and hepatocellular carcinoma (HCC).

The primary goal of treatment for chronic hepatitis B (CHB) is to permanently suppress HBV replication and prevent or improve liver disease. Seven drugs are currently available for treatment of CHB infection: conventional interferon, pegylated interferon and direct antiviral agents. The direct antivirals (nucleos/tide analogues) belong to three classes: L-nucleosides (lamivudine, telbivudine and emtricitabine); deoxyguanosine analogue (entecavir) and nucleoside phosphonates (adefovir and tenofovir), which directly interfere with HBV DNA replication, primarily as chain terminators. The key limitations for interferon treatment are major side effects, low rate of HBV DNA suppression and low rate of ALT normalization. The key limitations of the treatment with direct antivirals are development of resistance; rebound of HBV replication after stopping therapy, requiring prolonged, lifelong therapy; and very low rate of HBsAg clearance, increasing the risk of adverse events with prolonged, lifelong therapy. Importantly, current direct antivirals repress the reverse transcription of the pregenomic viral RNA into the genomic DNA. They thus act downstream to the formation of the cccDNA that is formed after virus entry into hepatocytes. cccDNA resides in the cell nucleus as additional minichromosomes that are transcribed into viral mRNAs and transmitted to daughter cells when hepatocytes divide. Current direct antivirals have no or very little effect on the HBV cccDNA reservoir and the expression of the viral genes. Thus, the currently available treatments are suboptimal and may be associated with severe side effects. Accordingly there is a need for better therapies to meet the treatment goals in HBV infection, in particular CHB infection. Indirectly acting antivirals (IAD), besides interferons, arise as a very promising alternative class of antivirals. Small molecules blocking the interaction of a cellular protein with a viral protein have been successfully developed to prevent HIV entry and HCV replication. Viral entry and innate immunity are obvious cellular functions to be screened for the identification of new therapeutic targets. However, unlike HIV and HCV, our knowledge of specific cellular functions used by HBV to replicate in hepatocytes remains very limited and systematic screening for the identification of these essential host factors is necessary to increase the diversity of potential therapeutic targets and molecules. A major goal is therefore to identify these functions for preventing their use and/or perturbation by the virus by safer and broad-spectrum molecules with high barrier to resistance.

Recent data strongly suggest that farnesoid X receptor (FXR), which is a member of the nuclear receptor superfamily, is implicated in the regulation of HBV core promoter activity and that bile acids could play an important role in the natural history of HBV infection (Ramière C, Scholtès C, Diaz O, Icard V, Perrin-Cocon L, Trabaud M A, Lotteau V, André P. Transactivation of the hepatitis B virus core promoter by the nuclear receptor FXRalpha, Journal of Virology, 2008; 82: 10832-10840). Specifically, in the particular cellular model of infection in the Huh-7 cell line with various HBV infection vectors, data suggested that FXRα agonists increase viral replication while antagonists of FXRα may represent a new class of compounds useful for the treatment of HBV infection by inhibiting HBV replication.

SUMMARY OF THE INVENTION

The present invention provides new methods for the treatment of patients with hepatitis B virus infections. In particular, the present invention is defined by the claims.

DETAILED DESCRIPTION OF THE INVENTION

The present invention relates to farnesoid X receptor (FXR) agonists for use in a method for the treatment of hepatitis B virus infection in a subject in need thereof.

As used herein a "Hepatitis B virus infected patient" means a patient being infected with any Hepatitis B virus genotype, e.g., genotype A, B, C, D etc.

According to the invention, the term "subject" or "patient" and "subject in need thereof" or "patient in need thereof" is intended for a human or non-human mammal infected or likely to be infected with a hepatitis B virus. In some embodiments, the subject suffers from a chronic HBV infection.

As used herein, the term "treatment" or "treat" refers to both prophylactic or preventive treatment as well as curative or disease modifying treatment, including treatment of patients at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during HBV therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of a drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at regular intervals, e.g., weekly, monthly, yearly, etc.) or intermittent therapy (e.g., interrupted treatment, intermittent treatment, treatment at relapse, or treatment upon achievement of a particular predetermined criterion (e.g., pain, disease manifestation, etc.)).

The efficacy of the therapy regimen may be monitored using standard protocols. Treatment may be followed by determination of HBV levels in serum and measurement of serum ALT levels. For example, the patients may be assessed for the presence of HBV DNA in their serum. HBV DNA (IU/mL) can be measured at regular intervals during the treatment, e.g., at Day 1 (pre-dose and 4, 8, and 12 hours post-dose) and pre-dose at Day 2, Day 3, Day 8, Day 15, Day 29, and at Week 12, Week 24, Week 36, Week 48, and Week 72 (when applicable), and at follow up. Accordingly, the efficacy of therapy will be monitored using internationally accepted parameters: a) serum HBV DNA levels are monitored using sensitive quantitative PCR-based assays to assess the effect on viral replication; b) in HBeAg-positive patients, HBeAg is monitored along with the corresponding anti-HBe to determine whether HBe-seroconversion has occurred; c) serum levels of ALT and/or AST are monitored to assess impact on liver inflammation and liver cell death; and d) serum HBsAg is monitored, qualitatively and quantitatively along with the corresponding anti-HBs to determine whether HBs-seroconversion has occurred as HBsAg clearance and seroconversion would indicate optimal treatment outcome. Ultimately, even if not of actual clinical routine practice, cccDNA persistence might be assessed by specific PCR to quantify the level of viral minichromosome in liver biopsies.

The term "FXR" refers to the farnesoid X receptor, which is a nuclear receptor that is activated by supraphysiological levels of farnesol (Forman et al., Cell, 1995,81,687-693). FXR is also known as NR1H4, retinoid X receptor-interacting protein 14 (RIP14) and bile acid receptor (BAR). Containing a conserved DNA-binding domain (DBD) and a C-terminal ligand-binding domain (LBD), FXR binds to and becomes activated by a variety of naturally occurring bile acids (BAs), including the primary bile acid chenodeoxycholic acid (CDCA) and its taurine and glycine conjugates (Makishima et al., 1999; Parks et al., 1999; Wang et al., 1999). Upon activation, the FXR-RXR heterodimer binds the promoter region of target genes and regulates the expression of several genes involved in bile acid homeostasis. Hepatic FXR target genes fall into two main groups (Edwards P A. et al. 2002, Kapadia S B. et al. 2005). The first group functions to decrease hepatic bile acid concentrations by increasing export and decreasing their synthesis. The second group of FXR target genes such as the phospholipid transport protein (PLTP) and apolipoproteins modulate lipoprotein levels in the serum and decreases plasma triglyceride concentration. For a more detailed list of FXR-regulated genes, see, e.g., WO 03/016288, pages 22-23. U.S. Pat. No. 6,005,086 discloses the nucleic acid sequence coding for a mammalian FXR protein. The human polypeptide sequences for FXR are deposited in nucleotide and protein databases under accession numbers NM_005123, Q96RI1, NP_005114 AAM53551, AAM53550, and AAK60271.

In this specification, the term "FXR agonist" has its general meaning in the art and refers, in particular, to compounds that function by targeting and selectively binding the farnesoid X receptor (FXR) and which activate FXR by at least 40% above background in the assay described in Maloney et al. (J. Med. Chem. 2000, 43:2971-2974).

In some embodiments, the FXR agonist of the invention is a selective FXR agonist. As used herein, the term "selective FXR agonist" refers to an FXR agonist that exhibits no significant cross-reactivity to one or more, ideally substantially all, of a panel of nuclear receptors consisting of LXRα, LXRβ, PPARα, PPARγ, PPARδ, RXRα, RARγ, VDR, SXR, ERα, ERβ, GR, AR, MR and PR. Methods of determining significant cross-reactivity are described in J. Med. Chem. 2009, 52, 904-907.

FXR agonists are well known to the skilled person. For example, the skilled person may easily identified FXR agonists from the following publications:

Adorini L, Pruzanski M, Shapiro D. Farnesoid X receptor targeting to treat nonalcoholic steatohepatitis. Drug Discov Today. 2012 September; 17(17-18):988-97. doi: 10.1016/j.drudis.2012.05.012. Epub 2012 May 29. Review.

Akwabi-Ameyaw A, Bass J Y, Caldwell R D, Caravella J A, Chen L, Creech K L, Deaton D N, Madauss K P, Marr H B, McFadyen R B, Miller A B, Navas F III, Parks D J, Spearing P K, Todd D, Williams S P, Bruce Wisely G. FXR agonist activity of conformationally constrained analogs of GW 4064. Bioorg Med Chem Lett. 2009 Aug. 15; 19(16):4733-9. doi: 10.1016/j.bmcl.2009.06.062. Epub 2009 Jun. 21.

Akwabi-Ameyaw A, Bass J Y, Caldwell R D, Caravella J A, Chen L, Creech K L, Deaton D N, Jones S A, Kaldor I, Liu Y, Madauss K P, Marr H B, McFadyen R B, Miller A B, Navas F III, Parks D J, Spearing P K, Todd D, Williams S P, Wisely G B. Conformationally constrained farnesoid X receptor (FXR) agonists: Naphthoic acid-based analogs of GW 4064. Bioorg Med Chem Lett. 2008 Aug. 1; 18(15):4339-43. doi: 10.1016/j.bmcl.2008.06.073. Epub 2008 Jun. 28.

Akwabi-Ameyaw A, Caravella J A, Chen L, Creech K L, Deaton D N, Madauss K P, Marr H B, Miller A B, Navas F III, Parks D J, Spearing P K, Todd D, Williams S P, Wisely G B. Conformationally constrained farnesoid X receptor (FXR) agonists: alternative replacements of the stilbene. Bioorg Med Chem Lett. 2011

Oct. 15; 21(20):6154-60. doi: 10.1016/j.bmcl.2011.08.034. Epub 2011 Aug. 11.

Baghdasaryan A, Claudel T, Gumhold J, Silbert D, Adorini L, Roda A, Vecchiotti S, Gonzalez F J, Schoonjans K, Strazzabosco M, Fickert P, Trauner M. Dual farnesoid X receptor/TGR5 agonist INT-767 reduces liver injury in the Mdr2−/− (Abcb4−/−) mouse cholangiopathy model by promoting biliary $HCO^-_3$ output. Hepatology. 2011 October; 54(4):1303-12. doi: 10.1002/hep.24537.

Bass J Y, Caldwell R D, Caravella J A, Chen L, Creech K L, Deaton D N, Madauss K P, Marr H B, McFadyen R B, Miller A B, Parks D J, Todd D, Williams S P, Wisely G B. Substituted isoxazole analogs of farnesoid X receptor (FXR) agonist GW4064. Bioorg Med Chem Lett. 2009 Jun. 1; 19(11):2969-73. doi: 10.1016/j.bmcl.2009.04.047. Epub 2009 Apr. 18.

Bass J Y, Caravella J A, Chen L, Creech K L, Deaton D N, Madauss K P, Marr H B, McFadyen R B, Miller A B, Mills W Y, Navas F 3rd, Parks D J, Smalley T L Jr, Spearing P K, Todd D, Williams S P, Wisely G B. Conformationally constrained farnesoid X receptor (FXR) agonists: heteroaryl replacements of the naphthalene. Bioorg Med Chem Lett. 2011 Feb. 15; 21(4): 1206-13. doi: 10.1016/j.bmcl.2010.12.089. Epub 2010 Dec. 23.

Buijsman et al., Curr. Med. Chem. 2005, 12, 1017.

Chiang P C, Thompson D C, Ghosh S, Heitmeier M R. A formulation-enabled preclinical efficacy assessment of a farnesoid X receptor agonist, GW4064, in hamsters and cynomolgus monkeys. J Pharm Sci. 2011 November; 100(11):4722-33. doi: 10.1002/jps.22664. Epub 2011 Jun. 9.

Crawley, Expert Opin. Ther. Pat. 2010, 20, 1047.

Feng S, Yang M, Zhang Z, Wang Z, Hong D, Richter H, Benson G M, Bleicher K, Grether U, Martin R E, Plancher J M, Kuhn B, Rudolph M G, Chen L. Identification of an N-oxide pyridine GW4064 analog as a potent FXR agonist. Bioorg Med Chem Lett. 2009 May 1; 19(9):2595-8. doi: 10.1016/j.bmcl.2009.03.008. Epub 2009 Mar. 9.

Flatt B, Martin R, Wang T L, Mahaney P, Murphy B, Gu X H, Foster P, Li J, Pircher P, Petrowski M, Schulman I, Westin S, Wrobel J, Yan G, Bischoff E, Daige C, Mohan R. Discovery of XL335 (WAY-362450), a highly potent, selective, and orally active agonist of the farnesoid X receptor (FXR). J Med Chem. 2009 Feb. 26; 52(4):904-7. doi: 10.1021/jm8014124.

Ghebremariam Y T, Yamada K, Lee J C, Johnson C L, Atzler D, Anderssohn M, Agrawal R, Higgins J P, Patterson A J, Boger R H, Cooke J P. FXR agonist INT-747 upregulates DDAH expression and enhances insulin sensitivity in high-salt fed Dahl rats. PLoS One. 2013 Apr. 4; 8(4):e60653. doi: 10.1371/journal.pone.0060653. Print 2013.

Gioiello A, Macchiarulo A, Carotti A, Filipponi P, Costantino G, Rizzo G, Adorini L, Pellicciari R. Extending SAR of bile acids as FXR ligands: discovery of 23-N-(carbocinnamyloxy)-3α,7α-dihydroxy-6α-ethyl-24-nor-5β-cholan-23-amine. Bioorg Med Chem. 2011 Apr. 15; 19(8):2650-8. doi: 10.1016/j.bmc.2011.03.004. Epub 2011 Mar. 10.

Hoekstra M, van der Sluis R J, Li Z, Oosterveer M H, Groen A K, Van Berkel T J. FXR agonist GW4064 increases plasma glucocorticoid levels in C57BL/6 mice. Mol Cell Endocrinol. 2012 Oct. 15; 362(1-2):69-75. doi: 10.1016/j.mce.2012.05.010. Epub 2012 May 27.

Iguchi Y, Kihira K, Nishimaki-Mogami T, Une M. Structure-activity relationship of bile alcohols as human farnesoid X receptor agonist. Steroids. 2010 January; 75(1):95-100. doi: 10.1016/j.steroids.2009.11.002. Epub 2009 Nov. 12.

Lin H R. Triterpenes from *Alisma orientalis* act as farnesoid X receptor agonists. Bioorg Med Chem Lett. 2012 Jul. 15; 22(14):4787-92. doi: 10.1016/j.bmcl.2012.05.057. Epub 2012 May 23.

Lefebvre P, Cariou B, Lien F, Kuipers F, Staels B. Role of bile acids and bile acid receptors in metabolic regulation. Physiol Rev. 2009 January; 89(1):147-91. doi: 10.1152/physrev.00010.2008.

Lundquist J T, Harnish D C, Kim C Y, Mehlmann J F, Unwalla R J, Phipps K M, Crawley M L, Commons T, Green D M, Xu W, Hum W T, Eta J E, Feingold I, Patel V, Evans M J, Lai K, Borges-Marcucci L, Mahaney P E, Wrobel J E. Improvement of physiochemical properties of the tetrahydroazepinoindole series of farnesoid X receptor (FXR) agonists: beneficial modulation of lipids in primates. J Med Chem. 2010 Feb. 25; 53(4): 1774-87. doi: 10.1021/jm901650u.

Ma Y, Huang Y, Yan L, Gao M, Liu D. Synthetic FXR agonist GW4064 prevents diet-induced hepatic steatosis and insulin resistance. Pharm Res. 2013 May; 30(5):1447-57. doi: 10.1007/s11095-013-0986-7. Epub 2013 Feb. 1.

Marinozzi M, Carotti A, Sardella R, Buonerba F, Ianni F, Natalini B, Passeri D, Rizzo G, Pellicciari R. Asymmetric synthesis of the four diastereoisomers of a novel non-steroidal farnesoid X receptor (FXR) agonist: Role of the chirality on the biological activity. Bioorg Med Chem. 2013 Jul. 1; 21(13):3780-9. doi: 10.1016/j.bmc.2013.04.038. Epub 2013 Apr. 23.

Misawa T, Hayashi H, Makishima M, Sugiyama Y, Hashimoto Y. E297G mutated bile salt export pump (BSEP) function enhancers derived from GW4064: structural development study and separation from farnesoid X receptor-agonistic activity. Bioorg Med Chem Lett. 2012 Jun. 15; 22(12):3962-6. doi: 10.1016/j.bmcl.2012.04.099. Epub 2012 Apr. 30.

Mudaliar S, Henry R R, Sanyal A J, Morrow L, Marschall H U, Kipnes M, Adorini L, Sciacca C I, Clopton P, Castelloe E, Dillon P, Pruzanski M, Shapiro D. Efficacy and safety of the farnesoid X receptor agonist obeticholic acid in patients with type 2 diabetes and non-alcoholic fatty liver disease. Gastroenterology. 2013 September; 145(3):574-82. e1. doi: 10.1053/j.gastro.2013.05.042. Epub 2013 May 30.

Richter H G, Benson G M, Bleicher K H, Blum D, Chaput E, Clemann N, Feng S, Gardes C, Grether U, Hartman P, Kuhn B, Martin R E, Plancher J M, Rudolph M G, Schuler F, Taylor S. Optimization of a novel class of benzimidazole-based farnesoid X receptor (FXR) agonists to improve physicochemical and ADME properties. Bioorg Med Chem Lett. 2011 Feb. 15; 21(4):1134-40. doi: 10.1016/j.bmcl.2010.12.123. Epub 2010 Dec. 31.

Rizzo G, Passeri D, De Franco F, Ciaccioli G, Donadio L, Rizzo G, Orlandi S, Sadeghpour B, Wang X X, Jiang T, Levi M, Pruzanski M, Adorini L. Functional characterization of the semisynthetic bile acid derivative INT-767, a dual farnesoid X receptor and TGR5 agonist. Mol Pharmacol. 2010 October; 78(4):617-30. doi: 10.1124/mol.110.064501. Epub 2010 Jul. 14.

Schuster D, Markt P, Grienke U, Mihaly-Bison J, Binder M, Noha S M, Rollinger J M, Stuppner H, Bochkov V N, Wolber G. Pharmacophore-based discovery of FXR agonists. Part I: Model development and experimental validation. Bioorg Med Chem. 2011 Dec. 1; 19(23): 7168-80. doi: 10.1016/j.bmc.2011.09.056. Epub 2011 Oct. 4.

Soisson S M, Parthasarathy G, Adams A D, Sahoo S, Sitlani A, Sparrow C, Cui J, Becker J W. Identification of a potent synthetic FXR agonist with an unexpected mode of binding and activation. Proc Natl Acad Sci USA. 2008 Apr. 8; 105(14):5337-42. doi: 10.1073/pnas.0710981105. Epub 2008 Apr. 7.

Watanabe M, Horai Y, Houten S M, Morimoto K, Sugizaki T, Arita E, Mataki C, Sato H, Tanigawara Y, Schoonjans K, Itoh H, Auwerx J. Lowering bile acid pool size with a synthetic farnesoid X receptor (FXR) agonist induces obesity and diabetes through reduced energy expenditure. J Biol Chem. 2011 Jul. 29; 286 (30):26913-20. doi: 10.1074/jbc.M111.248203. Epub 2011 Jun. 1.

Yu D, Mattern D L, Forman B M. An improved synthesis of 6α-ethylchenodeoxycholic acid (6ECDCA), a potent and selective agonist for the Farnesoid X Receptor (FXR). Steroids. 2012 November; 77(13):1335-8. doi: 10.1016/j.steroids.2012.09.002. Epub 2012 Sep. 21.

Zhang S, Wang J, Liu Q, Harnish D C. Farnesoid X receptor agonist WAY-362450 attenuates liver inflammation and fibrosis in murine model of non-alcoholic steatohepatitis. J Hepatol. 2009 August; 51(2):380-8. doi: 10.1016/j.jhep.2009.03.025. Epub 2009 May 18.

Typically FXR agonists include the class of steroid FXR agonists and non steroid FXR agonists.

In certain embodiments of the invention, the FXR agonist is selected from small molecule compounds which act as FXR modulators, which have been disclosed in the following publications:

EP1392714;
EP1568706;
EP2128158;
EP2289883;
JP2005281155;
US20030203939;
US2005080064;
US2006128764;
US20070010562;
US20070015796;
US20080038435;
US20080300235;
US20090062526;
US20090163552;
US20100093818;
US20100184809;
US20110077273;
US20110105475;
U.S. Pat. No. 6,984,560;
U.S. Pat. No. 7,671,085;
WO2000037077;
WO200040965;
WO200076523;
WO2001017994;
WO2003015771;
WO2003016280;
WO2003016288;
WO2003030612;
WO2003060078;
WO2003080803;
WO2003090745;
WO2004007521;
WO2004046162;
WO2004048349;
WO2005082925;
WO2005092328;
WO2005097097;
WO2006020680;
WO2007076260;
WO2007076260;
WO2007092751;
WO2007140174;
WO2007140183;
WO2008000643;
WO2008002573;
WO2008025539;
WO2008025540;
WO2008051942;
WO2008073825;
WO2008157270;
WO2009005998;
WO2009012125;
WO2009027264;
WO2009062874;
WO2009080555;
WO2009127321;
WO2009149795;
WO2010028981;
WO2010034649;
WO2010034657;
WO2010069604;
WO2011020615;
WO2013007387; and
WO2013037482.

Specific examples of FXR agonists include but are not limited to GW4064 (as disclosed in PCT Publication No. WO 00/37077 or in US2007/0015796), 6-ethylchenodeoxycholic acids (6ECDCA), especially 3α,7α-dihydroxy 7α-dihydroxy-6α-ethyl-5β-cholan-24-oic acid, also referred to as INT-747; 6-ethyl-ursodeoxycholic acids, INT-1103, UPF-987, WAY-362450, MFA-1, GW9662, T0901317, fexaramine, a cholic acid, a deoxycholic acid, a glycocholic acid, a glycodeoxycholic acid, a taurocholic acid, a taurodihydrofusidate, a taurodeoxycholic acid, a cholate, a glycocholate, a deoxycholate, a taurocholate, a taurodeoxycholate, a chenodeoxycholic acid, a 7-B-methyl cholic acid, and a methyl lithocholic acid.

In some embodiments, the FXR agonist is not selected from natural bile acids, preferably chenodeoxycholic acid [CDCA] or taurine- or glycine-conjugated CDCA [tauro-CDCA or glyco-CDCA] and synthetic derivatives of natural bile acids, preferably 6-Ethyl-CDCA or taurine- or glycine-conjugated 6-Ethyl-CDCA, natural non-steroidal agonists, preferably Diterpenoids such as Cafestol and Kahweol, or synthetic non-steroidal FXR agonists.

In some embodiments, the FXR agonist is selected from the group consisting of GW4064, 6ECDCA and the compound identified by the CAS Registry Number 1192171-69-9 (described in WO 2009127321 also named PXL007):

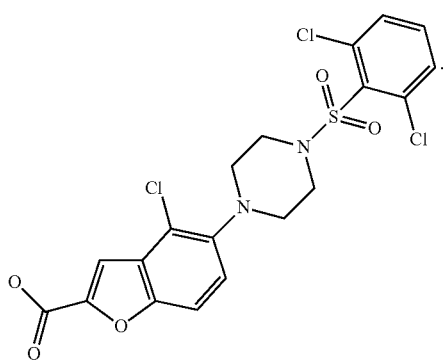 [SMILES: O=C(O)c1cc2c(Cl)c(N3CCN(S(=O)(=O)c4c(Cl)cccc4Cl)CC3)ccc2o1]

In some embodiments, the FXR agonist is the compound having the formula of:

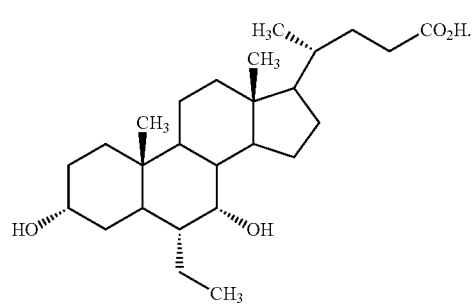 [SMILES: CC[C@@H]1C2C[C@H](O)CC[C@]2(C)C2CC[C@@]3(C)C(CCC3[C@H](C)CCC(=O)O)C2[C@@H]1O]

In some embodiments, the FXR agonist is the compound having the formula of:

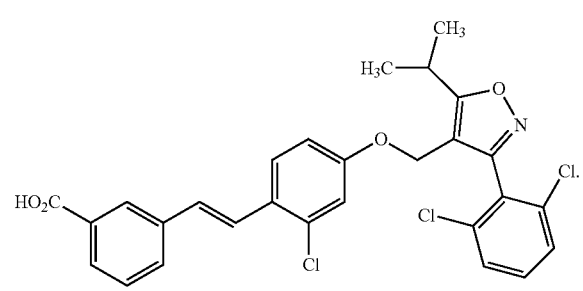 [SMILES: CC(C)c1onc(-c2c(Cl)cccc2Cl)c1COc1ccc(/C=C/c2cccc(C(=O)O)c2)c(Cl)c1]

In some embodiments, the FXR agonist is the compound having the formula of:

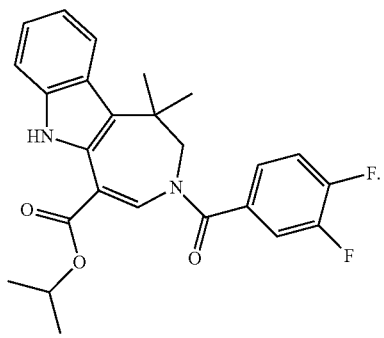 [SMILES: CC(C)OC(=O)C1=CN(C(=O)c2ccc(F)c(F)c2)CC(C)(C)c2c1[nH]c1ccccc21]

In some embodiments, the FXR agonist is selected from the group consisting of:

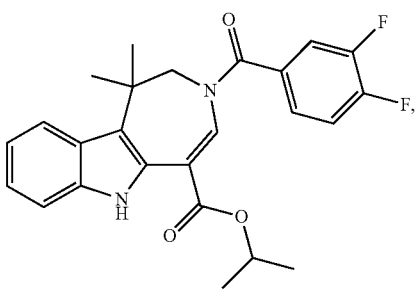

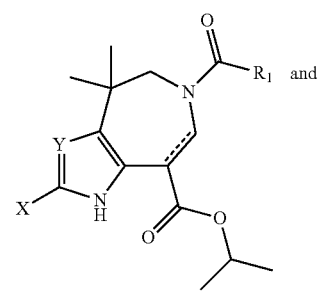

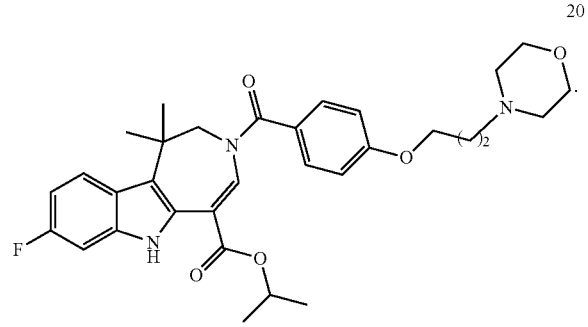

In some embodiments, the FXR agonist is selected from the group consisting of the compounds disclosed in WO2013007387, namely:

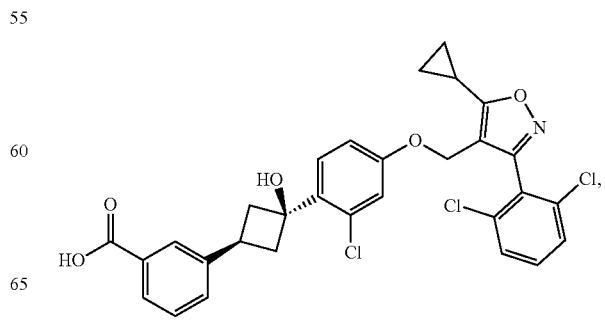

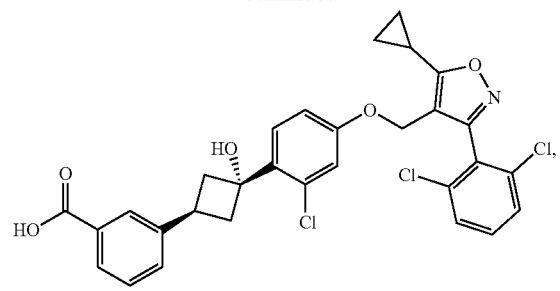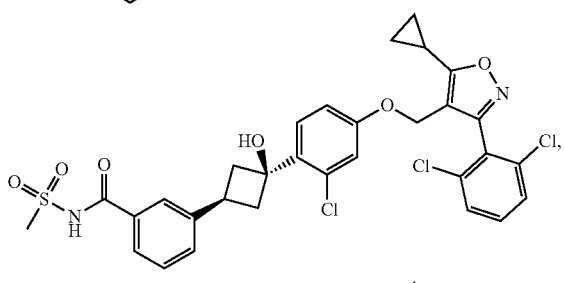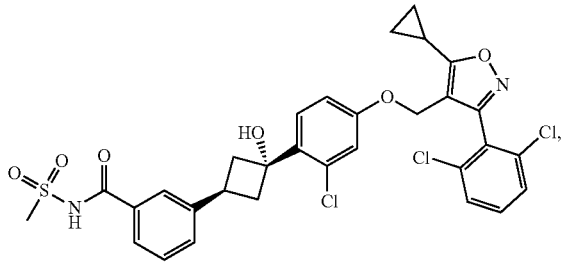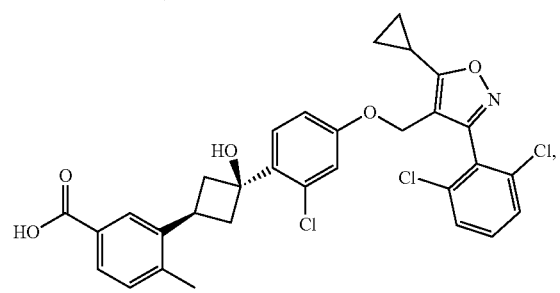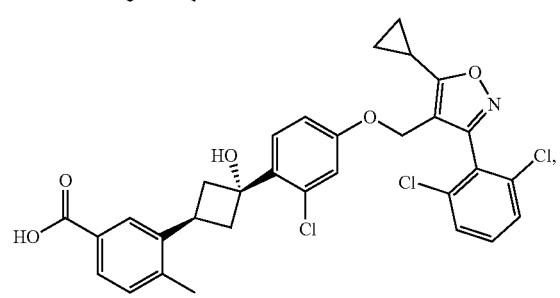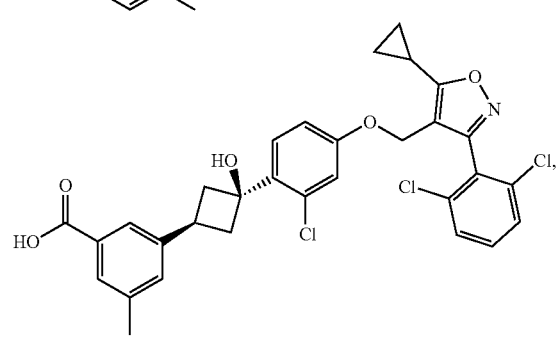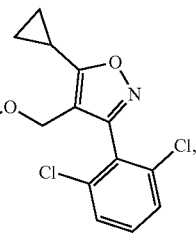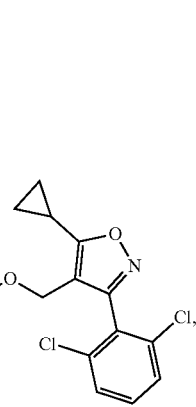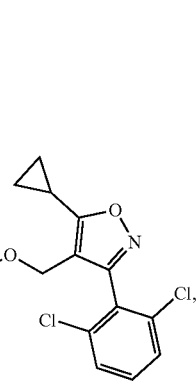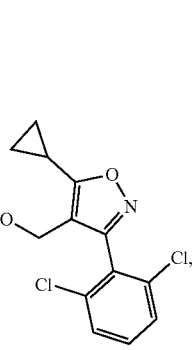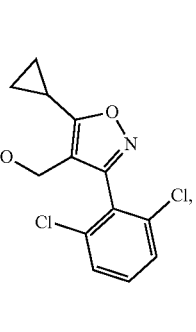

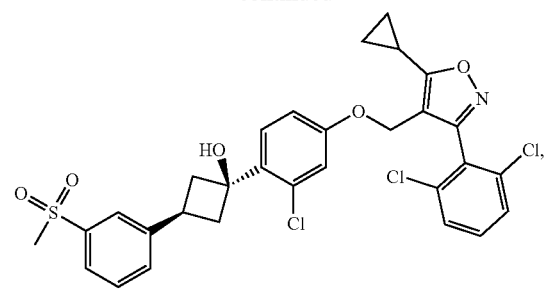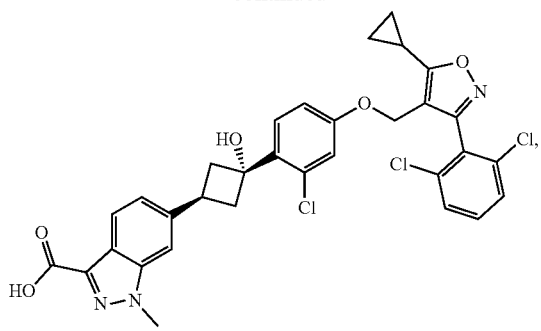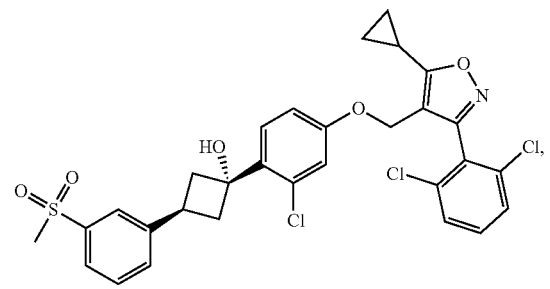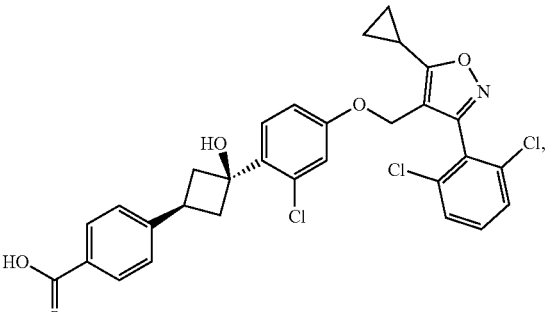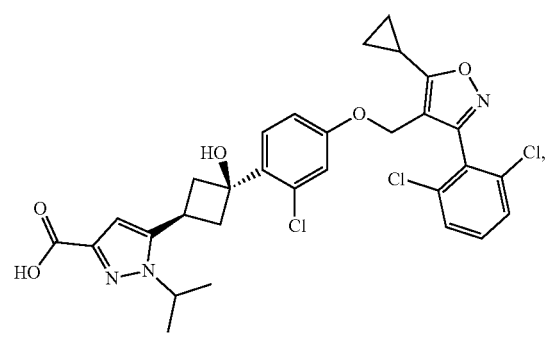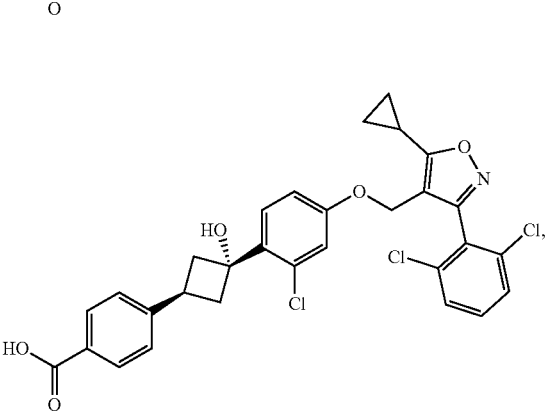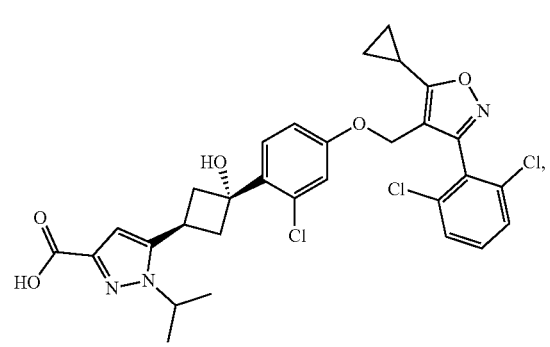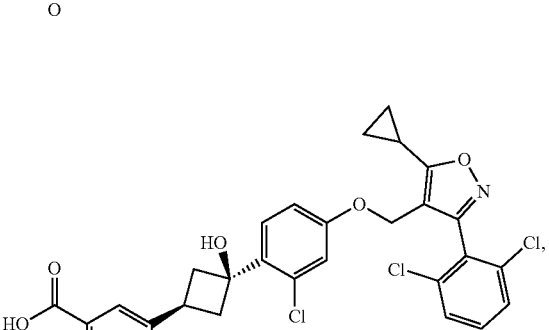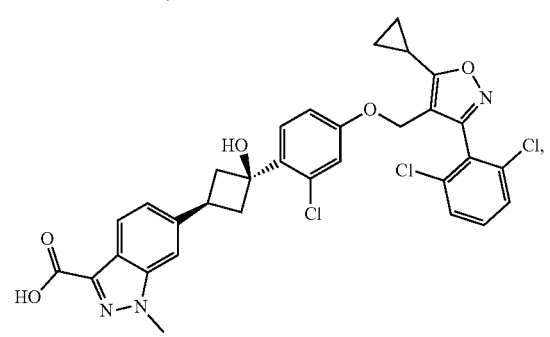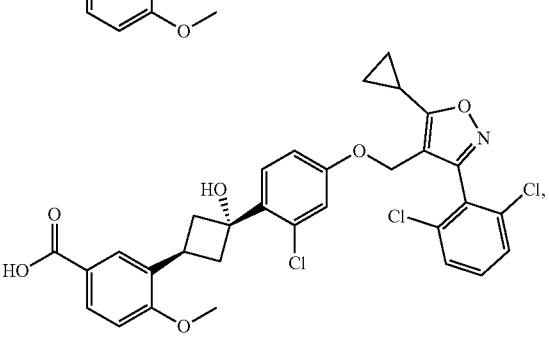

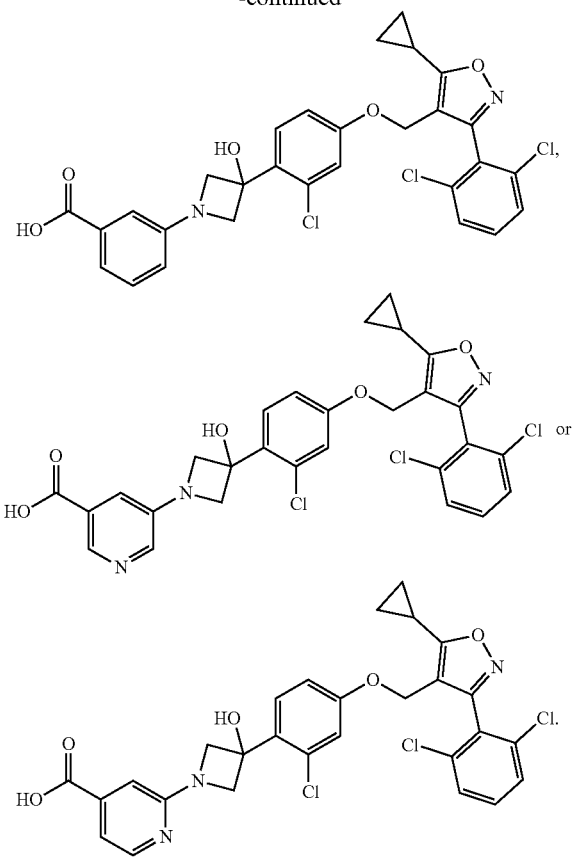

In some embodiments, the FXR agonist is selected from the group consisting of the compounds disclosed in WO2011020615, namely:

3-(2-(2-chloro-4-((5-cyclopropyl-3-(2,6-dichlorophenyl)isoxazal-4-yl)methoxy)phenyl)cyclopropyl)benzoic acid
(−)-3-(2-(2-chloro-4-((5-cyclopropyl-3-(2,6-dichlorophenyl)isoxazol-4-yl)methoxy)phenyl)cyclopropyl)benzoic acid
(+)-3-(2-(2-chloro-4-((5-cyclopropyl-3-(2,6-dichlorophenyl)isoxazol-4-yl)methoxy)phenyl)cyclopropyl)benzoic acid
3-(2-(2-chloro-4-((3-(2,6-dichlorophenyl)-5-isopropylisoxazol-4-yl)methoxy)phenyl)cyclopropyl)benzoic acid
3-(2-(2-chloro-4-((5-cyclopropyl-3-(3,5-dichloropyridin-4-yl)isoxazol-4-yl)methoxy)phenyl)cyclopropyl)benzoic acid
4-(4-((4-(2-(3-carboxyphenyl)cyclopropyl)-3-chlorophenoxy)methyl)-5-cyclopropylisoxazol-3-yl)-3,5-dichloropyridine 1-oxide
3-(2-(2-chloro-4-((1-(2,6-dichlorophenyl)-4-isopropyl-1H-1,2,3-triazol-5-yl)methoxy)phenyl)cyclopropyl)benzoic acid
4-((4-(2-(6-(1/-/-tetrazol-5-yl)pyridin-3-yl)cyclopropyl)-3-chlorophenoxy)methyl)-5-cyclopropyl-3-(2,6-dichlorophenyl)isoxazole
5-(2-(2-chloro-4-((5-cyclopropyl-3-(2,6-dichlorophenyl)isoxazol-4-yl)methoxy)phenyl)cyclopropyl)picolinic acid.
4-(2-(2-chloro-4-((5-cyclopropyl-3-(2,6-dichlorophenyl)isoxazol-4-yl)methoxy)phenyl)cyclopropyl)benzoic acid
1,3-dihydroxy-2-(hydroxymethyl)propan-2-aminium 4-(2-(2-chloro-4-((5-cyclopropyl-3-(2,6-dichlorophenyl)isoxazol-4-yl)methoxy)phenyl)cyclopropyl)benzoate
(+)-4-(2-(2-chloro-4-((5-cyclopropyl-3-(2,6-dichlorophenyl)isoxazol-4-yl)methoxy)phenyl)cyclopropyl)benzoic acid
(−)-4-(2-(2-chloro-4-((5-cyclopropyl-3-(2,6-dichlorophenyl)isoxazol-4-yl)methoxy)phenyl)cyclopropyl)benzoic acid
6-(2-(2-chloro-4-((5-cyclopropyl-3-(2,6-dichlorophenyl)isoxazol-4-yl)methoxy)phenyl)cyclopropyl)-1-methyl-1H-indazole-3-carboxylic acid
(+)-6-(2-(2-chloro-4-((5-cyclopropyl-3-(2,6-dichlorophenyl)isoxazol-4-yl)methoxy)phenyl)cyclopropyl)-1-methyl-1H-indazole-3-carboxylic acid
(−)-6-(2-(2-chloro-4-((5-cyclopropyl-3-(2,6-dichlorophenyl)isoxazol-4-yl)methoxy)phenyl)cyclopropyl)-1-methyl-1H-indazole-3-carboxylic acid
4-(2-(2-chloro-4-((5-cyclopropyl-3-(2,6-dichlorophenyl)isoxazol-4-yl)methoxy)phenyl)cyclopropyl)-N-(methylsulfonyl)benzamide
2-(4-(2-(2-chloro-4-((5-cyclopropyl-3-(2,6-dichlorophenyl)isoxazol-4-yl)methoxy)phenyl)cyclopropyl)benzamido)ethanesulfonic acid
4-((4-(2-(4-(1H-tetrazol-5-yl)phenyl)cyclopropyl)-3-chlorophenoxy)methyl)-5-cyclopropyl-3-(2,6-dichlorophenyl)isoxazole
4-(2-(2-chloro-4-((3-(2,6-dichlorophenyl)-5-(2-hydroxypropan-2-yl)isoxazol-4-yl)methoxy)phenyl)cyclopropyl)benzoic acid
5-(2-(2-chloro-4-((5-cyclopropyl-3-(2,6-dichlorophenyl)isoxazol-4-yl)methoxy)phenyl)cyclopropyl)-1-isopropyl-1H-pyrazole-3-carboxylic acid
6-(2-(2-chloro-4-((5-cyclopropyl-3-(2,6-dichlorophenyl)isoxazol-4-yl)methoxy)phenyl)cyclopropyl)-i-isopropyl-1H-indazole-3-carboxylic acid
4-(2-(2-chloro-4-((5-cyclopropyl-3-(2,6-dichlorophenyl)isoxazol-4-yl)methoxy)phenyl)cyclopropyl)-2,6-dimethylbenzoic acid
4-(2-(2-chloro-4-((5-cyclopropyl-3-(2-(trifluoromethoxy)phenyl)isoxazol-4-yl)methoxy)phenyl)cyclopropyl)benzoic acid
(+)-2-(4-(2-(2-chloro-4-((5-cyclopropyl-3-(2,6-dichlorophenyl)isoxazol-4-yl)methoxy)phenyl)cyclopropyl)benzamido)ethanesulfonic acid
2-(4-(2-(2-chloro-4-((5-cyclopropyl-3-(2,6-dichlorophenyl)isoxazol-4-yl)methoxy)phenyl)cyclopropyl)benzamido)acetic acid
and 4-(2-(2-chloro-4-((4-(2,6-dichlorophenyl)-1-isopropyl-1H-1,2,3-triazol-5-yl)methoxy)phenyl)cyclopropyl)benzoic acid.

In some embodiments, the FXR agonist is selected from the group consisting of the compounds disclosed in WO2009149795, namely:

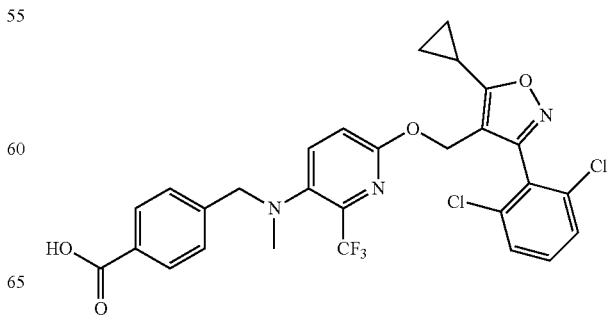

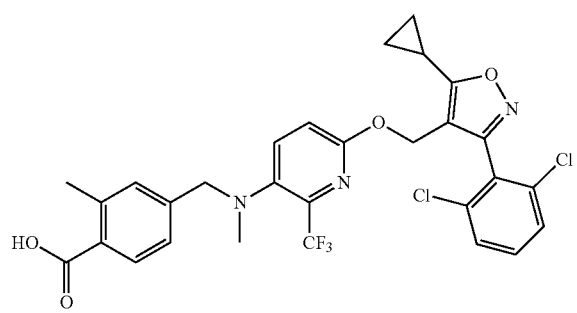
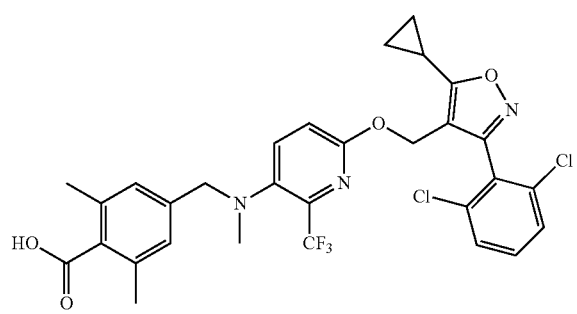
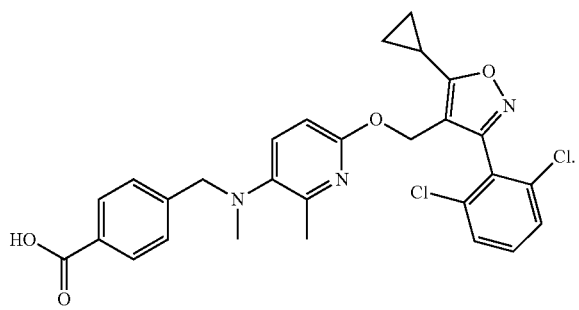
In some embodiments, the FXR agonist is selected from the group consisting of the compounds disclosed in WO2008025539, namely:
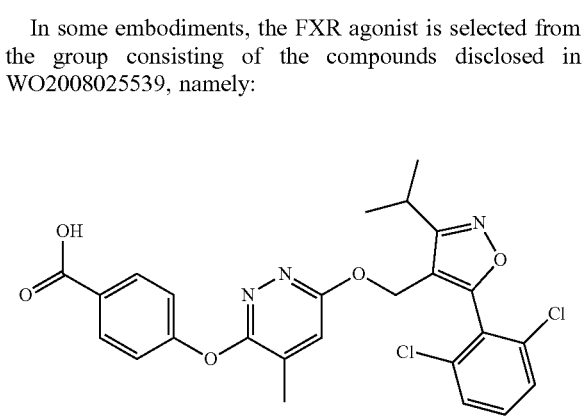
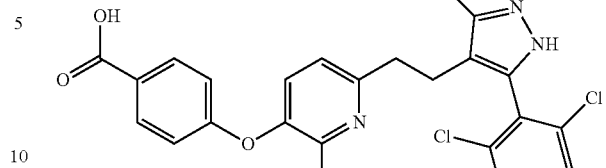
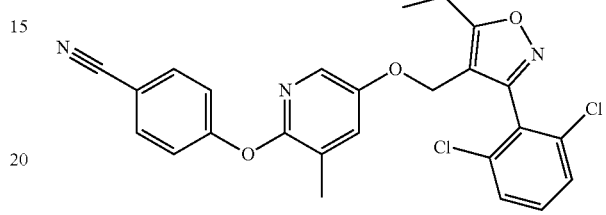
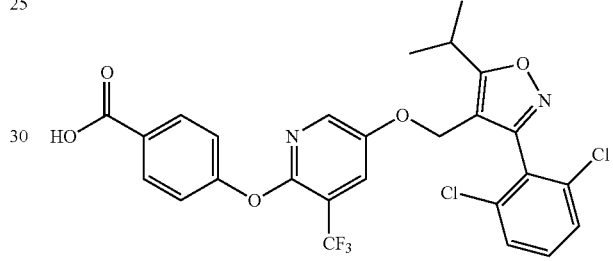
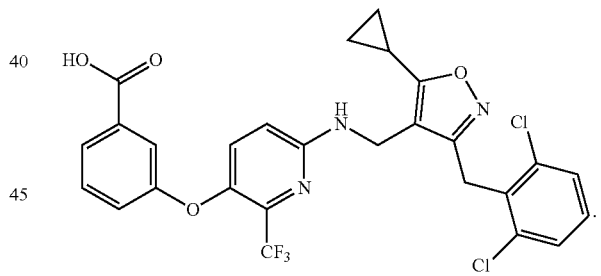
In some embodiments, the FXR agonist is selected from the group consisting of the compounds described in WO2008025540, namely:
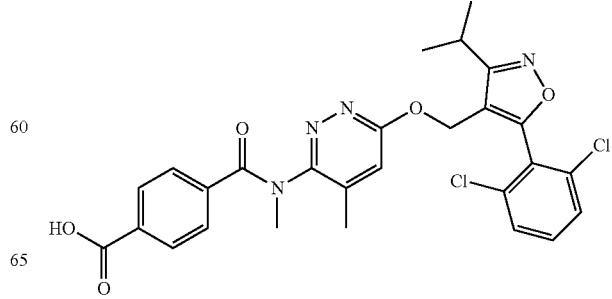

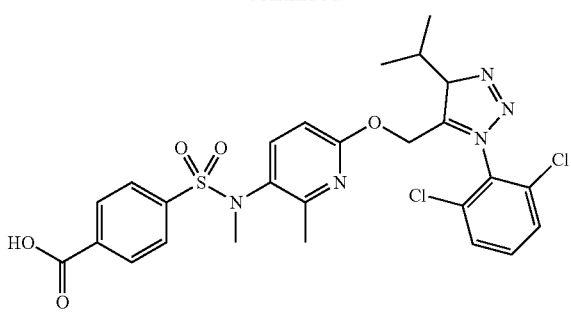

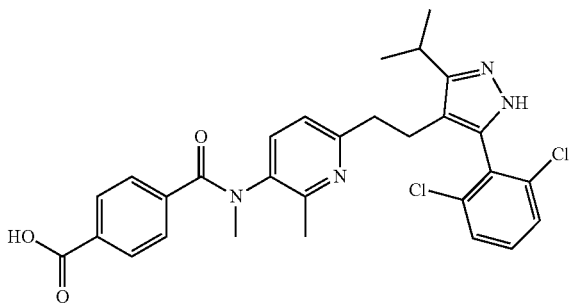

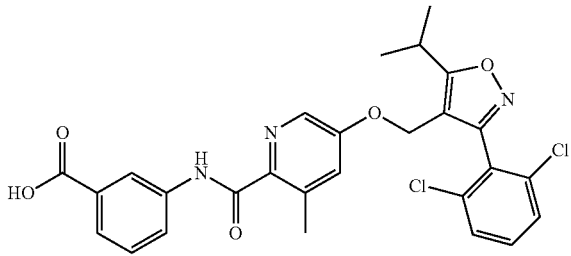

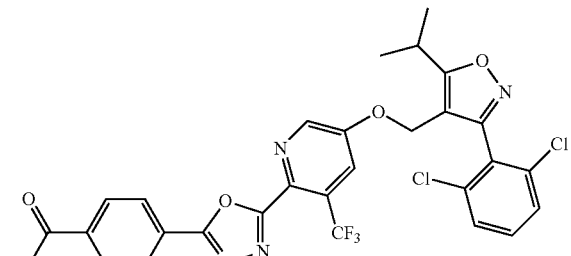

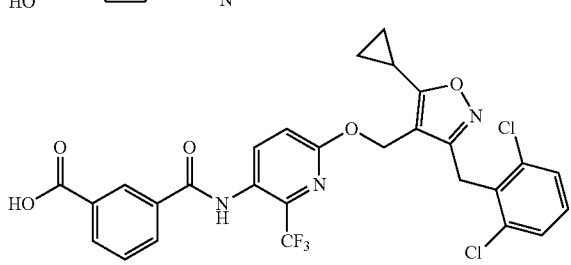

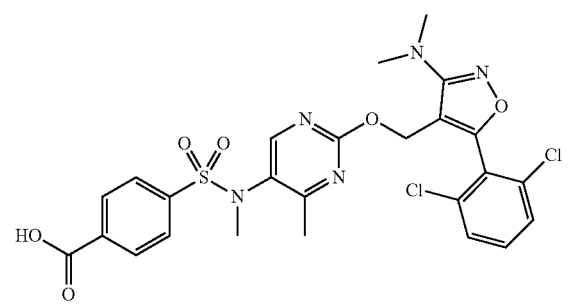

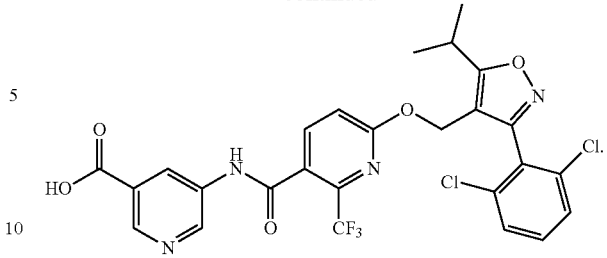

In some embodiments, the FXR agonist is selected from the group consisting of the compounds described in WO2009127321, namely:

4-(4-Bromo-2-ethoxycarbonyl-benzofuran-5-yl)-piperazine-1-carboxylic acid tert-butyl ester
4-(4-Bromo-2-carboxy-benzofuran-5-yl)-piperazine-1-carboxylic acid tert-butyl ester
4-(2-Carboxy-benzofuran-5-yl)-piperazine-1-carboxylic acid tert-butyl ester
5-[4-(3-Methoxy-benzenesulfonyl)-piperazin-1-yl]-benzofuran-2-carboxylic acid amide
5-[4-(4-Methoxy-benzenesulfonyl)-piperazin-1-yl]-benzofuran-2-carboxylic acid amide
4-(2-Ethoxycarbonyl-benzofuran-5-yl)-piperazine-1-carboxylic acid tert-butyl ester
5-[4-(3-Trifluoromethyl-benzyl)-piperazin-1-yl]-benzofuran-2-carboxylic acid amide
5-[4-(3-Chloro-benzyl)-piperazin-1-yl]-benzofuran-2-carboxylic acid amide
5-[4-(3-Fluoro-benzoyl)-piperazin-1-yl]-benzofuran-2-carboxylic acid amide
4-Bromo-5-[4-(4-methoxy-benzenesulfonyl)-piperazin-1-yl]-benzofuran-2-carboxylic acid amide-5-(4-Benzenesulfonyl-piperazin-1-yl)-benzofuran-2-carboxylic acid
4-Bromo-5-[4-(3-fluoro-benzoyl)-piperazin-1-yl]-benzofuran-2-carboxylic acid
4-Bromo-5-[4-(3-chloro-benzenesulfonyl)-piperazin-1-yl]-benzofuran-2-carboxylic acid
4-Bromo-5-[4-(3-fluoro-benzenesulfonyl)-piperazin-1-yl]-benzofuran-2-carboxylic acid
4-Bromo-5-[4-(pyrrolidine-1-carbonyl)-piperazin-1-yl]-benzofuran-2-carboxylic acid
4-Bromo-5-[4-(3-chloro-benzyl)-piperazin-1-yl]-benzofuran-2-carboxylic acid
4-(2-Carboxy-benzofuran-5-ylamino)-piperidine-1-carboxylic acid tert-butyl ester
2-[4-(4-Bromo-2-carboxy-benzofuran-5-yl)-piperazine-1-carbonyl]-pyrrolidine-1-carboxylic acid tert-butyl ester
4-(4-Chloro-2-ethoxycarbonyl-benzofuran-5-yl)-piperazine-1-carboxylic acid tert-butyl ester
4-(2-Carboxy-4-chloro-benzofuran-5-yl)-piperazine-1-carboxylic acid tert-butyl ester
5-(4-Benzyl-piperazin-1-yl)-benzofuran-2-carboxylic acid
4-Bromo-5-[4-(3-trifluoromethyl-benzyl)-piperazin-1-yl]-benzofuran-2-carboxylic acid
5-[4-(3-Methoxy-benzenesulfonyl)-piperazin-1-yl]-benzofuran-2-carboxylic acid
4-Bromo-5-[4-(3-methoxy-benzenesulfonyl)-piperazin-1-yl]-benzofuran-2-carboxylic acid
4-Bromo-5-[4-(4-methoxy-benzenesulfonyl)-piperazin-1-yl]-benzofuran-2-carboxylic acid
4-Bromo-5-[4-(pyrrolidine-2-carbonyl)-piperazin-1-yl]-benzofuran-2-carboxylic acid 5-[4-(Adamantane-1-carbonyl)-piperazin-1-yl]-4-bromo-benzofuran-2-carboxylic acid
4-Bromo-5-[4-(3-chloro-benzoyl)-piperazin-1-yl]-benzofuran-2-carboxylic acid
4-Bromo-5-[4-(2-fluoro-benzyl)-piperazin-1-yl]-benzofuran-2-carboxylic acid
4-Bromo-5-[4-(3-fluoro-benzyl)-piperazin-1-yl]-benzofuran-2-carboxylic acid
5-(4-Benzoyl-piperazin-1-yl)-4-bromo-benzofuran-2-carboxylic acid
4-Bromo-5-[4-(3-trifluoromethyl-benzyloxy)-piperidin-1-yl]-benzofuran-2-carboxylic acid
4-Bromo-5-[4-(3-chloro-benzyloxy)-piperidin-1-yl]-benzofuran-2-carboxylic acid
4-Bromo-5-[4-(2-chloro-benzenesulfonyl)-piperazin-1-yl]-benzofuran-2-carboxylic acid
4-Bromo-5-[4-(4-chloro-benzenesulfonyl)-piperazin-1-yl]-benzofuran-2-carboxylic acid
4-Bromo-5-[4-(4-fluoro-benzyl)-piperazin-1-yl]-benzofuran-2-carboxylic acid
4-Bromo-5-[4-(2-chloro-benzyl)-piperazin-1-yl]-benzofuran-2-carboxylic acid
4-Bromo-5-[4-(4-chloro-benzyl)-piperazin-1-yl]-benzofuran-2-carboxylic acid
4-Bromo-5-[4-(pyridin-2-yloxy)-piperidin-1-yl]-benzofuran-2-carboxylic acid
4-Bromo-5-[4-(3-trifluoromethyl-benzyl)-piperazin-1-yl]-benzofuran-2-carboxylic acid amide
5-[4-(3-Trifluoromethoxy-benzyl)-piperazin-1-yl]-benzofuran-2-carboxylic acid amide
4-Bromo-5-[4-(3-trifluoromethoxy-benzyl)-piperazin-1-yl]-benzofuran-2-carboxylic acid amide
4-Bromo-5-[4-(3-cyano-benzenesulfonyl)-piperazin-1-yl]-benzofuran-2-carboxylic acid
4-Bromo-5-(4-tert-butylcarbamoyl-piperazin-1-yl)-benzofuran-2-carboxylic acid
4-Bromo-5-[4-(3-fluoro-benzenesulfonyl)-piperazin-1-yl]-benzofuran-2-carboxylic acid amide
4-Bromo-5-[4-(3,5-dichloro-benzoyl)-piperazin-1-yl]-benzofuran-2-carboxylic acid amide
4-Bromo-5-[4-(3,5-difluoro-benzyl)-piperazin-1-yl]-benzofuran-2-carboxylic acid amide
4-Bromo-5-(4-pyridin-3-ylmethyl-piperazin-1-yl)-benzofuran-2-carboxylic acid
4-Bromo-5-(4-pyridin-4-ylmethyl-piperazin-1-yl)-benzofuran-2-carboxylic acid
4-Bromo-5-[4-(3-trifluoromethoxy-benzyl)-piperazin-1-yl]-benzofuran-2-carboxylic acid
4-Bromo-5-[4-(3-phenoxy-benzyl)-piperazin-1-yl]-benzofuran-2-carboxylic acid
4-Bromo-5-[4-(3,5-dimethoxy-benzyl)-piperazin-1-yl]-benzofuran-2-carboxylic acid
5-[4-(3-Allyl-2-hydroxy-benzyl)-piperazin-1-yl]-4-bromo-benzofuran-2-carboxylic acid
5-(4-Benzenesulfonyl-piperazin-1-yl)-4-bromo-benzofuran-2-carboxylic acid
4-Bromo-5-(4-tert-butylcarbamoyl-piperidin-1-yl)-benzofuran-2-carboxylic acid
4-Chloro-5-[4-(2-chloro-benzyl)-piperazin-1-yl]-benzofuran-2-carboxylic acid
4-Chloro-5-[4-(3-chloro-benzyl)-piperazin-1-yl]-benzofuran-2-carboxylic acid
4-Chloro-5-[4-(4-chloro-benzyl)-piperazin-1-yl]-benzofuran-2-carboxylic acid
4-Chloro-5-[4-(2-fluoro-benzyl)-piperazin-1-yl]-benzofuran-2-carboxylic acid
4-Chloro-5-[4-(3-fluoro-benzyl)-piperazin-1-yl]-benzofuran-2-carboxylic acid
4-Chloro-5-[4-(4-fluoro-benzyl)-piperazin-1-yl]-benzofuran-2-carboxylic acid
4-Chloro-5-[4-(3-trifluoromethyl-benzyl)-piperazin-1-yl]-benzofuran-2-carboxylic acid
4-Chloro-5-[4-(3-trifluoromethoxy-benzyl)-piperazin-1-yl]-benzofuran-2-carboxylic acid
5-[4-(3-Carboxy-benzyl)-piperazin-1-yl]-4-chloro-benzofuran-2-carboxylic acid
4-Chloro-5-(4-pyridin-3-ylmethyl-piperazin-1-yl)-benzofuran-2-carboxylic acid
4-Chloro-5-[4-(2-chloro-benzenesulfonyl)-piperazin-1-yl]-benzofuran-2-carboxylic acid
4-Chloro-5-[4-(3-chloro-benzenesulfonyl)-piperazin-1-yl]-benzofuran-2-carboxylic acid
4-Chloro-5-[4-(4-chloro-benzenesulfonyl)-piperazin-1-yl]-benzofuran-2-carboxylic acid
4-Chloro-5-[4-(4-methoxy-benzenesulfonyl)-piperazin-1-yl]-benzofuran-2-carboxylic acid
4-Chloro-5-[4-(3-methoxy-benzenesulfonyl)-piperazin-1-yl]-benzofuran-2-carboxylic acid
4-Chloro-5-[4-(3-fluoro-benzoyl)-piperazin-1-yl]-benzofuran-2-carboxylic acid
4-Chloro-5-[4-(3,5-dichloro-benzoyl)-piperazin-1-yl]-benzofuran-2-carboxylic acid
4-Chloro-5-[4-(3-fluoro-benzenesulfonyl)-piperazin-1-yl]-benzofuran-2-carboxylic acid
4-Chloro-5-[4-(3-cyano-benzenesulfonyl)-piperazin-1-yl]-benzofuran-2-carboxylic acid
4-Bromo-5-[4-(2-chloro-benzenesulfonyl)-piperazin-1-yl]-benzofuran-2-carboxylic acid amide
4-Bromo-5-[4-(3-fluoro-benzenesulfonyl)-piperazin-1-yl]-benzofuran-2-carboxylic acid ethoxy-amide
4-Bromo-5-[4-(3-trifluoromethyl-benzoyl)-piperazin-1-yl]-benzofuran-2-carboxylic acid
4-Bromo-5-[4-(3-trifluoromethoxy-benzoyl)-piperazin-1-yl]-benzofuran-2-carboxylic acid
4-Bromo-5-[4-(3-methoxy-benzoyl)-piperazin-1-yl]-benzofuran-2-carboxylic acid
4-Bromo-5-[4-(2,5-dichloro-benzoyl)-piperazin-1-yl]-benzofuran-2-carboxylic acid
4-Bromo-5-[4-(3,5-dichloro-benzoyl)-piperazin-1-yl]-benzofuran-2-carboxylic acid
4-Bromo-5-[4-(2-methyl-1H-benzoimidazole-4-carbonyl)-piperazin-1-yl]-benzofuran-2-carboxylic acid
4-Bromo-5-[4-(5-trifluoromethyl-pyridin-2-yloxy)-piperidin-1-yl]-benzofuran-2-carboxylic acid
4-Chloro-5-[4-(3-chloro-benzoyl)-piperazin-1-yl]-benzofuran-2-carboxylic acid
4-Chloro-5-[4-(2,5-dichloro-benzoyl)-piperazin-1-yl]-benzofuran-2-carboxylic acid-4-Chloro-5-[4-(3-methoxy-benzoyl)-piperazin-1-yl]-benzofuran-2-carboxylic acid
4-Chloro-5-[4-(3-trifluoromethyl-benzoyl)-piperazin-1-yl]-benzofuran-2-carboxylic acid
4-Chloro-5-[4-(3-trifluoromethoxy-benzoyl)-piperazin-1-yl]-benzofuran-2-carboxylic acid
4-Chloro-5-[4-(2-methyl-1H-benzoimidazole-4-carbonyl)-piperazin-1-yl]-benzofuran-2-carboxylic acid
5-[4-(1H-Benzoimidazole-5-carbonyl)-piperazin-1-yl]-4-chloro-benzofuran-2-carboxylic acid
4-Chloro-5-[4-(2,5-dichloro-benzyl)-piperazin-1-yl]-benzofuran-2-carboxylic acid
4-Chloro-5-[4-(3,5-dimethoxy-benzyl)-piperazin-1-yl]-benzofuran-2-carboxylic acid
4-Chloro-5-[4-(3-chloro-phenylmethanesulfonyl)-piperazin-1-yl]-benzofuran-2-carboxylic acid 5-[4-(2-Chloro-benzenesulfonyl)-piperazin-1-yl]-4-methyl-benzofuran-2-carboxylic acid 5-[4-(3-Fluoro-benzenesulfonyl)-piperazin-1-yl]-4-methyl-benzofuran-2-carboxylic acid 4-(2-Carboxy-4-methyl-benzofuran-5-yl)-piperazine-1-carboxylic acid tert-butyl ester 4-(2-Carboxy-4-chloro-benzofuran-5-yl)-[1,4]diazepane-1-carboxylic acid tert-butyl ester 4-(4-Bromo-2-carboxy-benzofuran-5-yl)-[1,4]diazepane-1-carboxylic acid tert-butyl ester 4-Bromo-5-[4-(2-chloro-benzenesulfonyl)-[1,4]diazepan-1-yl]-benzofuran-2-carboxylic acid 4-Chloro-5-[4-(2-chloro-benzenesulfonyl)-[1,4]diazepan-1-yl]-benzofuran-2-carboxylic acid 4-Chloro-5-[4-(5-trifluoromethyl-pyridin-2-yloxy)-piperidin-1-yl]-benzofuran-2-carboxylic acid 4-Bromo-5-[1-(3-chloro-benzenesulfonyl)-piperidin-4-ylamino]-benzofuran-2-carboxylic acid {4-Bromo-5-[4-(2-chloro-benzenesulfonyl)-piperazin-1-yl]-benzofuran-2-yl}-morpholin-4-yl-methanone 4-Bromo-5-[4-(2-chloro-benzenesulfonyl)-piperazin-1-yl]-benzofuran-2-carboxylic acid (2-methoxy-ethyl)-amide 4-Bromo-5-[4-(2,5-dichloro-benzenesulfonyl)-piperazin-1-yl]-benzofuran-2-carboxylic acid 4-Bromo-5-[4-(2,5-dichloro-benzyl)-piperazin-1-yl]-benzofuran-2-carboxylic acid 5-[4-(1H-Benzoimidazole-5-carbonyl)-piperazin-1-yl]-4-bromo-benzofuran-2-carboxylic acid 4-Bromo-5-[4-(2,6-dichloro-benzoyl)-piperazin-1-yl]-benzofuran-2-carboxylic acid 5-[4-(2,6-Dichloro-benzoyl)-piperazin-1-yl]-4-methyl-benzofuran-2-carboxylic acid 5-[4-(2,5-Dichloro-benzoyl)-piperazin-1-yl]-4-methyl-benzofuran-2-carboxylic acid 4-Methyl-5-[4-(3-trifluoromethoxy-benzoyl)-piperazin-1-yl]-benzofuran-2-carboxylic acid 5-[4-(2-Chloro-benzyl)-piperazin-1-yl]-4-methyl-benzofuran-2-carboxylic acid 5-[4-(3-Chloro-benzyl)-piperazin-1-ylH-methyl-benzofuran-carboxylic acid 5-[4-(2,5-Dichloro-benzyl)-piperazin-1-yl]-4-methyl-benzofuran-2-carboxylic acid 5-[4-(3-Fluoro-benzyl)-piperazin-1-yl]-4-methyl-benzofuran-2-carboxylic acid 4-Methyl-5-[4-(3-trifluoromethyl-benzyl)-piperazin-1-yl]-benzofuran-2-carboxylic acid 4-Methyl-5-[4-(3-trifluoromethoxy-benzyl)-piperazin-1-yl]-benzofuran-2-carboxylic acid 5-[4-(3-Chloro-benzenesulfonyl)-piperazin-1-yl]-4-methyl-benzofuran-2-carboxylic acid 5-[4-(2,5-Dichloro-benzenesulfonyl)-piperazin-1-yl]-4-methyl-benzofuran-2-carboxylic acid 5-[4-(3-Chloro-phenylmethanesulfonyl)-piperazin-1-yl]-4-methyl-benzofuran-2-carboxylic acid 4-Bromo-5-[4-(2-chloro-6-fluoro-benzyl)-piperazin-1-yl]-benzofuran-2-carboxylic acid 4-Chloro-5-[4-(2-chloro-6-fluoro-benzyl)-piperazin-1-yl]-benzofuran-2-carboxylic acid 4-Bromo-5-[4-(3-chloro-phenylmethanesulfonyl)-piperazin-1-yl]-benzofuran-2-carboxylic acid 4-Chloro-5-[1-(3-chloro-benzenesulfonyl)-piperidin-4-ylamino]-benzofuran-2-carboxylic acid 4-Bromo-5-(3,4-dihydro-1H-isoquinolin-2-yl)-benzofuran-2-carboxylic acid 4-Bromo-5-[4-(3-chloro-phenoxy)-piperidin-1-yl]-benzofuran-2-carboxylic acid 4-Bromo-5-[4-(4-trifluoromethyl-pyrimidin-2-yloxy)-piperidin-1-yl]-benzofuran-2-carboxylic acid 4-Bromo-5-[4-(2-fluoro-benzenesulfonyl)-piperazin-1-yl]-benzofuran-2-carboxylic acid 5-[4-(2-Fluoro-benzenesulfonyl)-piperazin-1-yl]-4-methyl-benzofuran-2-carboxylic acid 4-Bromo-5-[4-(2,6-dichloro-benzenesulfonyl)-piperazin-1-yl]-benzofuran-2-carboxylic acid 5-[4-(2,6-Dichloro-benzenesulfonyl)-piperazin-1-yl]-4-methyl-benzofuran-2-carboxylic acid 4-Chloro-5-[4-(2,6-dichloro-benzenesulfonyl)-piperazin-1-yl]-benzofuran-2-carboxylic acid 4-Bromo-5-[4-(2,3-dichloro-benzenesulfonyl)-piperazin-1-yl]-benzofuran-2-carboxylic acid 5-[4-(2,3-Dichloro-benzenesulfonyl)-piperazin-1-yl]-4-methyl-benzofuran-2-carboxylic acid 4-Chloro-5-[4-(2,3-dichloro-benzenesulfonyl)-piperazin-1-yl]-benzofuran-2-carboxylic acid 4-Chloro-5-[4-(2,5-dichloro-benzenesulfonyl)-piperazin-1-yl]-benzofuran-2-carboxylic acid 4-Bromo-5-[4-(2,3-dichloro-benzoyl)-piperazin-1-yl]-benzofuran-2-carboxylic acid 4-Methyl-5-[4-(3-trifluoromethyl-benzoyl)-piperazin-1-yl]-benzofuran-2-carboxylic acid 4-Methyl-5-[4-(2-methyl-1H-benzoimidazole-4-carbonyl)-piperazin-1-yl]-benzofuran-2-carboxylic acid 5-[4-(2-Fluoro-benzyl)-piperazin-1-yl]-4-methyl-benzofuran-2-carboxylic acid 5-[4-(2-Chloro-6-fluoro-benzyl)-piperazin-1-yl]-4-methyl-benzofuran-2-carboxylic acid 5-[4-(2,6-Dichloro-benzyl)-piperazin-1-yl]-4-methyl-benzofuran-2-carboxylic acid 4-Bromo-5-[4-(3,5-dichloro-benzyl)-piperazin-1-yl]-benzofuran-2-carboxylic acid 5-[4-(3,5-Dichloro-benzyl)-piperazin-1-yl]-4-methyl-benzofuran-2-carboxylic acid 4-Chloro-5-[4-(3,5-dichloro-benzyl)-piperazin-1-yl]-benzofuran-2-carboxylic acid 5-[4-(3-Allyl-2-hydroxy-benzyl)-piperazin-1-yl]-4-methyl-benzofuran-2-carboxylic acid 5-[4-(2,3-Dimethoxy-benzyl)-piperazin-1-yl]-4-methyl-benzofuran-2-carboxylic acid 4-Bromo-5-[4-(5-chloro-thiophen-2-ylmethyl)-piperazin-1-yl]-benzofuran-2-carboxylic acid 4-Methyl-5-[4-(5-trifluoromethyl-pyridin-2-yloxy)-piperidin-1-yl]-benzofuran-2-carboxylic acid 4-(2-Carboxy-4-cyano-benzofuran-5-yl)-piperazine-1-carboxylic acid tert-butyl ester 4-Bromo-5-[4-(4-chloro-phenoxy)-piperidin-1-yl]-benzofuran-2-carboxylic acid 4-Bromo-5-[4-(3-ethoxy-benzyl)-piperazin-1-yl]-benzofuran-2-carboxylic acid 4-Bromo-5-[4-(2-chloro-benzenesulfonyl)-piperazin-1-yl]-benzofuran-2-carboxylic acid benzylamide 5-(4-Benzo[1,3]dioxol-4-ylmethyl-piperazin-1-yl)-4-bromo-benzofuran-2-carboxylic acid 4-Bromo-5-[4-(2,6-dichloro-benzyl)-piperazin-1-yl]-benzofuran-2-carboxylic acid 4-Bromo-5-[4-(2,4-dichloro-benzyl)-piperazin-1-yl]-benzofuran-2-carboxylic acid 5-[4-(2-Allyloxy-benzyl)-piperazin-1-yl]-4-bromo-benzofuran-2-carboxylic acid 4-Bromo-5-[4-(3-trifluoromethyl-phenoxy)-piperidin-1-yl]-benzofuran-2-carboxylic acid 4-Bromo-5-[4-(4-trifluoromethyl-phenoxy)-piperidin-1-yl]-benzofuran-2-carboxylic acid 4-Bromo-5-{4-[cyclopropanecarbonyl-(2,4-dichloro-phenyl)-amino]-piperidin-1-yl}-benzofuran-2-carboxylic acid
4-Bromo-5-{4-[(4-chloro-benzyl)-cyclopropanecarbonyl-amino]-piperidin-1-yl}-benzofuran-2-carboxylic acid
5-{4-[3-(2,6-Dichloro-phenyl)-5-isopropyl-isoxazole-4-carbonyl]-piperazin-1-yl}-4-methyl-benzofuran-2-carboxylic acid
4-Bromo-5-[4-(2-trifluoromethyl-benzyl)-piperazin-1-yl]-benzofuran-2-carboxylic acid
5-[4-(3-Allyloxy-benzyl)-piperazin-1-yl]-4-bromo-benzofuran-2-carboxylic acid
5-[4-(3-Allyl-2-methoxy-benzyl)-piperazin-1-yl]-4-methyl-benzofuran-2-carboxylic acid
4-Bromo-5-[4-(3-tert-butyl-2-hydroxy-benzyl)-piperazin-1-yl]-benzofuran-2-carboxylic acid
4-Methyl-5-(4-naphthalen-1-ylmethyl-piperazin-1-yl)-benzofuran-2-carboxylic acid
4-Bromo-5-[4-(2-hydroxy-naphthalen-1-ylmethyl)-piperazin-1-yl]-benzofuran-2-carboxylic acid
4-Bromo-5-[4-(2-trifluoromethyl-benzenesulfonyl)-piperazin-1-yl]-benzofuran-2-carboxylic acid
4-Bromo-5-[4-(3-trifluoromethyl-benzenesulfonyl)-piperazin-1-yl]-benzofuran-2-carboxylic acid
4-Bromo-5-[4-(2,6-dichloro-benzenesulfonyl)-[1,4]diazepan-1-yl]-benzofuran-2-carboxylic acid
{4-Bromo-5-[4-(2,6-dichloro-benzenesulfonyl)-[1,4]diazepan-1-yl]-benzofuran-2-yl}-morpholin-4-yl-methanone
{4-Bromo-5-[4-(2,6-dichloro-benzenesulfonyl)-[1,4]diazepan-1-yl]-benzofuran-2-yl}-piperidin-1-yl-methanone
{5-[4-(3,5-Dichloro-2-hydroxy-benzenesulfonyl)-piperazin-1-yl]-4-methyl-benzofuran-2-yl}-morpholin-4-yl-methanone
{4-Bromo-5-[4-(2-fluoro-benzenesulfonyl)-piperazin-1-yl]-benzofuran-2-yl}-morpholin-4-yl-methanone
{4-Bromo-5-[4-(2-chloro-benzenesulfonyl)-piperazin-1-yl]-benzofuran-2-yl}-piperidin-1-yl-methanone
{4-Bromo-5-[4-(2,6-dichloro-benzenesulfonyl)-piperazin-1-yl]-benzofuran-2-yl}-piperidin-1-yl-methanone
{4-Bromo-5-[4-(2,6-dichloro-benzenesulfonyl)-piperazin-1-yl]-benzofuran-2-yl}-morpholin-4-yl-methanone
4-Bromo-5-[4-(2,6-dichloro-benzoyl)-[1,4]diazepan-1-yl]-benzofuran-2-carboxylic acid
5-[4-(3-Allyl-2-hydroxy-benzyl)-[1,4]diazepan-1-yl]-4-bromo-benzofuran-2-carboxylic acid
5-[4-(3,5-Dichloro-2-hydroxy-benzyl)-piperazin-1-yl]-4-methyl-benzofuran-2-carboxylic acid
4-Methyl-5-[4-(2,3,6-trichloro-benzyl)-piperazin-1-yl]-benzofuran-2-carboxylic acid
5-[4-(2,3-Dichloro-benzyl)-piperazin-1-yl]-4-methyl-benzofuran-2-carboxylic acid
4-Bromo-5-{4-[4-bromo-5-(4-fluoro-2-methoxy-phenyl)-3-methyl-pyrazol-1-yl]-piperidin-1-yl}-benzofuran-2-carboxylic acid
4-Bromo-5-(4-{[(4-chloro-benzyl)-cyclopropylmethyl-amino]-methyl}-piperidin-1-yl)-benzofuran-2-carboxylic acid
{4-Bromo-5-[4-(2,6-dichloro-benzoyl)-[1,4]diazepan-1-yl]-benzofuran-2-yl}-morpholin-4-yl-methanone
4-Chloro-5-[4-(2,6-dichloro-benzoyl)-piperazin-1-yl]-benzofuran-2-carboxylic acid
4-Chloro-5-[1-(2,6-dichloro-benzenesulfonyl)-piperidin-4-ylamino]-benzofuran-2-carboxylic acid
{4-Chloro-5-[4-(2,3-dichloro-benzenesulfonyl)-piperazin-1-yl]-benzofuran-2-yl}-morpholin-4-yl-methanone
{4-Bromo-5-[4-(2,6-dichloro-benzenesulfonyl)-piperazin-1-yl]-benzofuran-2-yl}-(4-methyl-piperazin-1-yl)-methanone
4-Bromo-5-[4-(2,6-dichloro-benzenesulfonyl)-piperazin-1-yl]-benzofuran-2-carboxylic acid (2-dimethylamino-ethyl)-amide
4-Chloro-5-[4-(2-hydroxy-benzyl)-piperazin-1-yl]-benzofuran-2-carboxylic acid
{5-[4-(2,6-Dichloro-benzyl)-piperazin-1-yl]-4-methyl-benzofuran-2-yl}-morpholin-4-yl-methanone
4-Chloro-5-[4-(2,6-dichloro-benzenesulfonyl)-[1,4]diazepan-1-yl]-benzofuran-2-carboxylic acid
5-[4-(2,3-Dichloro-benzenesulfonyl)-[1,4]diazepan-1-yl]-4-methyl-benzofuran-2-carboxylic acid
{5-[4-(2,3-Dichloro-benzenesulfonyl)-[1,4]diazepan-1-yl]-4-methyl-benzofuran-2-yl}-morpholin-4-yl-methanone
4-Chloro-5-[4-(2,3-dichloro-benzenesulfonyl)-[1,4]diazepan-1-yl]-benzofuran-2-carboxylic acid
{4-Chloro-5-[4-(2,3-dichloro-benzenesulfonyl)-[1,4]diazepan-1-yl]-benzofuran-2-yl}-morpholin-4-yl-methanone
4-Chloro-5-[4-(2,5-dichloro-benzenesulfonyl)-[1,4]diazepan-1-yl]-benzofuran-2-carboxylic acid
{4-Chloro-5-[4-(2,5-dichloro-benzenesulfonyl)-[1,4]diazepan-1-yl]-benzofuran-2-yl}-morpholin-4-yl-methanone
5-[4-(2,5-Dichloro-benzenesulfonyl)-[1,4]diazepan-1-yl]-4-methyl-benzofuran-2-carboxylic acid
{5-[4-(2,5-Dichloro-benzenesulfonyl)-[1,4]diazepan-1-yl]-4-methyl-benzofuran-2-yl}-morpholin-4-yl-methanone
{4-Chloro-5-[4-(2,6-dichloro-benzenesulfonyl)-[1,4]diazepan-1-yl]-benzofuran-2-yl}-morpholin-4-yl-methanone
4-Chloro-5-[4-(2-chloro-6-hydroxy-benzyl)-piperazin-1-yl]-benzofuran-2-carboxylic acid
4-Chloro-5-[4-(2-chloro-6-methoxy-benzyl)-piperazin-1-yl]-benzofuran-2-carboxylic acid
4-Chloro-5-[4-(3-ethoxy-2-hydroxy-benzyl)-piperazin-1-yl]-benzofuran-2-carboxylic acid
4-Chloro-5-[4-(2-chloro-3-trifluoromethyl-benzyl)-piperazin-1-yl]-benzofuran-2-carboxylic acid
5-{4-[3-(2,6-Dichloro-phenyl)-5-isopropyl-isoxazol-4-ylmethyl]-piperazin-1-yl}-4-methyl-benzofuran-2-carboxylic acid
5-[4-(2,6-Dichloro-benzyl)-piperazin-1-yl]-4-methyl-benzofuran-2-carboxylic acid amide
5-[4-(2,6-Dichloro-benzyl)-[1,4]diazepan-1-yl]-4-methyl-benzofuran-2-carboxylic acid
{5-[4-(2,6-Dichloro-benzyl)-[1,4]diazepan-1-yl]-4-methyl-benzofuran-2-yl}-(4-methyl-piperazin-1-yl)-methanone
{4-Bromo-5-[4-(2,6-dichloro-benzoyl)-[1,4]diazepan-1-yl]-benzofuran-2-yl}-piperidin-1-yl-methanone
4-Bromo-5-[1-(2,6-dichloro-benzoyl)-piperidin-4-ylamino]-benzofuran-2-carboxylic acid
4-Bromo-5-[1-(2,3-dichloro-benzoyl)-piperidin-4-ylamino]-benzofuran-2-carboxylic acid
4-Chloro-5-[4-(2,3-dihydro-indol-1-yl)-piperidin-1-yl]-benzofuran-2-carboxylic acid
4-[2-(1Htetrazol-5-yl)-benzofuran-5-yl]-piperazine-1-carboxylic acid terbutyl ester
5-(4-Benzhydryl-piperazin-1-yl)-4-methyl-benzofuran-2-carboxylic acid
4-Bromo-5-[4-(2,6-dichloro-benzenesulfonylamino)-piperidin-1-yl]-benzofuran-2-carboxylic acid
4-Chloro-5-[4-(2-methyl-5-thiophen-2-yl-2H-pyrazol-3-yl-methyl)-piperazin-1-yl]-benzofuran-2-carboxylic acid
5-[(1S,4S)-5-(2,6-Dichloro-benzenesulfonyl)-2,5-diaza-bicyclo[2.2.1]hept-2-yl]-4-methyl-benzofuran-2-carboxylic acid 5-[4-(2>4-Dichloro-phenylcarbamoyl)-piperidin-1-yl]-4-methyl-benzofuran-2-carboxylic acid and the stereoisomeric forms, mixtures of stereoisomeric forms or pharmaceutically acceptable salts forms thereof.

In some embodiments, the FXR agonist is selected from the group consisting of the compounds described in WO2008000643, namely:

2,N-dicyclohexyl-2-(2-phenyl-benzoimidazol-1-yl)-acetamide hydrogen chloride,
2-[2-(4-chloro-phenyl)-benzoimidazol-1-yl]-4-methyl-pentanoic acid cyclohexylamide,
4-{1-[cyclohexyl-(4-morpholin-4-yl-phenylcarbamoyl)-methyl]-1H-benzoimidazol-2-yl}-benzoic acid methyl ester hydrochloride,
2,N-dicyclohexyl-2-[5,6-dichloro-2-(2,4-dimethoxy-phenyl)-benzoimidazol-1-yl]-acetamide,
2-cyclohexyl-2-[2-(2,4-dimethoxy-phenyl)-benzoimidazol-1-yl]-N-isopropyl-acetamide hydrogen chloride,
2,N-dicyclohexyl-2-[2-(4-methoxy-phenyl)-benzoimidazol-1-yl]-acetamide hydrogen chloride,
2,N-dicyclohexyl-2-[2-(3-methoxy-phenyl)-benzoimidazol-1-yl]-acetamide hydrogen chloride,
2,N-dicyclohexyl-2-[2-(2-methoxy-phenyl)-benzoimidazol-1-yl]-acetamide hydrogen chloride,
2,N-dicyclohexyl-2-(2-naphthalen-1-yl-benzoimidazol-1-yl)-acetamide hydrogen chloride, 2,N-dicyclohexyl-2-[2-(3-ethoxy-phenyl)-benzoimidazol-1-yl]-acetamide hydrogen chloride,
N-cyclohexyl-2-[2-(2,4-dimethoxy-phenyl)-benzoimidazol-1-yl]-4-phenyl-butyramide,
N-cyclohexyl-2-[2-(2,4-dimethoxy-phenyl)-benzoimidazol-1-yl]-3-methyl-butyramide hydrogen chloride,
N-cyclohexyl-2-[2-(2,4-dimethoxy-phenyl)-benzoimidazol-1-yl]-3-phenyl-propionamide hydrogen chloride,
N-cyclohexyl-2-[2-(2,4-dimethoxy-phenyl)-benzoimidazol-1-yl]-2-pyridin-2-yl-acetamide hydrogen chloride,
N-cyclohexyl-2-cyclopentyl-2-[2-(2,4-dimethoxy-phenyl)-benzoimidazol-1-yl]-acetamide hydrogen chloride,
4-{1-[cyclohexyl-(cyclohexylcarbamoyl-methyl)]-1H-benzoimidazol-2-yl}-benzoic acid methyl ester,
2,N-dicyclohexyl-2-(2-naphthalen-2-yl-benzoimidazol-1-yl)-acetamide,
2,N-dicyclohexyl-2-[2-(3-thiophen-2-yl)-phenyl)-benzoimidazol-1-yl]-acetamide,
2,N-dicyclohexyl-2-[2-(5-phenyl-thiophen-2-yl)-benzoimidazol-1-yl]-acetamide,
3-{1-[cyclohexyl-(cyclohexylcarbamoyl-methyl)]-1H-benzoimidazol-2-yl}-benzoic acid methyl ester,
2-[2-(3-hydroxy-phenyl)-benzoimidazol-1-yl]-4-methyl-pentanoic acid cyclohexylamide,
2-[2-(4-hydroxymethyl-phenyl)-benzoimidazol-1-yl]-4-methyl-pentanoic acid cyclohexylamide,
2-[2-(1H-indol-5-yl)-benzoimidazol-1-yl]-4-methyl-pentanoic acid cyclohexylamide,
2-[2-(1H-indol-6-yl)-benzoimidazol-1-yl]-4-methyl-pentanoic acid cyclohexylamide,
2-[2-(4-amino-phenyl)-benzoimidazol-1-yl]-4-methyl-pentanoic acid cyclohexylamide,
2-cyclohexyl-2-[2-(2,4-dimethoxy-phenyl)-benzoimidazol-1-yl]-N-((R) 1-phenyl-ethyl)-acetamide,
2,N-dicyclohexyl-2-[2-(4-hydroxymethyl-phenyl)-benzoimidazol-1-yl]-acetamide,
N-cyclohexyl-2-[2-(2,3-dimethoxy-phenyl)-benzoimidazol-1-yl]-4-phenyl-butyramide,
2-[2-(3-cyano-phenyl)-benzoimidazol-1-yl]-2,N-dicyclohexyl-acetamide,
2,N-dicyclohexyl-2-{2-[4-(1H-tetrazol-5-yl)-phenyl]-benzoimidazol-1-yl}-acetamide hydrogen chloride,
3-[1-(benzylcarbamoyl-cyclopentyl-methyl)-1H-benzoimidazol-2-yl]-benzoic acid methyl ester,
2-[2-(2,4-dimethoxy-phenyl)-benzoimidazol-1-yl]-hexanoic acid cyclohexylamide,
2,N-dicyclohexyl-2-[2-(3-methanesulfonyl-phenyl)-benzoimidazol-1-yl]-acetamide hydrogen chloride,
N-benzyl-2-cyclohexyl-2-[2-(2,4-dimethoxy-phenyl)-benzoimidazol-1-yl]-acetamide,
2-cyclohexyl-2-[2-(2,4-dimethoxy-phenyl)-benzoimidazol-1-yl]-N-(1-methyl-butyl)-acetamide,
4-[1-(benzylcarbamoyl-cyclopentyl-methyl)-1H-benzoimidazol-2-yl]-benzoic acid methyl ester,
N-cyclopentyl-2-[2-(3-methoxy-phenyl)-benzoimidazol-1-yl]-4-phenyl-butyramide hydrogen chloride,
2,N-dicyclohexyl-2-[2-(2,4-dimethoxy-phenyl)-5-methyl-benzoimidazol-1-yl]-acetamide hydrogen chloride,
2-[2-(4-chloro-phenyl)-benzoimidazol-1-yl]-2,N-dicyclopentyl-acetamide hydrogen chloride,
N-benzhydryl-2-cyclohexyl-2-[2-(2,4-dimethoxy-phenyl)-benzoimidazol-1-yl]-acetamide, N-benzyl-2-(2-naphthalen-1-yl-benzoimidazol-1-yl)-4-phenyl-butyramide,
2-cyclohexyl-2-[2-(2,4-dimethoxy-phenyl)-benzoimidazol-1-yl]-N-(4-methoxy-phenyl)-acetamide,
2,N-dicyclohexyl-2-[2-(2,4-dimethoxy-phenyl)-4-methyl-benzoimidazol-1-yl]-acetamide,
2,N-dicyclohexyl-2-{2-[3-(2-oxo-pyrrolidin-1-yl)-phenyl]-benzoimidazol-1-yl}-acetamide hydrogen chloride,
2,N-dicyclohexyl-2-[2-(2-oxo-1,2-dihydro-pyridin-4-yl)-benzoimidazol-1-yl]-acetamide,
N-cyclopentyl-2-[2-(2-methoxy-phenyl)-benzoimidazol-1-yl]-4-phenyl-butyramide, 2-cyclohexyl-2-[2-(2,4-dimethoxy-phenyl)-benzoimidazol-1-yl]-N-pentyl-acetamide,
N-benzyl-2-[2-(4-chloro-phenyl)-benzoimidazol-1-yl]-2-cyclopentyl-acetamide hydrogen chloride,
2,N-dicyclopentyl-2-(2-naphthalene-1-yl-benzoimidazol-1-yl)-acetamide,
2-[2-(3-cyano-phenyl)-benzoimidazol-1-yl]-N-cyclohexyl-4-phenyl-butyramide,
2-[2-(4-hydroxy-phenyl)-benzoimidazol-1-yl]-4-methyl-pentanoic acid cyclohexylamide hydrogen chloride,
N-tert-butyl-2-cyclohexyl-2-[2-(2,4-dimethoxy-phenyl)-benzoimidazol-1-yl]-acetamide,
4-[1-(1-benzylcarbamoyl-3-phenyl-propyl)-1H-benzoimidazol-2-yl]-benzoic acid methyl ester,
4-[1-(1-cyclohexylcarbamoyl-3-phenyl-propyl)-1H-benzoimidazol-2-yl]-benzoic acid methyl ester,
2,N-dicyclopentyl-2-[2-(2-methoxy-phenyl)-benzoimidazol-1-yl]-acetamide,
2,N-dicyclohexyl-2-[2-(2,4-dimethoxy-phenyl)-naphtho[2,3-d]imidazol-1-yl]-acetamide,
2-[2-(2,3-dimethoxy-phenyl)-benzoimidazol-1-yl]-4-methyl-pentanoic acid cyclohexylamide,
N-benzyl-2-[2-(2-methoxy-phenyl)-benzoimidazol-1-yl]-4-phenyl-butyramide, 2-cyclohexyl-2-[2-(2,4-dimethoxy-phenyl)-benzoimidazol-1-yl]-N-(3-isopropoxy-propyl)-acetamide,
2-[2-(2,4-dimethoxy-phenyl)-benzoimidazol-1-yl]-N-isopropyl-4-phenyl-butyramide,
N-benzyl-2-cyclopentyl-2-(2-naphthalen-1-yl-benzoimidazol-1-yl)-acetamide,
2,N-dicyclohexyl-2-[2-(2,3-dimethoxy-phenyl)-benzoimidazol-1-yl]-acetamide, 2-[2-(2,4-dimethoxy-phenyl)-benzoimidazol-1-yl]-4-methyl-pentanoic acid cyclohexylamide, 2-cyclohexyl-2-[2-(2,3-dimethoxy-phenyl)-benzoimidazol-1-yl]-N-isopropyl-acetamide,
2-[2-(2,3-dimethoxy-phenyl)-benzoimidazol-1-yl]-N-isopropyl-4-phenyl-butyramide,
2-[2-(4-Acetyl-phenyl)-benzoimidazol-1-yl]-N-cyclohexyl-4-phenyl-butyramide,
N-benzyl-2-[2-(4-chloro-phenyl)-benzoimidazol-1-yl]-4-phenyl-butyramide hydrogen chloride,
4-[1-(1-isopropylcarbamoyl-pentyl)-1H-benzoimidazol-2-yl]-benzoic acid methyl ester,
N-butyl-2-[2-(2,4-dimethoxy-phenyl)-benzoimidazol-1-yl]-2-phenyl-acetamide,
2-[2-(2,3-dimethoxy-phenyl)-benzoimidazol-1-yl]-4-methyl-pentanoic acid isopropylamide,
2-benzo[1,3]dioxol-5-yl-N-butyl-2-[2-(2,3-dimethoxy-phenyl)-benzoimidazol-1-yl]-acetamide,
2-benzo[1,3]dioxol-5-yl-N-butyl-2-[2-(2,4-dimethoxy-phenyl)-benzoimidazol-1-yl]-acetamide,
N-butyl-2-[2-(2,4-dimethoxy-phenyl)-benzoimidazol-1-yl]-2-(2-fluoro-phenyl)-acetamide,
N-cyclopentyl-2-[2-(3-hydroxy-phenyl)-benzoimidazol-1-yl]-4-phenyl-butyramide,
2-[2-(4-acetyl-phenyl)-benzoimidazol-1-yl]-hexanoic acid isopropylamide,
N-butyl-2-[2-(2,3-dimethoxy-phenyl)-benzoimidazol-1-yl]-2-phenyl-acetamide,
2-[2-(4-acetyl-phenyl)-benzoimidazol-1-yl]-4-methyl-pentanoic acid cyclohexylamide,
N-butyl-2-[2-(2,3-dimethoxy-phenyl)-benzoimidazol-1-yl]-2-o-tolyl-acetamide,
N-butyl-2-[2-(2,3-dimethoxy-phenyl)-benzoimidazol-1-yl]-2-(4-methoxy-phenyl)-acetamide,
N-butyl-2-[2-(2,3-dimethoxy-phenyl)-benzoimidazol-1-yl]-2-(2-fluoro-phenyl)-acetamide,
N-butyl-2-[2-(2,3-dimethoxy-phenyl)-benzoimidazol-1-yl]-2-(4-dimethylamino-phenyl)-acetamide,
2-[2-(2,3-dimethoxy-phenyl)-benzoimidazol-1-yl]-hexanoic acid isopropylamide,
4-{1-[(2-fluoro-phenyl)-isopropylcarbamoyl-methyl]-1H-benzoimidazol-2-yl}-benzoic acid methyl ester,
2-[2-(3-cyano-phenyl)-benzoimidazol-1-yl]-4-methyl-pentanoic acid cyclohexylamide,
2-[2-(3-chloro-phenyl)-benzoimidazol-1-yl]-4-methyl-pentanoic acid cyclohexylamide,
N-butyl-2-[2-(2,4-dimethoxy-phenyl)-benzoimidazol-1-yl]-2-(4-methoxy-phenyl)-acetamide,
N-benzyl-2-[2-(3-methoxy-phenyl)-benzoimidazol-1-yl]-4-phenyl-butyramide hydrogen chloride,
2-(4-chloro-phenyl)-2-[2-(2,3-dimethoxy-phenyl)-benzoimidazol-1-yl]-N-isopropyl-acetamide,
N-butyl-2-[2-(2,4-dimethoxy-phenyl)-benzoimidazol-1-yl]-2-(4-dimethylamino-phenyl)-acetamide,
2-[2-(4-hydroxy-phenyl)-benzoimidazol-1-yl]-N-isopropyl-4-phenyl-butyramide,
2-[2-(4-hydroxy-phenyl)-benzoimidazol-1-yl]-4-methyl-pentanoic acid cyclohexylamide,
2-[2-(3-chloro-phenyl)-benzoimidazol-1-yl]-N-isopropyl-4-phenyl-butyramide,
N-butyl-2-(4-chloro-phenyl)-2-[2-(2,4-dimethoxy-phenyl)-benzoimidazol-1-yl]-acetamide,
2-[2-(3-cyano-phenyl)-benzoimidazol-1-yl]-N-isopropyl-4-phenyl-butyramide,
2-[2-(4-acetyl-phenyl)-benzoimidazol-1-yl]-N-isopropyl-2-(4-methoxy-phenyl)acetamide,
4-{1-[isopropylcarbamoyl-(4-methoxy-phenyl)-methyl]-1H-benzoimidazol-2-yl}-benzoic acid methyl ester,
4-[1-(isopropylcarbamoyl-phenyl-methyl)-1H-benzoimidazol-2-yl]-benzoic acid methyl ester,
N-isopropyl-2-[2-(1-methyl-1H-pyrrol-2-yl)-benzoimidazol-1-yl]-4-phenyl-butyramide,
2-[2-(3-cyano-phenyl)-benzoimidazol-1-yl]-hexanoic acid isopropylamide,
2-[2-(4-hydroxy-phenyl)-benzoimidazol-1-yl]-pentanoic acid isopropylamide,
2-benzo[1,3]dioxol-5-yl-N-butyl-2-[2-(1-methyl-1H-pyrrol-2-yl)-benzoimidazol-1-yl]-acetamide,
2-cyclohexyl-2-[2-(2,4-dimethoxy-phenyl)-benzoimidazol-1-yl]-N-(2,6-dimethyl-phenyl)-acetamide,
2,N-dicyclohexyl-2-[2-(2,4-dimethoxy-phenyl)-benzoimidazol-1-yl]-acetamide,
2-cyclohex-3-enyl-N-cyclohexyl-2-[2-(2,4-dimethoxy-phenyl)-benzoimidazol-1-yl]-acetamide,
2-[2-(4-cyano-phenyl)-benzoimidazol-1-yl]-2,N-dicyclohexyl-acetamide hydrogen chloride,
2-cyclohexyl-N-cyclopentyl-2-[2-(2,4-dimethoxy-phenyl)-benzoimidazol-1-yl]-acetamide,
2,N-dicyclohexyl-2-[2-(2,4-dimethoxy-phenyl)-5,6-difluoro-benzoimidazol-1-yl]-acetamide,
2,N-dicyclohexyl-2-[2-(2,4-dimethoxy-phenyl)-6-methyl-benzoimidazol-1-yl]-acetamide,
2-[2-(4-chloro-phenyl)-benzoimidazol-1-yl]-2,N-dicyclohexyl-acetamide,
2,N-dicyclohexyl-2-[2-(4-sulfamoyl-phenyl)-benzoimidazol-1-yl]-acetamide hydrogen chloride,
2-cyclohexyl-2-[2-(2,4-dimethoxy-phenyl)-benzoimidazol-1-yl]-N-(1,1,3,3-tetramethyl-butyl)-acetamide,
4-{[1-cyclopentyl-(cyclopentylcarbamoyl-methyl)]-1H-benzoimidazol-2-yl}-benzoic acid methyl ester hydrogen chloride,
2,N-dicyclohexyl-2-(2-quinolin-6-yl-benzoimidazol-1-yl)-acetamide hydrogen chloride,
2-[2-(4-amino-phenyl)-benzoimidazol-1-yl]-2,N-dicyclohexyl-acetamide,
2-[2-(2,4-dimethoxy-phenyl)-benzoimidazol-1-yl]-5-phenyl-pentanoic acid cyclohexylamide hydrogen chloride,
4-[1-(1-cyclopentylcarbamoyl-3-phenyl-propyl)-1H-benzoimidazol-2-yl]-benzoic acid methyl ester,
2,N-dicyclohexyl-2-[2-(4-dimethylsulfamoyl-phenyl)-benzoimidazol-1-yl]-acetamide hydrogen chloride,
2,N-dicyclohexyl-2-[2-(3-sulfamoyl-phenyl)-benzoimidazol-1-yl]-acetamide hydrogen chloride,
2,N-dicyclohexyl-2-{2-[3-(1H-tetrazol-5-yl)-phenyl]-benzoimidazol-1-yl}-acetamide hydrogen chloride,
2,N-dicyclohexyl-2-{2-[4-(1H-imidazol-2-yl)-phenyl]-benzoimidazol-1-yl}-acetamide hydrogen chloride,
2,N-dicyclohexyl-2-[2-(4-imidazol-1-yl-phenyl)-benzoimidazol-1-yl]-acetamide hydrogen chloride,
2,N-dicyclohexyl-2-[2-(4-[1,2,4]triazol-4-yl-phenyl)-benzoimidazol-1-yl]-acetamide hydrogen chloride,
2,N-dicyclohexyl-2-{2-[4-(1H-pyrazol-4-yl)-phenyl]-benzoimidazol-1-yl}-acetamide hydrogen chloride,
2,N-dicyclohexyl-2-[2-(4-[1,2,3]thiadiazol-4-yl-phenyl)-benzoimidazol-1-yl]-acetamide hydrogen chloride,
2,N-dicyclohexyl-2-[2-(1,3-dioxo-2,3-dihydro-1H-isoindol-5-yl)-benzoimidazol-1-yl]-acetamide hydrogen chloride,
2,N-dicyclohexyl-2-[2-(3-tetrazol-1-yl-phenyl)-benzoimidazol-1-yl]-acetamide hydrogen chloride,
4-[1-(cyclohexyl-3-methoxycarbonylphenylcarbamoyl-methyl)-1H-benzoimidazol-2-yl]-benzoic acid methyl ester hydrogen chloride,
trans 4-(1-{cyclohexyl-[(4-methoxycarbonyl-cyclohexylmethyl)-carbamoyl]-methyl}-1H-benzoimidazol-2-yl)-benzoic acid methyl ester hydrogen chloride, 4-{2-cyclohexyl-2-[2-(4-methoxycarbonyl-phenyl)-benzoimidazol-1-yl]-acetylamino}-piperidine-1-carboxylic acid ethyl ester hydrogen chloride,
N-cyclohexyl-2-[2-(2,4-dimethoxy-phenyl)-benzoimidazol-1-yl]-2-phenyl-acetamide hydrogen chloride,
4-(1-{cyclohexyl-[3-(2-oxo-pyrrolidin-1-yl)-propylcarbamoyl]-methyl}-1H-benzoimidazol-2-yl)-benzoic acid methyl ester hydrogen chloride,
4-{1-[cyclohexyl-(3-methoxycarbonyl-propylcarbamoyl)-methyl]-1H-benzoimidazol-2-yl}-benzoic acid methyl ester hydrogen chloride,
4-{1-[cyclohexyl-(4-methoxycarbonyl-butyl carbamoyl)-methyl]-1H-benzoimidazol-2-yl}-benzoic acid methyl ester hydrogen chloride,
4-{1-[cyclohexyl-(5-methoxycarbonyl-pentylcarbamoyl)-methyl]-1H-benzoimidazol-2-yl}-benzoic acid methyl ester hydrogen chloride,
2-cyclohexyl-2-[2-(2,4-dimethoxy-phenyl)-benzoimidazol-1-yl]-N-methyl-acetamide hydrogen chloride,
2-[2-(4-Acetylamino-phenyl)-benzoimidazol-1-yl]-2,N-dicyclohexyl-acetamide,
2-[2-(3-acetylamino-phenyl)-benzoimidazol-1-yl]-2,N-dicyclohexyl-acetamide,
4-{1-[cyclohexyl-(3-formylamino-phenylcarbamoyl)-methyl]-1H-benzoimidazol-2-yl}-benzoic acid methyl ester hydrogen chloride,
N-cyclopentyl-2-(2-naphthalen-1-yl-benzoimidazol-1-yl)-propionamide,
2,N-Dicyclohexyl-2-(2-phenyl-benzoimidazol-1-yl)-acetamide,
2-[1-(Cyclohexyl-cyclohexylcarbamoyl-methyl)-1H-benzoimidazol-2-yl]-benzamide,
2-[2-(5-Amino-pyridin-2-yl)-benzoimidazol-1-yl]-2,N-dicyclohexyl-acetamide,
2,N-Dicyclohexyl-2-[2-(2-ethyl-5-methyl-2H-pyrazol-3-yl)-benzoimidazol-1-yl]-acetamide,
2,N-Dicyclohexyl-2-[2-(5-methyl-isoxazol-4-yl)-benzoimidazol-1-yl]-acetamide,
2,N-Dicyclohexyl-2-[2-(1H-pyrrol-2-yl)-benzoimidazol-1-yl]-acetamide,
2,N-Dicyclohexyl-2-(2-furan-2-yl-benzoimidazol-1-yl)-acetamide,
2-[6-Bromo-2-(4-chloro-phenyl)-benzoimidazol-1-yl]-2,N-dicyclohexyl-acetamide,
2-[6-Chloro-2-(4-chloro-phenyl)-benzoimidazol-1-yl]-2,N-dicyclohexyl-acetamide,
2-[2-(4-Chloro-phenyl)-6-methoxy-benzoimidazol-1-yl]-2,N-dicyclohexyl-acetamide,
[6-Chloro-2-(4-chloro-phenyl)-5-fluoro-benzoimidazol-1-yl]-2,N-dicyclohexyl-acetamide,
(S)-2,N-Dicyclohexyl-2-[2-(2,4-dimethoxy-phenyl)-benzoimidazol-1-yl]-acetamide,
(S)-2-[2-(4-Chloro-phenyl)-benzoimidazol-1-yl]-2,N-dicyclohexyl-acetamide,
2-[1-(Cyclohexyl-cyclohexylcarbamoyl-methyl)-1H-benzoimidazol-2-yl]-N-methyl-benzamide,
2,N-Dicyclohexyl-2-(2-furan-3-yl-benzoimidazol-1-yl)-acetamide,
2,N-Dicyclohexyl-2-[2-(3-methyl-furan-2-yl)-benzoimidazol-1-yl]-acetamide, 2,N-Dicyclohexyl-2-[2-(3-methyl-isoxazol-5-yl)-benzoimidazol-1-yl]-acetamide, 2,N-Dicyclohexyl-2-(2-m-tolyl-benzoimidazol-1-yl)-acetamide,
2,N-Dicyclohexyl-2-[2-(3-fluoro-phenyl)-benzoimidazol-1-yl]-acetamide,
2,N-Dicyclohexyl-2-[2-(2-fluoro-phenyl)-benzoimidazol-1-yl]-acetamide,
2,N-Dicyclohexyl-2-[2-(3,5-dimethyl-isoxazol-4-yl)-benzoimidazol-1-yl]-acetamide,
2,N-Dicyclohexyl-2-[2-(3-methyl-thiophen-2-yl)-benzoimidazol-1-yl]-acetamide,
2,N-Dicyclohexyl-2-[2-(4-vinyl-phenyl)-benzoimidazol-1-yl]-acetamide,
2,N-Dicyclohexyl-2-[2-(2,3-dimethyl-phenyl)-benzoimidazol-1-yl]-acetamide,
2,N-Dicyclohexyl-2-[2-(3,4-dimethyl-phenyl)-benzoimidazol-1-yl]-acetamide,
2,N-Dicyclohexyl-2-[2-(4-ethyl-phenyl)-benzoimidazol-1-yl]-acetamide,
2,N-Dicyclohexyl-2-[2-(2,4-dimethyl-phenyl)-benzoimidazol-1-yl]-acetamide,
2,N-Dicyclohexyl-2-[2-(2-ethyl-phenyl)-benzoimidazol-1-yl]-acetamide,
2,N-Dicyclohexyl-2-[2-(4-fluoro-3-methyl-phenyl)-benzoimidazol-1-yl]-acetamide,
2,N-Dicyclohexyl-2-[2-(3-fluoro-4-methyl-phenyl)-benzoimidazol-1-yl]-acetamide,
2,N-Dicyclohexyl-2-[2-(2,6-difluoro-phenyl)-benzoimidazol-1-yl]-acetamide,
2,N-Dicyclohexyl-2-[2-(3,5-difluoro-phenyl)-benzoimidazol-1-yl]-acetamide,
2,N-Dicyclohexyl-2-[2-(2,5-difluoro-phenyl)-benzoimidazol-1-yl]-acetamide,
2,N-Dicyclohexyl-2-[2-(3,4-difluoro-phenyl)-benzoimidazol-1-yl]-acetamide,
2,N-Dicyclohexyl-2-[2-(2,3-difluoro-phenyl)-benzoimidazol-1-yl]-acetamide,
2,N-Dicyclohexyl-2-[2-(1H-indol-4-yl)-benzoimidazol-1-yl]-acetamide,
2,N-Dicyclohexyl-2-[2-(1H-indol-6-yl)-benzoimidazol-1-yl]-acetamide,
2-[2-(5-Chloro-thiophen-2-yl)-benzoimidazol-1-yl]-2,N-dicyclohexyl-acetamide,
2-[2-(4-Acetyl-phenyl)-benzoimidazol-1-yl]-2,N-dicyclohexyl-acetamide,
2-[2-(2-Acetyl-phenyl)-benzoimidazol-1-yl]-2,N-dicyclohexyl-acetamide,
2,N-Dicyclohexyl-2-[2-(4-isopropyl-phenyl)-benzoimidazol-1-yl]-acetamide,
2-[2-(4-Cyano-2-fluoro-phenyl)-benzoimidazol-1-yl]-2,N-dicyclohexyl-acetamide,
2,N-Dicyclohexyl-2-[2-(2-dimethylamino-phenyl)-benzoimidazol-1-yl]-acetamide,
2,N-Dicyclohexyl-2-[2-(3-dimethylamino-phenyl)-benzoimidazol-1-yl]-acetamide,
2,N-Dicyclohexyl-2-[2-(4-methoxy-3-methyl-phenyl)-benzoimidazol-1-yl]-acetamide,
2,N-Dicyclohexyl-2-[2-(4-methoxy-2-methyl-phenyl)-benzoimidazol-1-yl]-acetamide,
2,N-Dicyclohexyl-2-[2-(3-methoxy-4-methyl-phenyl)-benzoimidazol-1-yl]-acetamide,
2,N-Dicyclohexyl-2-[2-(2-ethoxy-phenyl)-benzoimidazol-1-yl]-acetamide,
2-[2-(6-Chloro-pyridin-3-yl)-benzoimidazol-1-yl]-2,N-dicyclohexyl-acetamide,
2-[2-(2-Chloro-pyridin-4-yl)-benzoimidazol-1-yl]-2,N-dicyclohexyl-acetamide,
2-[2-(4-Chloro-phenyl)-6-fluoro-benzoimidazol-1-yl]-2,N-dicyclohexyl-acetamide,
2,N-Dicyclohexyl-2-[2-(3-fluoro-4-methoxy-phenyl)-benzoimidazol-1-yl]-acetamide,
2-[2-(4-Chloro-3-methyl-phenyl)-benzoimidazol-1-yl]-2,N-dicyclohexyl-acetamide, 2-[2-(3-Chloro-2-methyl-phenyl)-benzoimidazol-1-yl]-2,N-dicyclohexyl-acetamide,
2-[2-(4-Chloro-3-fluoro-phenyl)-benzoimidazol-1-yl]-2,N-dicyclohexyl-acetamide,
2-[2-(3-Chloro-4-fluoro-phenyl)-benzoimidazol-1-yl]-2,N-dicyclohexyl-acetamide,
2,N-Dicyclohexyl-2-[2-(5-methyl-1H-indol-2-yl)-benzoimidazol-1-yl]-acetamide,
2,N-Dicyclohexyl-2-[2-(2,3,4-trifluoro-phenyl)-benzoimidazol-1-yl]-acetamide,
2,N-Dicyclohexyl-2-[2-(2,4,5-trifluoro-phenyl)-benzoimidazol-1-yl]-acetamide,
2-(2-Benzo[b]thiophen-2-yl-benzoimidazol-1-yl)-2,N-dicyclohexyl-acetamide,
2,N-Dicyclohexyl-2-[2-(5-fluoro-1H-indol-2-yl)-benzoimidazol-1-yl]-acetamide,
2-(2-Benzothiazol-6-yl-benzoimidazol-1-yl)-2,N-dicyclohexyl-acetamide,
2,N-Dicyclohexyl-2-[2-(4-isopropoxy-phenyl)-benzoimidazol-1-yl]-acetamide,
2,N-Dicyclohexyl-2-[2-(3,4-dimethoxy-phenyl)-benzoimidazol-1-yl]-acetamide,
2,N-Dicyclohexyl-2-[2-(2,5-dimethoxy-phenyl)-benzoimidazol-1-yl]-acetamide,
2,N-Dicyclohexyl-2-[2-(2-difluoromethoxy-phenyl)-benzoimidazol-1-yl]-acetamide,
2,N-Dicyclohexyl-2-[2-(4-difluoromethoxy-phenyl)-benzoimidazol-1-yl]-acetamide,
2,N-Dicyclohexyl-2-[2-(3-difluoromethoxy-phenyl)-benzoimidazol-1-yl]-acetamide,
2,N-Dicyclohexyl-2-[2-(4-trifluoromethyl-phenyl)-benzoimidazol-1-yl]-acetamide,
2,N-Dicyclohexyl-2-[2-(3,4-dichloro-phenyl)-benzoimidazol-1-yl]-acetamide,
2-[2-(4-Bromo-phenyl)-benzoimidazol-1-yl]-2,N-dicyclohexyl-acetamide,
2,N-Dicyclohexyl-2-[2-(6-methoxy-naphthalen-2-yl)-benzoimidazol-1-yl]-acetamide,
2,N-Dicyclohexyl-2-[2-(3-trifluoromethoxy-phenyl)-benzoimidazol-1-yl]-acetamide,
2,N-Dicyclohexyl-2-[2-(7-ethoxy-benzofuran-2-yl)-benzoimidazol-1-yl]-acetamide,
2,N-Dicyclohexyl-2-[2-(3-fluoro-4-trifluoromethyl-phenyl)-benzoimidazol-1-yl]-acetamide,
2,N-Dicyclohexyl-2-[2-(6-diethylamino-pyridin-3-yl)-benzoimidazol-1-yl]-acetamide,
2-[2-(2-Chloro-5-methyl-phenyl)-benzoimidazol-1-yl]-2,N-dicyclohexyl-acetamide, 2-[2-(5-Chloro-2-methyl-phenyl)-benzoimidazol-1-yl]-2,N-dicyclohexyl-acetamide,
2-[2-(2-Chloro-6-methyl-phenyl)-benzoimidazol-1-yl]-2,N-dicyclohexyl-acetamide,
2,N-Dicyclohexyl-2-(2-quinoxalin-6-yl-benzoimidazol-1-yl)-acetamide,
2-[2-(5-Chloro-2-fluoro-phenyl)-benzoimidazol-1-yl]-2,N-dicyclohexyl-acetamide,
2,N-Dicyclohexyl-2-[2-(4-methoxy-3,5-dimethyl-phenyl)-benzoimidazol-1-yl]-acetamide,
2,N-Dicyclohexyl-2-[2-(2,3-dimethoxy-phenyl)-benzoimidazol-1-yl]-acetamide,
2-[2-(3-Chloro-4-methoxy-phenyl)-benzoimidazol-1-yl]-2,N-dicyclohexyl-acetamide,
2,N-Dicyclohexyl-2-[2-(2,5-dichloro-phenyl)-benzoimidazol-1-yl]-acetamide,
2-[2-(3-Chloro-2,4-difluoro-phenyl)-benzoimidazol-1-yl]-2,N-dicyclohexyl-acetamide,
2-[2-(2-Chloro-4,5-difluoro-phenyl)-benzoimidazol-1-yl]-2,N-dicyclohexyl-acetamide,
2,N-Dicyclohexyl-2-[2-(4-diethylamino-phenyl)-benzoimidazol-1-yl]-acetamide,
2-[2-(4-Benzoyl-phenyl)-benzoimidazol-1-yl]-2,N-dicyclohexyl-acetamide,
(S)-2-[2-(4-Cyano-phenyl)-benzoimidazol-1-yl]-2,N-dicyclohexyl-acetamide,
2,N-Dicyclohexyl-2-[2-(4-phenoxy-phenyl)-benzoimidazol-1-yl]-acetamide,
2,N-Dicyclohexyl-2-[2-(2-phenoxy-phenyl)-benzoimidazol-1-yl]-acetamide,
2,N-Dicyclohexyl-2-[2-(3-phenoxy-phenyl)-benzoimidazol-1-yl]-acetamide,
2,N-Dicyclohexyl-2-{2-[2-(1,1,2,2-tetrafluoro-ethoxy)-phenyl]-benzoimidazol-1-yl}-acetamide,
2,N-Dicyclohexyl-2-{2-[3-(1,1,2,2-tetrafluoro-ethoxy)-phenyl]-benzoimidazol-1-yl}-acetamide,
2,N-Dicyclohexyl-2-{2-[4-(1,1,2,2-tetrafluoro-ethoxy)-phenyl]-benzoimidazol-1-yl}-acetamide,
2,N-Dicyclohexyl-2-[2-(4'-trifluoromethyl-biphenyl-4-yl)-benzoimidazol-1-yl]-acetamide,
2,N-Dicyclohexyl-2-[2-(3',4'-dichloro-biphenyl-4-yl)-benzoimidazol-1-yl]-acetamide,
2,N-Dicyclohexyl-2-[2-(2,4-dichloro-5-sulfamoyl-phenyl)-benzoimidazol-1-yl]-acetamide,
(S)-2-[6-Chloro-2-(4-chloro-phenyl)-5-fluoro-benzoimidazol-1-yl]-2,N-dicyclohexyl-acetamide,
2,N-Dicyclohexyl-2-(2-pyridin-2-yl-benzoimidazol-1-yl)-acetamide,
2,N-Dicyclohexyl-2-[2-(6-methyl-pyridin-3-yl)-benzoimidazol-1-yl]-acetamide,
2,N-Dicyclohexyl-2-[2-(3-methyl-pyridin-2-yl)-benzoimidazol-1-yl]-acetamide,
2,N-Dicyclohexyl-2-[2-(6-methyl-pyridin-2-yl)-benzoimidazol-1-yl]-acetamide,
2-[2-(2-Amino-pyridin-3-yl)-benzoimidazol-1-yl]-2,N-dicyclohexyl-acetamide,
2-[2-(6-Cyano-pyridin-3-yl)-benzoimidazol-1-yl]-2,N-dicyclohexyl-acetamide,
2,N-Dicyclohexyl-2-[2-(2-methoxy-pyridin-3-yl)-benzoimidazol-1-yl]-acetamide,
2-[2-(2-Chloro-6-methyl-pyridin-3-yl)-benzoimidazol-1-yl]-2,N-dicyclohexyl-acetamide,
2-[2-(2-Chloro-6-methyl-pyridin-4-yl)-benzoimidazol-1-yl]-2,N-dicyclohexyl-acetamide,
2,N-Dicyclohexyl-2-(2-quinolin-3-yl-benzoimidazol-1-yl)-acetamide,
2,N-Dicyclohexyl-2-(2-quinolin-4-yl-benzoimidazol-1-yl)-acetamide,
2-[2-(3-Chloro-4-trifluoromethyl-phenyl)-benzoimidazol-1-yl]-2,N-dicyclohexyl-acetamide,
(S)-2-[2-(4-Chloro-phenyl)-benzoimidazol-1-yl]-4-methyl-pentanoic acid cyclohexylamide,
2-(4-Chloro-phenyl)-2-[2-(4-chloro-phenyl)-benzoimidazol-1-yl]-N-cyclohexyl-acetamide,
2-[2-(4-Chloro-phenyl)-benzoimidazol-1-yl]-N-cyclohexyl-2-(4-trifluoromethyl-phenyl)-acetamide,
2-[2-(4-Chloro-phenyl)-benzoimidazol-1-yl]-N-cyclohexyl-2-(3,4-dichloro-phenyl)-acetamide,
2-[2-(4-Chloro-phenyl)-benzoimidazol-1-yl]-N-cyclohexyl-2-(3-methoxy-phenyl)-acetamide,
2-[2-(4-Chloro-phenyl)-benzoimidazol-1-yl]-N-cyclohexyl-2-p-tolyl-acetamide,
2-[2-(4-Chloro-phenyl)-benzoimidazol-1-yl]-N-cyclohexyl-2-(3-fluoro-phenyl)-acetamide,
2-[2-(4-Chloro-phenyl)-benzoimidazol-1-yl]-N-cyclohexyl-2-(4-difluoromethoxy-phenyl)-acetamide, 2-[2-(4-Chloro-phenyl)-benzoimidazol-1-yl]-N-cyclohexyl-2-(2,5-difluoro-phenyl)-acetamide,
2-[2-(4-Chloro-phenyl)-benzoimidazol-1-yl]-N-cyclohexyl-2-(2-fluoro-5-methoxy-phenyl)-acetamide,
(S)-2-[2-(5-Chloro-2-fluoro-phenyl)-benzoimidazol-1-yl]-2,N-dicyclohexyl-acetamide,
(S)-2,N-Dicyclohexyl-2-[2-(2,3-dimethoxy-phenyl)-benzoimidazol-1-yl]-acetamide,
(S)-2-[2-(3-Chloro-4-methoxy-phenyl)-benzoimidazol-1-yl]-2,N-dicyclohexyl-acetamide,
(S)-2-Cyclohexyl-2-[2-(2,4-dimethoxy-phenyl)-benzoimidazol-1-yl]-N-(2,6-dimethyl-phenyl)-acetamide,
2-[2-(4-Chloro-phenyl)-benzoimidazol-1-yl]-2-cyclohexyl-N-(4,4-difluoro-cyclohexyl)-acetamide,
(S)-2-[2-(4-Chloro-phenyl)-benzoimidazol-1-yl]-2-cyclohexyl-N-(4,4-difluoro-cyclohexyl)-acetamide,
(S)-2-[2-(2-Amino-pyridin-3-yl)-benzoimidazol-1-yl]-2,N-dicyclohexyl-acetamide,
2,N-Dicyclohexyl-2-(6-fluoro-2-pyridin-2-yl-benzoimidazol-1-yl)-acetamide,
2,N-Dicyclohexyl-2-[2-(2,4-dimethoxy-phenyl)-6-fluoro-benzoimidazol-1-yl]-acetamide,
2,N-Dicyclohexyl-2-[6-fluoro-2-(4-methoxy-phenyl)-benzoimidazol-1-yl]-acetamide,
2,N-Dicyclohexyl-2-[2-(2,3-difluoro-phenyl)-6-fluoro-benzoimidazol-1-yl]-acetamide,
2,N-Dicyclohexyl-2-[2-(2,3-dimethoxy-phenyl)-6-fluoro-benzoimidazol-1-yl]-acetamide, 2,N-Dicyclohexyl-2-[2-(2-ethyl-5-methyl-2H-pyrazol-3-yl)-6-fluoro-benzoimidazol-1-yl]-acetamide,
2,N-Dicyclohexyl-2-[2-(3,5-dimethyl-isoxazol-4-yl)-6-fluoro-benzoimidazol-1-yl]-acetamide,
2,N-Dicyclohexyl-2-[6-fluoro-2-(1H-pyrazol-4-yl)-benzoimidazol-1-yl]-acetamide,
2,N-Dicyclohexyl-2-[2-(1,5-dimethyl-1H-pyrazol-3-yl)-6-fluoro-benzoimidazol-1-yl]-acetamide,
2,N-Dicyclohexyl-2-[6-fluoro-2-(3-methyl-isoxazol-5-yl)-benzoimidazol-1-yl]-acetamide,
2,N-Dicyclohexyl-2-[6-fluoro-2-(1H-pyrrol-2-yl)-benzoimidazol-1-yl]-acetamide, 2,N-Dicyclohexyl-2-[6-fluoro-2-(3-methyl-thiophen-2-yl)-benzoimidazol-1-yl]-acetamide,
N-Benzyl-2-[2-(4-chloro-phenyl)-benzoimidazol-1-yl]-2-cyclohexyl-acetamide,
N-Butyl-2-[2-(4-chloro-phenyl)-benzoimidazol-1-yl]-2-cyclohexyl-acetamide,
2-[2-(4-Chloro-phenyl)-benzoimidazol-1-yl]-N-cyclohexyl-2-(tetrahydro-pyran-4-yl)-acetamide,
2-[5-Chloro-2-(4-chloro-phenyl)-6-fluoro-benzoimidazol-1-yl]-2,N-dicyclohexyl-acetamide,
2-[2-(4-Chloro-phenyl)-5,6-difluoro-benzoimidazol-1-yl]-2,N-dicyclohexyl-acetamide,
2-[2-(4-Chloro-phenyl)-benzoimidazol-1-yl]-2-cyclohexyl-N-(tetrahydro-pyran-4-yl)-acetamide,
2-[2-(4-Chloro-phenyl)-benzoimidazol-1-yl]-2-cyclohexyl-N-cyclopropyl-acetamide,
2,N-Dicyclohexyl-2-[2-(6-morpholin-4-yl-pyridin-3-yl)-benzoimidazol-1-yl]-acetamide,
(S)-2-[2-(4-Chloro-phenyl)-benzoimidazol-1-yl]-2-cyclohexyl-N-(tetrahydro-pyran-4-yl)-acetamide,
(S)-2,N-Dicyclohexyl-2-[2-(4-methanesulfonyl-phenyl)-benzoimidazol-1-yl]-acetamide,
(S)-2-[2-(4-Chloro-phenyl)-benzoimidazol-1-yl]-2-cyclohexyl-N-cyclopropyl-acetamide,
2-[6-Chloro-2-(4-chloro-phenyl)-5-fluoro-benzoimidazol-1-yl]-N-cyclohexyl-2-(tetrahydro-pyran-4-yl)-acetamide,
(S)-2-[2-(4-Chloro-phenyl)-benzoimidazol-1-yl]-N-cyclohexyl-2-(tetrahydro-pyran-4-yl)-acetamide,
(S)-2-[6-Chloro-2-(4-chloro-phenyl)-5-fluoro-benzoimidazol-1-yl]-N-cyclohexyl-2-(tetrahydro-pyran-4-yl)-acetamide,
(S)-2-[2-(4-Chloro-phenyl)-5,6-difluoro-benzoimidazol-1-yl]-2,N-dicyclohexyl-acetamide,
(S)-2-[2-(5-Chloro-thiophen-2-yl)-benzoimidazol-1-yl]-2,N-dicyclohexyl-acetamide,
(S)-2,N-Dicyclohexyl-2-[2-(2,3-difluoro-phenyl)-6-fluoro-benzoimidazol-1-yl]-acetamide,
2-[6-Chloro-2-(4-chloro-phenyl)-5-fluoro-benzoimidazol-1-yl]-N-cyclohexyl-2-cyclopentyl-acetamide,
(S)-2-[6-Chloro-2-(4-chloro-phenyl)-5-fluoro-benzoimidazol-1-yl]-heptanoic acid cyclohexylamide,
(S)-2-[6-Chloro-2-(4-chloro-phenyl)-5-fluoro-benzoimidazol-1-yl]-N-cyclohexyl-2-cyclopentyl-acetamide,
2-[2-(4-Chloro-phenyl)-5-fluoro-benzoimidazol-1-yl]-2,N-dicyclohexyl-acetamide,
2-[1-(Cyclohexyl-cyclohexylcarbamoyl-methyl)-5,6-difluoro-1H-benzoimidazol-2-yl]-benzoic acid methyl ester,
2,N-Dicyclohexyl-2-(5,6-difluoro-2-pyridin-2-yl-benzoimidazol-1-yl)-acetamide,
2-[2-(5-Chloro-thiophen-2-yl)-5,6-difluoro-benzoimidazol-1-yl]-2,N-dicyclohexyl-acetamide,
2-[6-Chloro-1-(cyclohexyl-cyclohexylcarbamoyl-methyl)-5-fluoro-1H-benzoimidazol-2-yl]-benzoic acid methyl ester,
2-(6-Chloro-5-fluoro-2-pyridin-2-yl-benzoimidazol-1-yl)-2,N-dicyclohexyl-acetamide,
2-(6-Chloro-5-fluoro-2-pyridin-3-yl-benzoimidazol-1-yl)-2,N-dicyclohexyl-acetamide,
2-(6-Chloro-5-fluoro-2-pyridin-4-yl-benzoimidazol-1-yl)-2,N-dicyclohexyl-acetamide,
2-[6-Chloro-2-(3-chloro-thiophen-2-yl)-5-fluoro-benzoimidazol-1-yl]-2,N-dicyclohexyl-acetamide,
2-[6-Chloro-2-(5-chloro-thiophen-2-yl)-5-fluoro-benzoimidazol-1-yl]-2,N-dicyclohexyl-acetamide,
(S)-2-[6-Chloro-2-(4-chloro-phenyl)-5-fluoro-benzoimidazol-1-yl]-3-ethyl-pentanoic acid cyclohexylamide,
2-[6-Chloro-5-fluoro-2-(4-fluoro-phenyl)-benzoimidazol-1-yl]-2,N-dicyclohexyl-acetamide,
2-[2-(4-Chloro-phenyl)-benzoimidazol-1-yl]-2-cyclohexyl-N-(1-isopropyl-2-methyl-propyl)-acetamide,
2-[6-Chloro-2-(4-chloro-phenyl)-5-fluoro-benzoimidazol-1-yl]-2-cyclohexyl-N-cyclopentyl-acetamide,
2-[2-(4-Chloro-phenyl)-5,6-difluoro-benzoimidazol-1-yl]-N-cyclohexyl-2-(tetrahydro-pyran-4-yl)-acetamide,
(S)-2-[2-(4-Chloro-phenyl)-5-fluoro-benzoimidazol-1-yl]-2,N-dicyclohexyl-acetamide,
2-[2-(4-Chloro-phenyl)-5,6-difluoro-benzoimidazol-1-yl]-2-cyclohexyl-N-(tetrahydro-pyran-4-yl)-acetamide,
2-[6-Chloro-2-(4-chloro-phenyl)-5-fluoro-benzoimidazol-1-yl]-2-cyclohexyl-N-(tetrahydro-pyran-4-yl)-acetamide,
2,N-Dicyclohexyl-2-[2-(3-dimethylamino-phenyl)-5,6-difluoro-benzoimidazol-1-yl]-acetamide,
2,N-Dicyclohexyl-2-[2-(3-dimethylamino-phenyl)-6-fluoro-benzoimidazol-1-yl]-acetamide,
2-[2-(4-Chloro-phenyl)-5,6-difluoro-benzoimidazol-1-yl]-2-cyclohexyl-N-(1-isopropyl-2-methyl-propyl)-acetamide, 2-[6-Chloro-2-(4-chloro-phenyl)-5-fluoro-benzoimidazol-1-yl]-2-cyclohexyl-N-(1-isopropyl-2-methyl-propyl)-acetamide,
2-[2-(3-Chloro-phenyl)-5,6-difluoro-benzoimidazol-1-yl]-2,N-dicyclohexyl-acetamide,
2-[2-(2-Chloro-phenyl)-5,6-difluoro-benzoimidazol-1-yl]-2,N-dicyclohexyl-acetamide, (S)-2-[6-Chloro-5-fluoro-2-(4-fluoro-phenyl)-benzoimidazol-1-yl]-2,N-dicyclohexyl-acetamide,
(S)-2-[2-(4-Chloro-phenyl)-5,6-difluoro-benzoimidazol-1-yl]-N-cyclohexyl-2-(tetrahydro-pyran-4-yl)-acetamide,
2-[2-(4-Chloro-phenyl)-5-fluoro-benzoimidazol-1-yl]-N-cyclohexyl-2-(tetrahydro-pyran-4-yl)-acetamide,
2-[2-(4-Chloro-phenyl)-6-fluoro-benzoimidazol-1-yl]-N-cyclohexyl-2-(tetrahydro-pyran-4-yl)-acetamide,
2-[2-(4-Chloro-phenyl)-6-fluoro-benzoimidazol-1-yl]-N-cyclohexyl-2-(tetrahydro-pyran-2-yl)-acetamide,
2-[6-Chloro-2-(4-chloro-phenyl)-5-fluoro-benzoimidazol-1-yl]-N-cyclohexyl-2-(tetrahydro-pyran-2-yl)-acetamide,
(S)-2,N-Dicyclohexyl-2-[6-fluoro-2-(3-methyl-thiophen-2-yl)-benzoimidazol-1-yl]-acetamide,
(S)-2-[2-(2-Chloro-phenyl)-5,6-difluoro-benzoimidazol-1-yl]-2,N-dicyclohexyl-acetamide,
(S)-2-[2-(4-Chloro-phenyl)-5-fluoro-benzoimidazol-1-yl]-N-cyclohexyl-2-(tetrahydro-pyran-4-yl)-acetamide,
(S)-2-[2-(4-Chloro-phenyl)-6-fluoro-benzoimidazol-1-yl]-N-cyclohexyl-2-(tetrahydro-pyran-4-yl)-acetamide,
(S)-2-[2-(4-Chloro-phenyl)-6-fluoro-benzoimidazol-1-yl]-N-cyclohexyl-2-(R)-tetrahydro-pyran-2-yl-acetamide,
(S)-2-[2-(4-Chloro-phenyl)-6-fluoro-benzoimidazol-1-yl]-N-cyclohexyl-2-(S)-tetrahydro-pyran-2-yl-acetamide,
2-[2-(4-Chloro-phenyl)-5-fluoro-benzoimidazol-1-yl]-N-cyclohexyl-2-(tetrahydro-pyran-2-yl)-acetamide,
2,N-Dicyclohexyl-2-[2-(3,4-dichloro-phenyl)-6-methoxy-benzoimidazol-1-yl]-acetamide,
2-[2-(4-Chloro-phenyl)-6-methoxy-benzoimidazol-1-yl]-2,N-dicyclohexyl-acetamide,
2-[2-(5-Chloro-thiophen-2-yl)-6-methoxy-benzoimidazol-1-yl]-2,N-dicyclohexyl-acetamide,
2-[2-(3-Chloro-4-methoxy-phenyl)-6-methoxy-benzoimidazol-1-yl]-2,N-dicyclohexyl-acetamide,
2-[2-(4-Chloro-3-fluoro-phenyl)-6-methoxy-benzoimidazol-1-yl]-2,N-dicyclohexyl-acetamide,
2-Cyclohexyl-N-cyclopentyl-2-[2-(3,4-dichloro-phenyl)-6-methoxy-benzoimidazol-1-yl]-acetamide,
2-[2-(4-Chloro-phenyl)-6-methoxy-benzoimidazol-1-yl]-2-cyclohexyl-N-cyclopentyl-acetamide,
2-[2-(3-Chloro-phenyl)-6-methoxy-benzoimidazol-1-yl]-2,N-dicyclohexyl-acetamide,
2,N-Dicyclopentyl-2-[2-(3,4-dichloro-phenyl)-6-methoxy-benzoimidazol-1-yl]-acetamide,
2-[2-(4-Chloro-phenyl)-6-methoxy-benzoimidazol-1-yl]-N-cyclohexyl-2-cyclopentyl-acetamide,
2-[2-(4-Chloro-3-fluoro-phenyl)-6-methoxy-benzoimidazol-1-yl]-2-cyclohexyl-N-cyclopentyl-acetamide,
2-[2-(3-Chloro-4-methoxy-phenyl)-6-methoxy-benzoimidazol-1-yl]-2-cyclohexyl-N-cyclopentyl-acetamide,
2,N-Dicyclohexyl-2-[2-(4-fluoro-phenyl)-6-methoxy-benzoimidazol-1-yl]-acetamide,
2-[2-(3-Chloro-phenyl)-6-methoxy-benzoimidazol-1-yl]-2-cyclohexyl-N-cyclopentyl-acetamide,
2-[2-(3-Chloro-4-methoxy-phenyl)-6-methoxy-benzoimidazol-1-yl]-N-cyclohexyl-2-cyclopentyl-acetamide,
2-[2-(5-Chloro-thiophen-2-yl)-6-methoxy-benzoimidazol-1-yl]-N-cyclohexyl-2-cyclopentyl-acetamide,
2-Cyclobutyl-N-cyclohexyl-2-[2-(3,4-dichloro-phenyl)-6-methoxy-benzoimidazol-1-yl]-acetamide,
2-[2-(5-Chloro-thiophen-2-yl)-6-methoxy-benzoimidazol-1-yl]-2-cyclohexyl-N-cyclopentyl-acetamide,
2-[2-(6-Chloro-pyridin-3-yl)-6-methoxy-benzoimidazol-1-yl]-2,N-dicyclohexyl-acetamide,
2-[2-(3-Chloro-phenyl)-6-methoxy-benzoimidazol-1-yl]-N-cyclohexyl-2-cyclopentyl-acetamide,
2-[2-(3-Chloro-4-methoxy-phenyl)-6-methoxy-benzoimidazol-1-yl]-2,N-dicyclopentyl-acetamide,
2,N-Dicyclohexyl-2-[6-methoxy-2-(6-trifluoromethyl-pyridin-3-yl)-benzoimidazol-1-yl]-acetamide,
2-[2-(5-Chloro-thiophen-2-yl)-6-methoxy-benzoimidazol-1-yl]-2-cyclobutyl-N-cyclohexyl-acetamide,
2-[2-(3-Chloro-phenyl)-6-methoxy-benzoimidazol-1-yl]-2-cyclobutyl-N-cyclohexyl-acetamide, and
N-Cyclohexyl-2-cyclopentyl-2-[2-(4-fluoro-phenyl)-6-methoxy-benzoimidazol-1-yl]-acetamide,
and pharmaceutically acceptable salts and esters thereof.

In some embodiments, the FXR agonist is selected from the group consisting of the compounds described in US2009215748, namely:

(3,4-difluoro-benzoyl)-4,4-dimethyl-5,6-dihydro-4H-thieno[2,3-d]azepine-8-carboxylic acid ethyl ester;
3-(3,4-difluorobenzoyl)-1,1,6-trimethyl-1,2,3,6-tetrahydroazepino[4,5-b]indole-5-carboxylic acid ethyl ester;
3-(3,4-difluoro-benzoyl)-1,1-dimethylene-1,2,3,6-tetrahydro-azepino[4,5-b]indole-5-carboxylic acid ethyl ester;
3-(3,4-difluoro-benzoyl)-1,1-dimethylene-1,2,3,6-tetrahydro-azepino[4,5-b]indole-5-carboxylic acid isopropyl ester;
3-(3,4-difluorobenzoyl)-1,1-tetramethylene-1,2,3,6-tetrahydroazepino[4,5-b]indole-5-carboxylic acid ethyl ester;
3-(3,4-difluoro-benzoyl)-1,1-trimethylene-1,2,3,6-tetrahydro-azepino[4,5-b]indole-5-carboxylic acid ethyl ester;
3-(3,4-difluorobenzoyl)-1-methyl-1,2,3,6-tetrahydroazepino[4,5-b]indole-5-carboxylic acid cyclobutylamide;
3-(3,4-difluorobenzoyl)-2-methyl-1,2,3,6-tetrahydroazepino[4,5-b]indole-5-carboxylic acid cyclobutylamide;
3-(3-fluorobenzoyl)-1,2,3,6-tetrahydroazepino[4,5-b]indole-5-carboxylic acid ethyl ester;
3-(4-fluoro-benzoyl)-1,1-dimethyl-1,2,3,4,5,6,7,8,9,10-decahydroazepino[4,5-b]indole-5-carboxylic acid ethyl ester;
3-(4-fluoro-benzoyl)-1,1-dimethyl-1,2,3,6,7,8,9,10-octahydro-azepino[4,5-b]indole-5-carboxylic acid ethyl ester;
3-(4-fluoro-benzoyl)-1,1-dimethyl-1,2,3,6-tetrahydro-azepino[4,5-b]indole-5-carboxylic acid isopropylamide;
3-(4-fluoro-benzoyl)-1,1-dimethyl-9-(3-methyl-butyryl amino)-1,2,3,6-tetrahydro-azepino[4,5-b]indole-5-carboxylic acid ethyl ester;
3-(4-fluoro-benzoyl)-1,1-dimethyl-9-phenyl acetyl amino-1,2,3,6-tetrahydro-azepino[4,5-b]indole-5-carboxylic acid ethyl ester;
3-(4-fluoro-benzoyl)-1,1-dimethyl-1,2,3,6,7,8,9,10-octahydro-azepino[4,5-b]indole-5-carboxylic acid ethyl ester;
3-(4-fluoro-benzoyl)-1,2,3,4,5,6,7,8,9,10-decahydro-azepino[4,5-b]indole-5-carboxylic acid ethyl ester;
3-(4-fluoro-benzoyl) 1,2,3,6,7,8,9,10-octahydro-azepino[4,5-b]indole-5-carboxylic acid ethyl ester;
3-(4-fluorobenzoyl)-1,2,3,6-tetrahydroazepino[4,5-b]indole-5-carboxylic acid cyclobutylamide;
3-(4-fluorobenzoyl)-2-methyl-1,2,3,6-tetrahydroazepino[4,5-b]indole-5-carboxylic acid cyclobutylamide;
6-(3,4-difluoro-benzoyl)-1,4,4-trimethyl-1,4,5,6-tetrahydro-pyrrolo[2,3-d]azepine-2,8-dicarboxylic acid 2-ethyl ester 8-isopropyl ester;
6-(3,4-difluoro-benzoyl)-4,4-dimethyl-1,4,5,6-tetrahydro-pyrrolo[2,3-d]azepine-2,8-dicarboxylic acid 2-ethyl ester 8-isopropyl ester;
6-(3,4-difluoro-benzoyl)-4,4-dimethyl-1,4,5,6-tetrahydro-pyrrolo[2,3-d]azepine-2,8-dicarboxylic acid dimethyl ester;
6-(3,4-difluoro-benzoyl)-4,4-dimethyl-1,4,5,6-tetrahydro-pyrrolo[2,3-d]azepine-2,8-dicarboxylic acid diethyl ester;

6-(3,4-difluoro-benzoyl)-4,4-dimethyl-5,6-dihydro-4H-thieno[2,3-d]azepine-8-carboxylic acid ethyl ester;
6-(3,4-difluoro-benzoyl)-5,6-dihydro-4H-thieno[2,3-D]azepine-8-carboxylic acid ethyl ester;
6-(4-fluoro-benzoyl)-3,6,7,8-tetrahydro-imidazo[4,5-D]azepine-4-carboxylic acid ethyl ester;
9-(1-benzyl-3,3-dimethyl-ureido)-3-(4-fluoro-benzoyl)-1,1-dimethyl-1,2,3,6-tetrahydro-azepino[4,5-b]indole-5-carboxylic acid ethyl ester;
9-(2,2-dimethyl-propionylamino)-3-(4-fluoro-benzoyl)-1,1-dimethyl-1,2,3,6-tetrahydro-azepino[4,5-b]indole-5-carboxylic acid ethyl ester;
9-(acetyl-methyl-amino)-3-(4-fluoro-benzoyl)-1,1-dimethyl-1,2,3,6-tetrahydro-azepino[4,5-b]indole-5-carboxylic acid ethyl ester;
9-[benzyl-(2-thiophen-2-yl-acetyl)-amino]-3-(4-fluoro-benzoyl)-1,1-dimethyl-1,2,3,6-tetrahydro-azepino[4,5-b]indole-5-carboxylic acid ethyl ester;
9-dimethylamino-3-(4-fluorobenzoyl)-1,1-dimethyl-1,2,3,6-tetrahydroazepino[4,5-b]indole-5-carboxylic acid ethyl ester;
9-fluoro-3-(3,4-difluoro-benzoyl)-1,1-dimethyl-1,2,3,6-tetrahydro-azepino[4,5-b]indole-5-carboxylic acid ethyl ester;
9-fluoro-3-(3,4-difluoro-benzoyl)-1,1-dimethyl-1,2,3,6-tetrahydro-azepino[4,5-b]indole-5-carboxylic acid isopropylamide;
9-fluoro-3-(4-fluoro-benzoyl)-1,1-dimethyl-1,2,3,6-tetrahydro-azepino[4,5-b]indole-5-carboxylic acid ethyl ester;
9-fluoro-3-(4-fluoro-benzoyl)-1,1-dimethyl-1,2,3,6-tetrahydro-azepino[4,5-b]indole-5-carboxylic acid isopropyl ester;
9-fluoro-3-cyclohexanecarbonyl-1,1-dimethyl-1,2,3,6-tetrahydro-azepino[4,5-b]indole-5-carboxylic acid ethyl ester;
cyclobutyl 3-(3,4-difluorobenzoyl)-1,1-dimethyl-1,2,3,6-tetrahydroazepino[4,5-b]indole-5-carboxamide;
diethyl 3-(4-fluorobenzoyl-1,2,3,6-tetrahydroazepino[4,5-b]indole-2,5-dicarboxylate;
ethyl 1,1-dimethyl-1,2,3,6-tetrahydro-azepino[4,5-b]indole5-carboxylate;
ethyl 1,1-dimethyl-3-(4-fluorobenzoyl)-1,2,3,6-tetrahydroazepino[4,5-b]indole-5-carboxylate;
ethyl 3-(3,4-difluorobenzoyl)-1,1-dimethyl-1,2,3,6-tetrahydroazepino[4,5-b]indole-5-carboxylate;
ethyl 3-(3,4-difluorobenzoyl)-1-methyl-1,2,3,6-tetrahydroazepino[4,5-b]indole-5-carboxylate;
ethyl 3-(4-chlorobenzoyl)-1,1-dimethyl-1,2,3,6-tetrahydroazepino[4,5-b]indole-5-carboxylate;
ethyl 3-(4-chlorobenzoyl)-1-methyl-1,2,3,6-tetrahydroazepino[4,5-b]indole-5-carboxylate;
ethyl 3-(4-fluorobenzoyl)-1,2,3,6-tetrahydroazepino[4,5-b]indole-5-carboxylate;
ethyl 3-(4-fluorobenzoyl)-1-methyl-1,2,3,6-tetrahydro-azepino[4,5-b]indole-5-carboxylate;
isopropyl 3-(3,4-difluorobenzoyl)-1,1-dimethyl-1,2,3,6-tetrahydroazepino[4,5-b]indole-5-carboxylate;
isopropyl 3-(3,4-difluorobenzoyl)-1-methyl-1,2,3,6-tetrahydroazepino[4,5-b]indole-5-carboxylate;
n-propyl 3(4-fluorobenzoyl)-2-methyl-1,2,3,6-tetrahydroazepino[4,5-b]indole-5-carboxylate; and
n-propyl 3(4-fluorobenzoyl)-2-methyl-8-fluoro-1,2,3,6-tetrahydroazepino[4,5-b]indole-5-carboxylate.

In some embodiments, the FXR agonist is selected from the group consisting of the compounds disclosed in WO2013037482, namely:

4-(((6-((5-cyclopropyl-3-(2,6-dichlorophenyl)isoxazol-4-yl)methoxy)-2-(trifluoromethyl)pyridin-3-yl)(methyl)amino)methyl)benzoic acid;
3-(2-(2-chloro-4-((5-cyclopropyl-3-(2,6-dichlorophenyl)isoxazol-4-yl)methoxy)phenyl)cyclopropyl)benzoic acid;
4-(2-(2-chloro-4-((5-cyclopropyl-3-(2,6-dichlorophenyl)isoxazol-4-yl)methoxy)phenyl)cyclopropyl)benzoic acid;
5-(2-(2-chloro-4-((5-cyclopropyl-3-(2,6-dichlorophenyl)isoxazol-4-yl)methoxy)phenyl)cyclopropyl)-1-isopropyl-1H-pyrazole-3-carboxylic acid;
6-(2-(2-chloro-4-((5-cyclopropyl-3-(2,6-dichlorophenyl)isoxazol-4-yl)methoxy)phenyl)cyclopropyl)-1-methyl-1H-indazole-3-carboxylic acid;
6-(2-(2-chloro-4-((5-cyclopropyl-3-(2,6-dichlorophenyl)isoxazol-4-yl)methoxy)phenyl)cyclopropyl)-1-isopropyl-1H-indazole-3-carboxylic acid;
3-(3-(2-chloro-4-((5-cyclopropyl-3-(2,6-dichlorophenyl)isoxazol-4-yl)methoxy)phenyl)-3-hydroxycyclobutyl)benzoic acid;
5-(3-(2-chloro-4-((5-cyclopropyl-3-(2,6-dichlorophenyl)isoxazol-4-yl)methoxy)phenyl)-3-hydroxycyclobutyl)-1-isopropyl-1H-pyrazole-3-carboxylic acid;
6-(3-(2-chloro-4-((5-cyclopropyl-3-(2,6-dichlorophenyl)isoxazol-4-yl)methoxy)phenyl)-3-hydroxycyclobutyl)-1-methyl-1H-indazole-3-carboxylic acid;
4-(3-(2-chloro-4-((5-cyclopropyl-3-(2,6-dichlorophenyl)isoxazol-4-yl)methoxy)phenyl)-3-hydroxycyclobutyl)benzoic acid;
3-(3-(2-chloro-4-((5-cyclopropyl-3-(2,6-dichlorophenyl)isoxazol-4-yl)methoxy)phenyl)-3-hydroxyazetidin-1-yl)benzoic acid; and
5-(3-(2-chloro-4-((5-cyclopropyl-3-(2,6-dichlorophenyl)isoxazol-4-yl)methoxy)phenyl)-3-hydroxyazetidin-1-yl)nicotinic acid.

Additional FXR agonists useful in the present inventions can be identified routinely by those of skill in the art based upon assays such as described in PCT/US99/30947, the teachings of which are herein incorporated by reference in their entirety. Typically, FXR agonists are identified using a nuclear receptor-peptide assay. This assay utilizes fluorescence resonance energy transfer (FRET) and can be used to test whether putative ligands bind to FXR. The FRET assay is based upon the principle that ligands induce conformational changes in nuclear receptors that facilitate interactions with coactivator proteins required for transcriptional activation. In FRET, a fluorescent donor molecule transfers energy via a non-radioactive dipole-dipole interaction to an acceptor molecule (which is usually a fluorescent molecule).

Typically the FXR agonist of the invention is administered to the subject with a therapeutically effective amount. By a "therapeutically effective amount" of the FXR agonist as above described is meant a sufficient amount of the FXR agonist to treat a hepatitis B virus infection at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination with the specific agonist employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

Any of the above treatment regimens can be administered to individuals who have been diagnosed with an HBV infection. Any of the above treatment regimens can be administered to individuals who have failed previous treatment for HBV infection (treatment failure patients). "Treatment failure patients" as used herein generally refers to HBV-infected patients who failed to respond to previous therapy for HBV (referred to as "non-responders") or who initially responded to previous therapy, but in whom the therapeutic response was not maintained (referred to as "relapsers"). The previous and currently available therapy generally can include treatment with antiviral drugs such as lamivudine (Epivir), adefovir (Hepsera), tenofovir (Viread), telbivudine (Tyzeka) and entecavir (Baraclude), and the three listed immune system modulators interferon alpha-2a, PEGylated interferon alpha-2a (Pegasys) and interferon alpha-2b (ViraferonPeg or INTRON A).

In particular the FXR agonist according to the invention may be administered to the subject in combination with currently available therapy, including treatment with antiviral drugs such as the reverse transcriptase inhibitors, lamivudine (Epivir), adefovir (Hepsera), tenofovir (Viread), telbivudine (Tyzeka) and entecavir (Baraclude), and the immune system modulators interferon alpha-2a, PEGylated interferon alpha-2a (Pegasys) or interferon alpha-2b (ViraferonPeg or INTRON A).

The FXR agonist of the invention may be combined with pharmaceutically acceptable excipients, and optionally sustained-release matrices, such as biodegradable polymers, to form pharmaceutical compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

In particular, the pharmaceutical compositions contain vehicles which are pharmaceutically acceptable for a formulation capable of being injected. These may be, in particular, isotonic, sterile, saline solutions (monosodium or disodium phosphate, sodium, potassium, calcium or magnesium chloride and the like or mixtures of such salts), or dry, especially freeze-dried, compositions which, upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free bases or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The FXR agonist of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with various proportions of the other ingredients enumerated above, as required, followed by filtered sterilization. Generally, dispersions are prepared by incorporating the various sterilized active ingredients into a sterile vehicle which contains the basic dispersion medium and the other required ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

The FXR agonist of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds of the invention formulated for parenteral administration, such as intravenous or intramuscular injection, other pharmaceutically acceptable forms include, e.g., tablets or other solids for oral administration; liposomal formulations; time-release capsules; and any other form currently used.

The invention will be further illustrated by the following figures and examples. However, these examples and figures should not be interpreted in any way as limiting the scope of the present invention.

Differentiated HepaRG cells were infected with HBV (100 geq/cell for 24 hr), then treated 3 successive times (days 4, 7 and 11 post infection) with FXR modulators at indicated concentrations in μM. Cell supernatants were collected 14 days post infection for quantification of HBsAg (Architec Abbott).

Figure 2A:
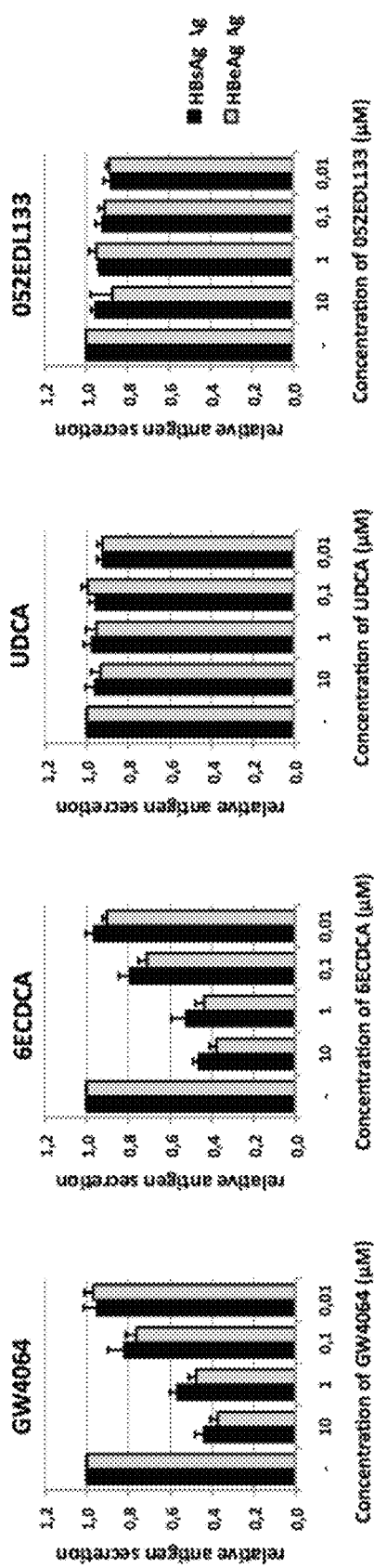
Figure 2B:
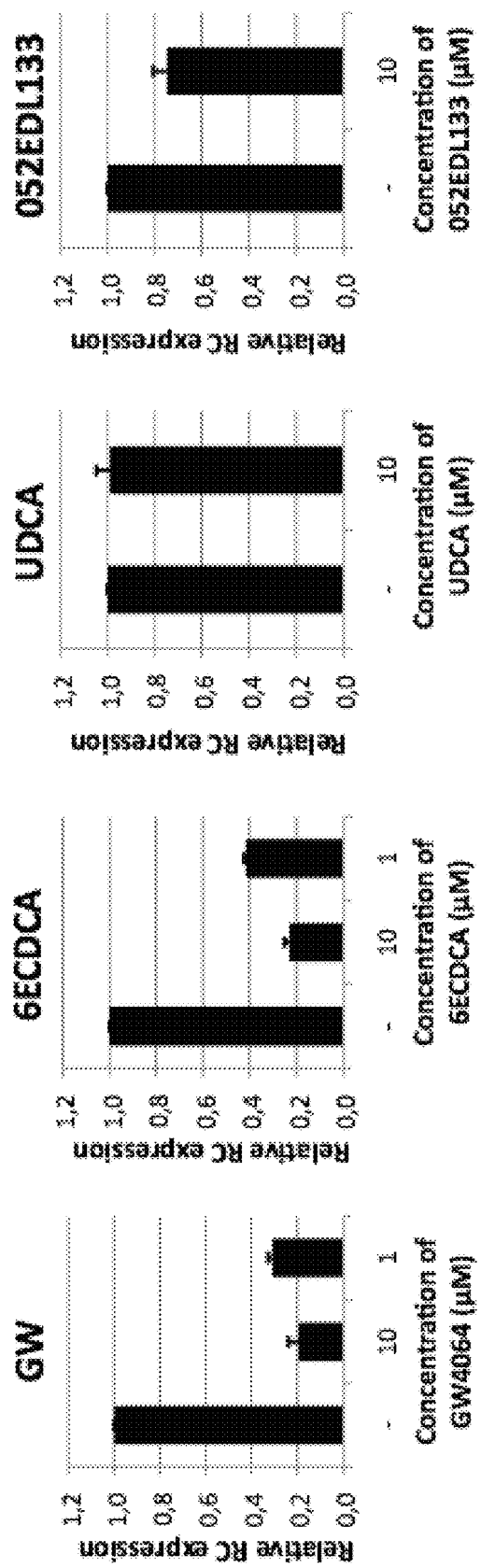
Figure 2C:
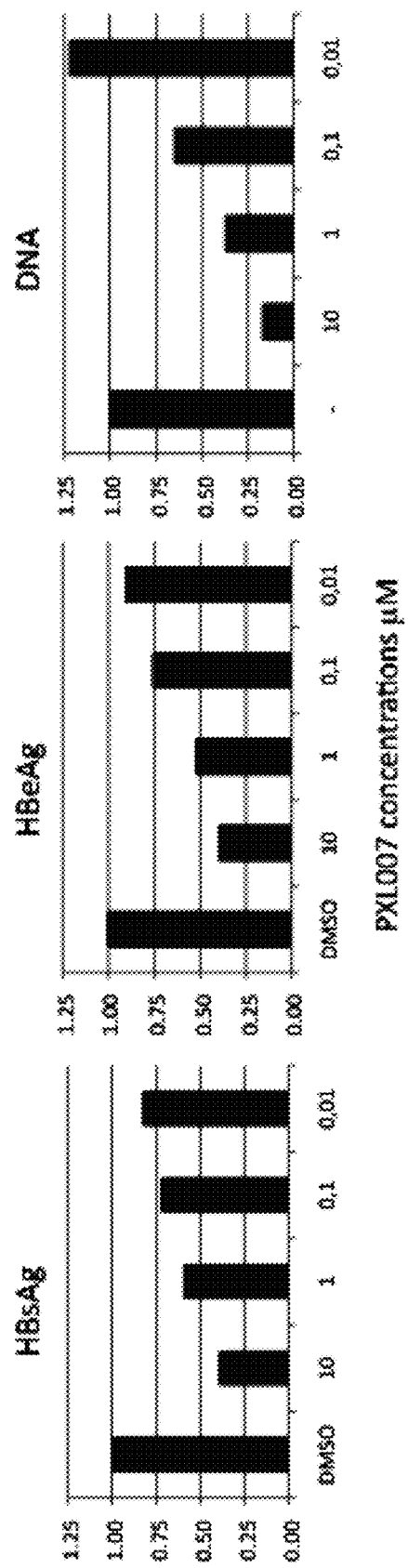

FIGS. 2A-2C—Secretion of HBV surface (HBsAg), core (HBeAg) antigens and HBV DNA in supernatant of HBV infected HepaRG.

Differentiated HepaRG cells were infected with HBV (100 geq/cell for 24 hr), then treated 3 successive times (days 4, 7 and 11 post infection) with FXR agonists and antagonists or FXR inactive bile acid UDCA at indicated concentrations (μM). Cell supernatants were collected 14 days post infection for quantification of HBsAg, HBeAg (Architec Abbott) or HBV DNA by quantitative PCR using rcDNA primers (n=3±SEM). FIG. 2A—Both FXR agonists, GW4064 and 6ECDCA, inhibit the secretion of HBsAg and HBeAg in the supernatant in a dose-dependent manner whereas UDCA and 052EDL133 have no effect on the antigen secretion. FIG. 2B—Both FXR agonists, GW4064 and 6ECDCA, inhibit the secretion of infectious HBV DNA positive viral particles in the supernatant in a dose-dependent manner. UDCA and 052EDL133 have no or limited effect on the virion secretion. FIG. 2C—The FXR agonist PXL007 represses HBsAg, HBeAg and HBV DNA in a dose-dependent manner.

Figure 3:
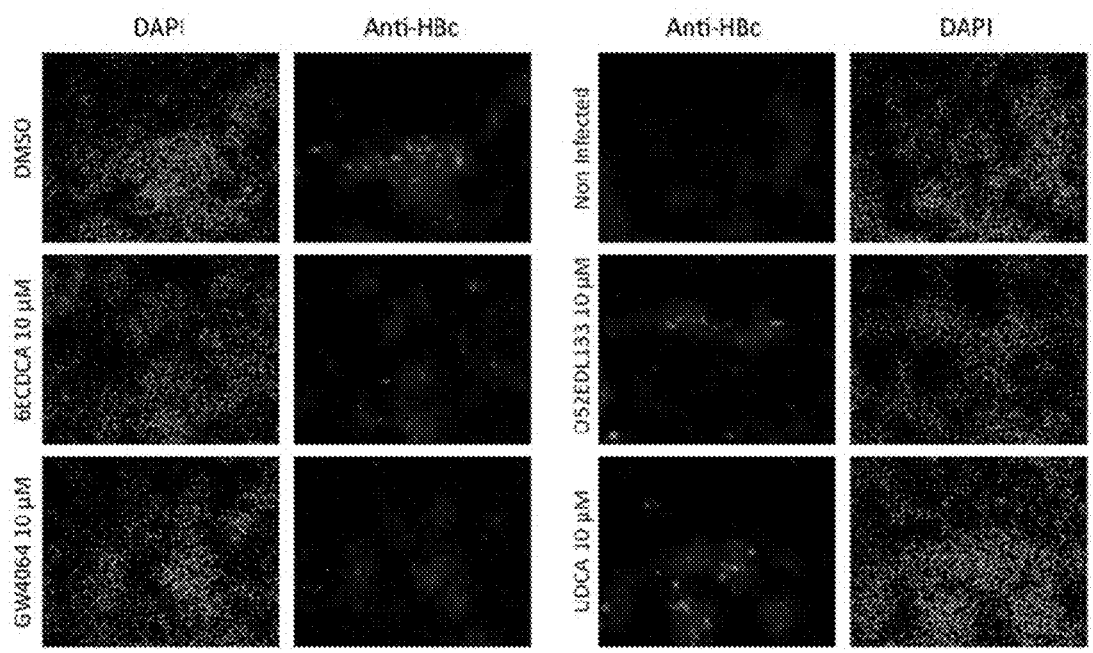

FIG. 3—Expression of HBV core protein (HBc) within HepaRG cells in presence or not of FXR agonists.

Figure 1:
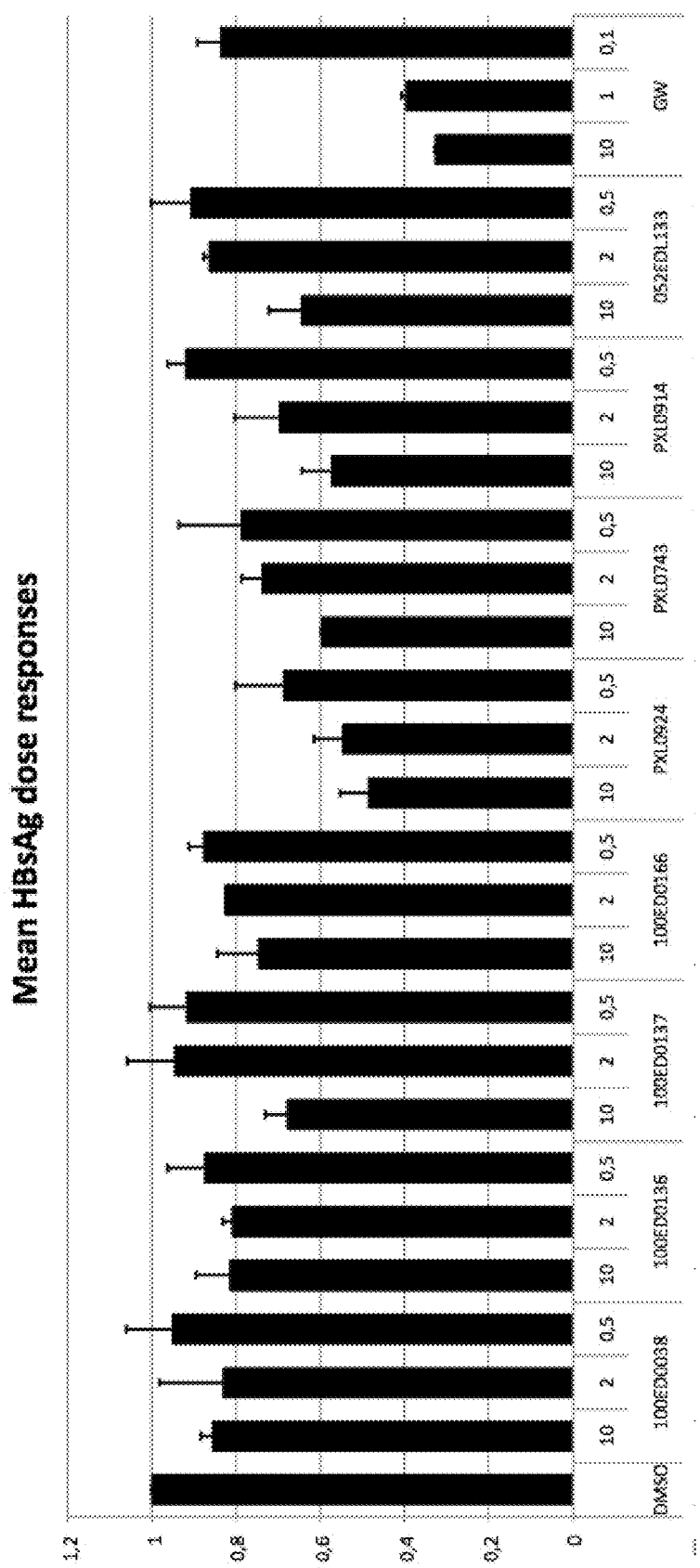
FIG. 1—Secretion of surface HBs antigen (HBsAg) in the supernatant of HBV infected HepaRG cell line in presence of FXR modulators.

Differentiated HepaRG cells grown on coverslips were infected and treated as described in FIG. 1 legend (n=3±SEM). Cells were fixed on day 14 post infection and immunocytochemistry using anti-HBc antibody was carried out. Fluorescent microscopy reveals that FXR agonists, GW4064 and 6ECDCA, drastically reduce the expression of HBc in the infected cells. UDCA and 052EDL133 do not appear to modify the expression of HBc.

Figure 4B:
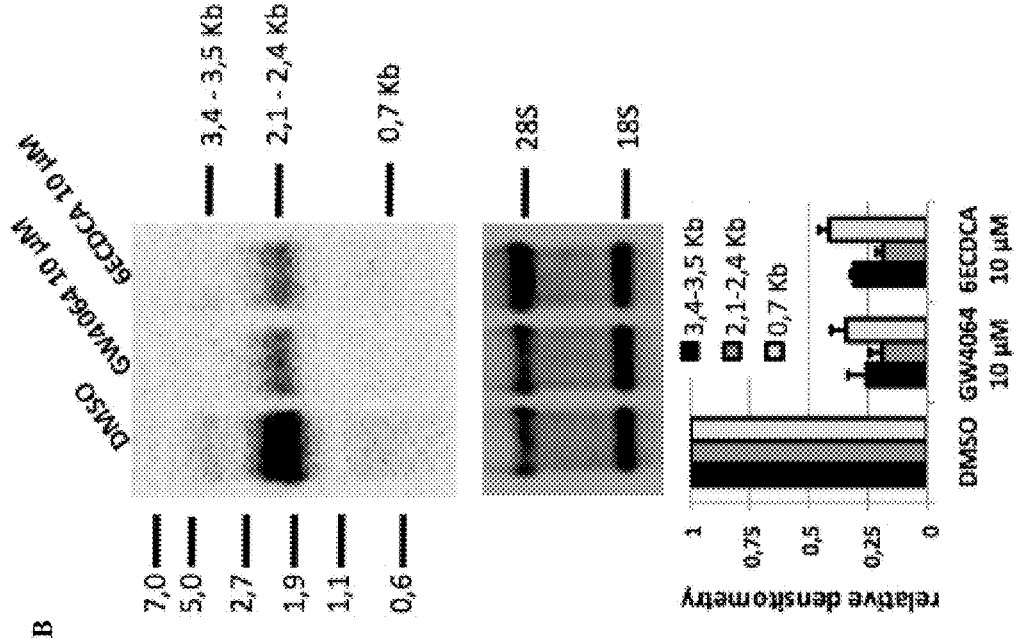
Figure 4A:
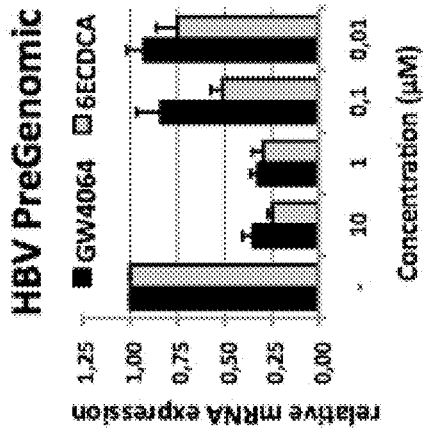
Figure 4C:
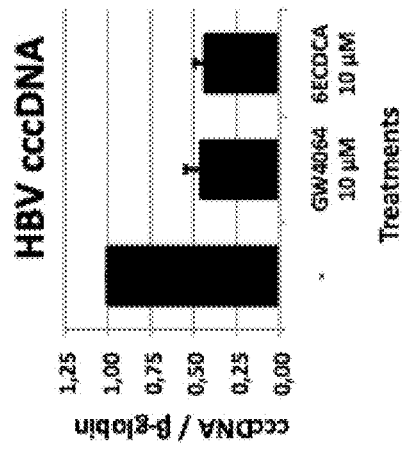

FIGS. 4A-4C—HBV Pregenomic/precore mRNA and cccDNA expression in HBV infected HepaRG cell line in presence or not of FXR agonists.

Differentiated HepaRG cells were infected and treated as described in FIG. 1 legend. Cells were lysed and RNA was extracted, then either reverse transcribed into cDNA for quantitative PCR (qRT-PCR) (FIG. 4A) or used in Northern Blot experiment (FIG. 4B). The same experiment was repeated and DNA was extracted. Following plasmid-safe DNase treatment, cccDNA expression was quantified by qPCR experiment using specific HBV cccDNA primers and TaqMan probe (n=3±SEM) (FIG. 4C). cccDNA quantification was normalized to the number of βglobin gene. The expression levels of HBV pregenomic gene were quantified, as well as 3 housekeeping genes for normalization (n=3±SEM). Both FXR agonists, GW4064 and 6ECDCA, inhibit the expression of HBV pregenomic/precore mRNA in a dose-dependent manner. The reduction is confirmed in the northern blot (3.4-3.5 Kb band). The expression of the other HBV mRNAs (S: 2.1-2.4 Kb; X: 0.7 Kb) is also reduced, as seen on the densitometry graph (n=3±SEM). cccDNA levels were also reduced by more than 50% following treatment with FXR agonists.

Figures 5A, 5B:
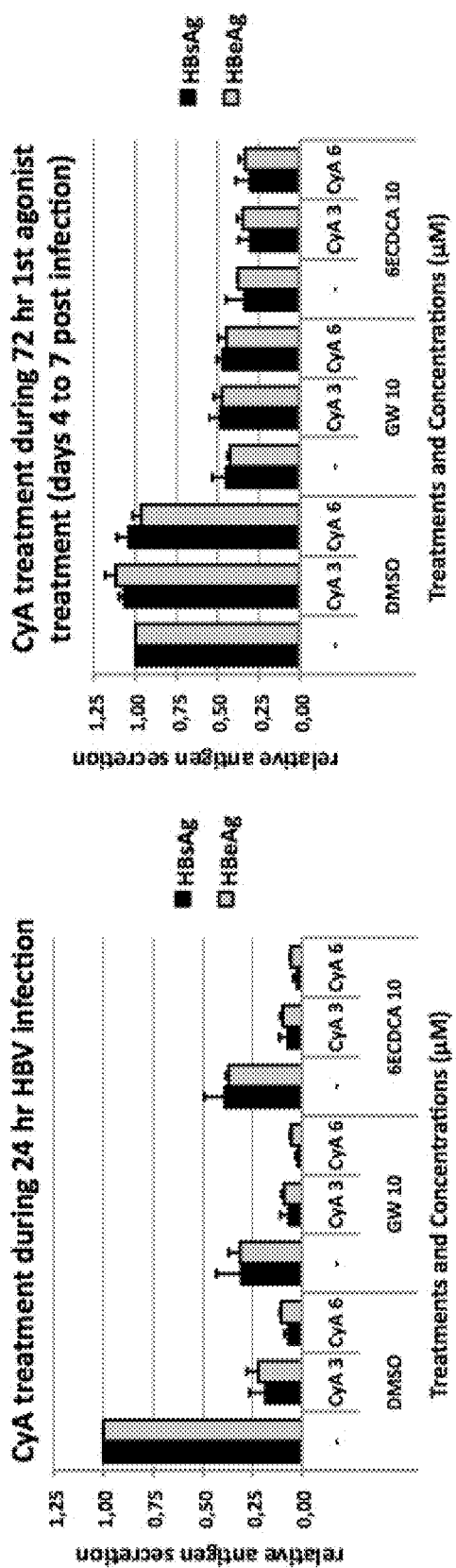

FIGS. 5A-5B—Effect of the HBV entry inhibitor Cyclosporin A on FXR agonists modulation of HBsAg and HBeAg secretion in the supernatant of HBV infected HepaRG cells.

Differentiated HepaRG cells were infected and treated as described in FIG. 1 legend. In addition to the usual protocol previously described, cells were treated with cyclosporin A (CyA) either during HBV infection (i.e. for 24 hr) or during the $1^{st}$ treatment with FXRα agonists (i.e. for 72 hr; from day 4 to 7 post infection). Cell supernatants were collected 14 days post infection for quantification of HBsAg and HBeAg (n=3±SEM). FIG. 5A) CyA treatment during HBV infection inhibits viral entry in a dose-dependent manner and does not impair the decrease in HBsAg and HBeAg secretions following treatment with FXR agonists. FIG. 5B) CyA treatment post infection has no effect on HBV antigen secretion whatever the presence or not of FXR agonists.

Figure 6:
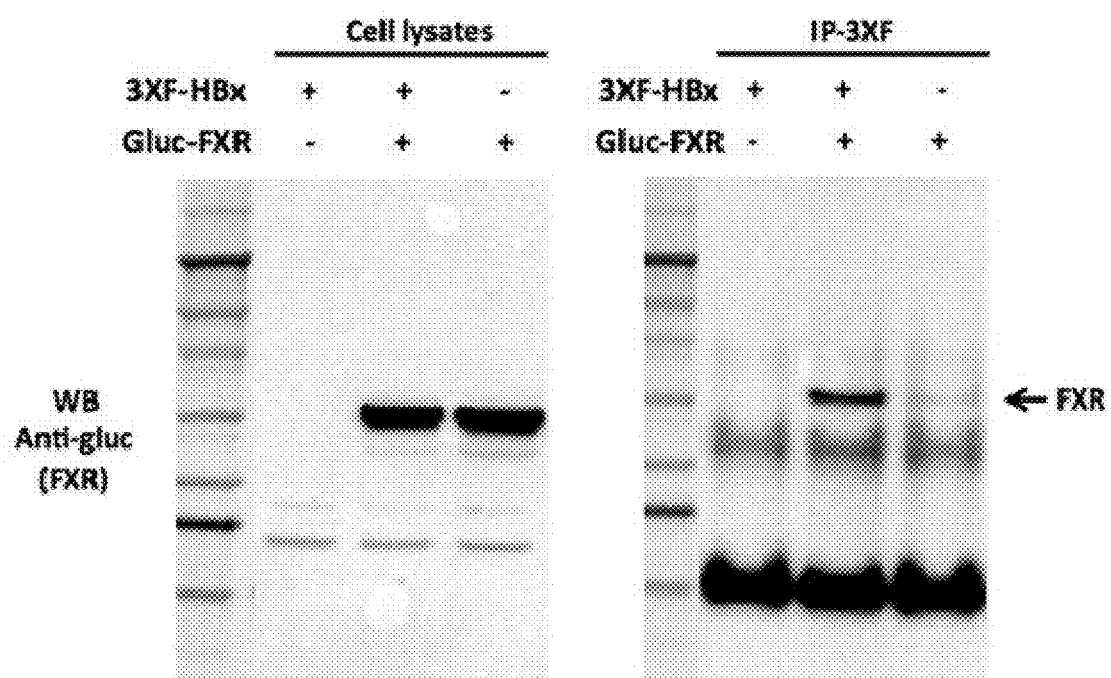

FIG. 6—Co-Immunoprecipitation assay of FXR and HBx proteins

HEK293T cells were co-transfected with fusion proteins 3XF-HBx and Gluc-FXR encoding plasmids. 48 h post-transfection, cells were lysed and co-immunoprecipitation was performed with Dynabeads®Protein G beforehand coupled with anti-3XF antibody. Cells lysates and co-immunoprecipitation products were analyzed by western blot; FXR expression was detected with anti-Gluc antibody. FXR expression in control, Gluc-FXR alone, or in the test cells, co-expression of Gluc-FXR and 3XF-HBx, was similar as shown on the left western blot. After immunoprecipitation with anti-3XF antibody, FXR fusion protein was evidently detected in the test condition and not in the control (right western blot). These observations strongly suggest an interaction between the viral HBx protein and the nuclear receptor FXR.

Figure 7:
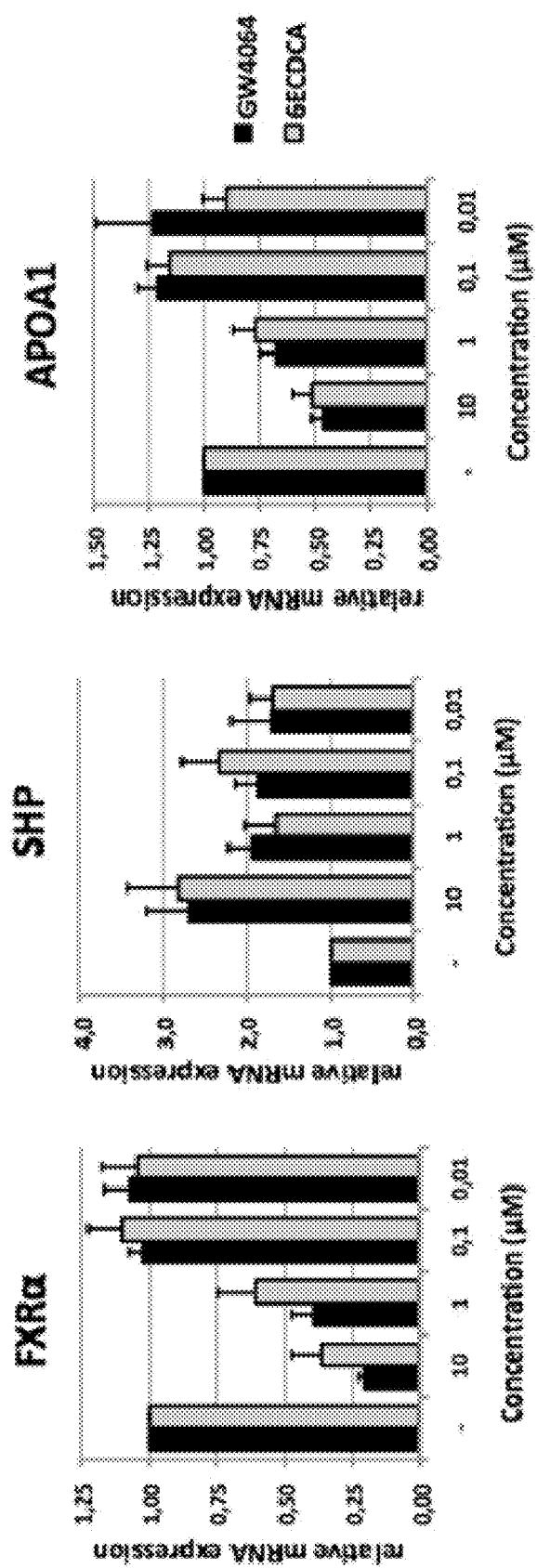

FIG. 7—mRNA expression of FXR and two of its regulated genes

Differentiated HepaRG cells were infected and treated as described in FIG. 1 legend. Cells were lysed and RNA was extracted, then reverse transcribed into cDNA for qPCR. The expression levels of 3 genes of interest were quantified: FXRα, SHP and APOA1, as well as 3 housekeeping genes for normalization (n=3±SEM). FXR agonists, GW4064 and 6ECDCA, inhibit the expression of FXR mRNA in a dose-dependent manner. SHP and APOA1 are two genes under the regulation of FXR; SHP is induced by FXR while APOA1 is repressed. Here, SHP mRNA expression increases with GW4064 and 6ECDCA treatments, while APOA1 mRNA expression decreases. This suggests an activation of FXR despite its reduced expression.

Figures 8A, 8B:
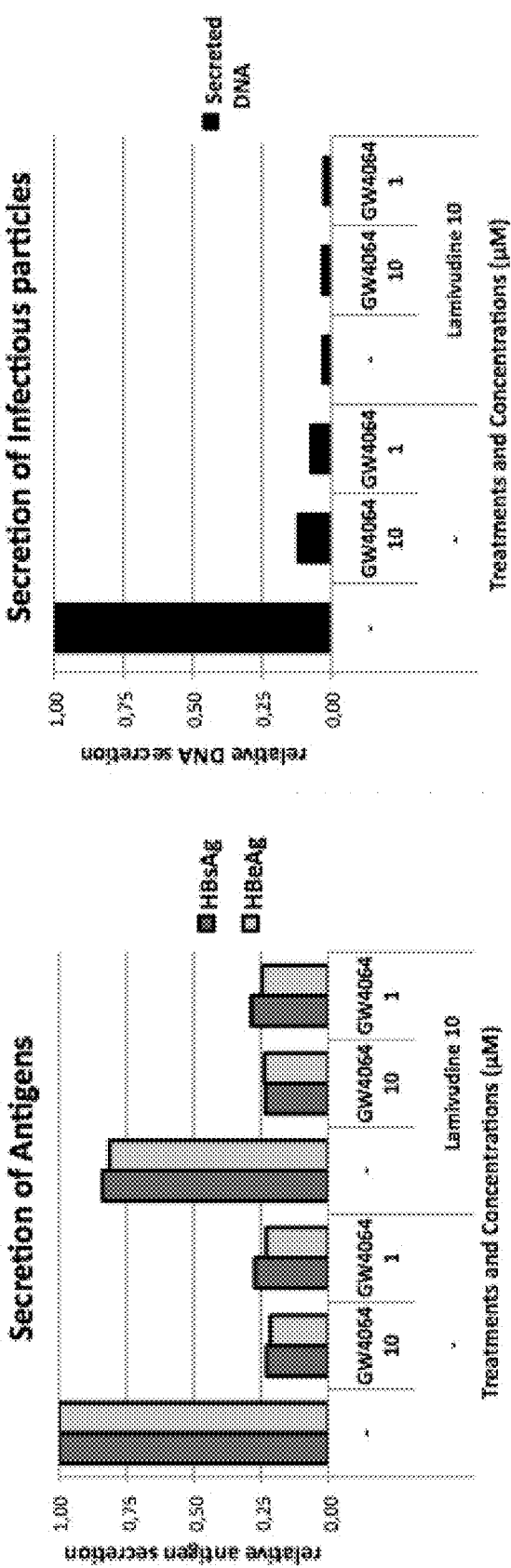

FIGS. 8A-8B—Co-treatment of FXR agonist with lamivudine, a potent nucleoside analog reverse transcriptase inhibitor Differentiated HepaRG cells were infected and treated as described in FIG. 1 legend. Cell supernatants were collected 14 days post infection. (FIG. 8A) Quantification of HBsAg and HBeAg secretion. (FIG. 8B) Quantification of secreted infectious particles by DNA extraction and quantification by qPCR. Treatment with lamivudine at 10 µM has very limited effect on the secretion of HBV antigens whereas its effect on HBV DNA secretion is nearly complete with 97% reduction of HBV DNA in the cell supernatant.

EXAMPLE

Methods

The HepaRG line derived from a human cellularhepato carcinoma can differentiate and regain many phenotypic traits of hepatocytes after 4 weeks of culture under defined conditions (Hantz O. et al., 2009, J Gen Virol; 90:127-135). After differentiation, these cells are susceptible to infection at high MOI of HBV virions produced by HepG2.2.15 line. Under these conditions viral production can be observed in the second week post infection. This system allows the study of most steps of the viral replication cycle, including penetration into the cell, translocation of the viral genome into the nucleus, the repair and synthesis of the cccDNA, transcription of pregenomic and viral mRNAs as well as later stages of the replication cycle with the synthesis of viral proteins, the assembly and secretion of infectious virions and the secretion of the viral proteins HBs and HBe.

The HepaRG system thus allows the monitoring of the secretion of HBsAg and HBeAg and virion incorporated DNA into the cell culture supernatant after infection with HBV infectious virion stocks prepared from the HepG2.2.15 cell line. This system also allows the monitoring of the synthesis of pregenomic and viral mRNAs as well as cytoplasmic replication intermediates and cccDNA. The effects of molecules on cell physiology and cell differentiated functions were explored, including the quantification of hepatic markers such as albumin and apolipoprotein B. The effects of the compounds on the cellular bile acid pathway were monitored by analysis and quantification of the FXR mRNA as well as the SHP and apoA1 encoding mRNAs the expression of which is under the control of FXR Results FXR Agonists are Potent HBV Replication Inhibitors A panel of molecules not previously described and original or reference modulators of FXR activity were first tested on the expression of a reporter gene under the control of the HBV Enh2/core promoter region that contains two FXR response elements in the Huh-7 cell line as described in Ramière C, et al., 2008, J Virol; 82: 10832-10840. Molecules were then classified as FXR agonists or antagonists on the basis respectively of the expression increase or decrease of the reporter gene under the transcription control of FXR. Some molecules had an intermediate profile, being a moderate agonist when tested separately and a weak antagonist when tested in competition against a reference agonist (data not shown). The most potent and representative compounds were first evaluated for their effect on the synthesis and secretion of HBsAg in the culture supernatant of HepaRG cell culture system naturally infected with HBV produced in HepG2.2.15 (FIG. 1). Unexpectedly, the most potent antagonists (i.e. 100ED0038, 100ED0136, 100ED0137, and 100ED0166) as well as the reference antagonist 052EDL133 (described in WO 2007/052843, Takeda Pharmaceutical Co. Ltd., Osaka, Japan), had little or no effect on HBsAg secretion. Surprisingly, the agonist GW4064 such as disclosed in PCT Publication No. WO 00/37077 or in US2007/0015796, had a strong and dose dependent inhibitory effect on HBsAg secretion (around 70% inhibition at 10 µM. Partial agonists such as PXL0914 (4-Bromo-5-[4-(2-chloro-benzenesulfonyl)-[1,4]diazepan-1-yl]-benzofuran-2-carboxylic acid from WO 2009/127321), PXL0924 (5-[4-(2,6-Dichloro-benzoyl)-piperazin-1-yl]-4-methyl-benzofuran-2-carboxylic acid, from WO 2009/127321) and PXL0743 (4-Bromo-5-[4-(2,6-dichloro-benzenesulfonylamino)-piperidin-1-yl]-benzofuran-2-carboxylic acid, from WO 2009/127321) had an intermediate profile of inhibition. Thus some molecules decreased the production of HBsAg in a dose-dependent manner. If the active molecules are classified by their antagonist, agonist or agonist "partial" by the screening test in Huh-7 cell with the reporter gene construct, it appears, against previous odds, that the inhibitory effect on the production of HBsAg grew with the tendency of the molecule to be a potent FXR agonist.

To confirm this finding, we next tested several molecules, the reference FXR antagonist 052EDL133 (see above), two well characterized FXR agonists which belong to different chemical classes, GW4064 (see above) and 6ECDCA (a biliary salt derivative and potent FXR agonist, currently in clinical trial for primary biliary cirrhosis and insulin resistance; see above) and the biliary salt analogue ursodesoxycholic acid, which is not an FXR ligand (Parks D J1, et al., Science, 1999 May 21; 284(5418):1365-8; Makishima M. et al., Science, 1999 May 21; 284(5418):1362-5). FIG. 2A shows that only GW4064 and 6ECDCA had a dose dependent and strong inhibitory effect on the secretion of HBsAg and HBeAg in HepaRG supernatant of infected cells after 10 days of treatment. The bile salt ursodeoxycholate did not inhibit the secretion of the viral protein at any doses and the FXR antagonist 052EDL133 had little or no effect. Similar findings were observed when testing the effect of these molecules on the secretion of the viral DNA in the supernatant (FIG. 2B). Strong inhibition, up to 80%, was observed with the two agonists, while UDCA did not modify the secretion of the viral DNA. It should be noted, however, that the antagonist 052EDL133 moderately reduced the amount of viral DNA secreted at 10 µM (close to 20% inhibition). Finally, the activity on viral replication of a chemically different FXR agonist, PXL007, identified by CAS Registry Number 1192171-69-9 (described in WO2009/127321), was tested in the same assay. This FXR agonist also strongly inhibited viral protein and DNA secretion (FIG. 2C).

We further explored the effect of GW4064 and 6ECDCA on the cellular expression of the viral core protein HBc by immunofluorescence (FIG. 3). Again, both FXR agonists strongly inhibited HBc expression in infected cells, whereas UDCA and 052EDL133 did not significantly modify HBc synthesis.

Finally we quantified the amount of viral RNA by quantitative RT-PCR and Northern blotting in infected cells treated or not by GW4064 and 6ECDCA as well as the variations of the cccDNA reservoir (FIG. 4). The presence of the two 3.4 and 3.5 pre-core and pre-genomic RNAs was reduced in a dose-dependent manner by FXR agonists up to 75% (panel A) as measured by quantitative RT-PCR. The presence of the three classes of viral mRNA, i.e., the 3.4 and 3.5 pre-core and pre-genomic mRNAs, the 2.1-2.4 S mRNA and the 0.7×mRNA, was reduced to similar extent at 10 µM measured by Northern blotting (panel B). Interestingly, the cccDNA reservoir was also reduced by more than 50% after treatment with the two agonists at 10 µM (panel C).

Mechanism of Action

The sodium taurocholate cotransporter peptide (NTCP) was recently identified as a receptor for HBsAg at the baso-lateral plasma membrane of hepatocytes. NTCP expression is mandatory for virus entry into hepatocytes. Sodium taurocholate cotransporting polypeptide is a functional receptor for human hepatitis B and D virus (Yan H. et al. Elife (Cambridge). 2012 Nov. 13; 1:e00049. doi: 10.7554/eLife.00049). HBV and bile acids share common binding site on NTCP and compete for the receptor (Yan H. et al., J Virol., 2014 March; 88(6):3273-84. doi: 10.1128/JVI.03478-13, Epub 2014 Jan. 3). As FXR agonists are molecules that are directly derived from bile acids or share some molecular determinants with bile acids, FXR agonists might just inhibit the virus entry through competition for the receptor. We thus tested the effect of addition to FXR agonists of cyclosporin A (CsA), a molecule which inhibits NTCP mediated bile acid uptake and binds NTCP at a site identical to or overlapping with the pre-S1 peptide binding site (Nkongolo S, et al., J Hepatol., 2014 April; 60(4):723-31, doi: 10.1016/j.jhep.2013.11.022, Epub 2013 Dec. 1). When increasing concentrations of CsA were introduced into the culture medium during infection, we observed a dose dependent competition with HBV entry with an inhibition of HBsAg and HBeAg secretion as expected. Treatment with GW4064 or 6ECDCA further reduced the secretion of the viral proteins (FIG. 5A). On the opposite, addition of CsA after the infection period had no effect on HBV replication with a conserved HBsAg and HBeAg secretion nor did it modify the effect of FXR agonists (FIG. 5B). Taking into account, as previously reported, that there is little or no viral spread during the culture in this system, we conclude that antiviral activity of FXR agonists is not related to a direct inhibition of NTCP but rather modulates later steps of the infection cycle.

We next investigated whether viral proteins could interfere with FXR by co-immunoprecipitation using tagged viral proteins and FXR. We found that HBx viral protein and FXR could be immunoprecipitated by antibody directed against one or the other protein (FIG. 6). This data suggested an interaction between HBx and FXR, strengthening the hypothesis that the virus tightly regulates FXR activity.

Next we investigated the effect of FXR agonists on the expression level of mRNA encoding FXR itself as well as SHP and ApoA1, two genes the expression of which is respectively under the positive and negative control of FXR. We found that 10 days treatment with FXR agonists GW4064 and 6ECDCA increased the expression of SHP mRNA and decreased that of ApoA1 mRNA indicating that indeed FXR agonists boosted FXR activity (FIG. 7). Interestingly, FXR mRNA expression was also strongly repressed by both agonists likely as a result of the SHP dependent negative control loop on FXR expression. Thus treatment with FXR agonists significantly and durably modifies bile acid metabolism with an increased FXR activity along with a decreased FXR expression.

Effect of Combined Treatment with FXR Agonist and Reverse Transcriptase Inhibitor on HBV Replication FXR agonists thus appear to repress HBV replication at steps that occur after viral entry and mainly on cccDNA reservoir stability and expression, thus before the reverse transcription step. We thus tested the effect of combination treatment of HBV infected HepaRG cells on viral replication (FIG. 8). We observed that treatment with the nucleoside analogue reverse transcriptase inhibitor lamivudine even at high concentration (10 µM with an IC50 at 6 nM, Lada O, et al., Antivir Ther., 2004 June; 9(3):353-63) only weakly repressed the secretion of HBsAg and HBeAg but very efficiently decreased HBV DNA positive virions secretion as expected. Addition of FXR agonist did not seem, in this condition, to further decrease the secretion of viral DNA but potently repressed the synthesis and secretion of viral proteins.

Discussion

We showed that FXR is an essential host factor in the development of HBV in hepatocytes and that, unexpectedly, FXR agonists are more potent inhibitors than the antagonists on HBV replication in HepaRG cell lines. This antiviral activity was demonstrated with very structurally diverse and selective FXR agonists: GW4064, PXL007 (molecule having the CAS Registry Number 1192171-69-9), the bile acid derivative 6ECDCA and others. This reduces the probability of an "off-target" effect. FXR agonists seem to primarily act on viral mRNA transcription and expression from the viral minichromosome and on cccDNA stability. Overall FXR agonists, besides reducing viral DNA replication and the production of infectious virions, an effect that can be efficiently and safely obtained with reverse transcriptase polymerase inhibitors, have the unique capacity to decrease the synthesis and secretion of the viral proteins and to reduce the cccDNA reservoir size. These two late effects are not obtained by polymerase inhibitors and can only be reached for a low percentage of patients treated with interferons. Reducing the viral protein secretion and cccDNA reservoir are two majors goals to cure HBV infection, since, on the one hand, viral proteins have been shown to dampen the innate immune response, mainly through interaction with TLR, and maintain an immune-tolerant status against the virus and, on the other hand, viral persistence and latency depend on the continuous presence of cccDNA.

Persistence of HBV replication also requires the presence of a supportive cellular environment providing, in particular, an active transcriptional cellular machinery for the expression of the viral genes. Regulation of FXR activity by the virus may be part of the viral strategy to control its own replication. Indeed, the competition between HBV virions and bile acids for NTCP decreases the intracellular bile acid pool, with the subsequent consequences of a decreased FXR activity and an increased level of FXR expression (Oehler N, et al., Hepatology, 2014 Apr. 8, doi: 10.1002/hep.27159, [Epub ahead of print]). Treatment with FXR agonists proved to reverse the bile acid metabolism modification induced by the virus, which thus appears as a beneficial condition for supporting viral replication.

The discovery of the antiviral effect of 6ECDCA, a molecule in clinical development in two separate indications (i.e. primary biliary cirrhosis and insulin resistance), with good tolerance during long-term treatment, offers the opportunity for "repositioning" the molecule in the treatment of HBV infection. In conclusion, we have identified new molecules (i.e. FXR agonists) that regulate (reduce) HBV infection. This should allow the selection of candidates who could be tested in a mouse model or directly in humans with FXR agonists already in clinical trials.

REFERENCES

Throughout this application, various references describe the state of the art to which this invention pertains. The disclosures of these references are hereby incorporated by reference into the present disclosure.

The invention claimed is:

1. A method for treating a chronic hepatitis B virus infection in a subject in need thereof, comprising administering to the subject a therapeutically effective amount of a farnesoid X receptor (FXR) agonist.

2. The method of claim 1, wherein the subject is infected with a hepatitis B virus genotype selected from genotype A, B, C, and D.

3. The method of claim 1, wherein the farnesoid X receptor (FXR) agonist is a selective FXR agonist.

4. The method of claim 1, wherein the farnesoid X receptor (FXR) agonist is selected from the group consisting of the compounds identified by the CAS REGISTRY NUMBERS 1192171-69-9, 6ECDCA, GW4064, PXL0914, and PXL0743.

5. The method of claim 1, wherein the farnesoid X receptor (FXR) agonist is selected from the group consisting of the compounds identified by the CAS REGISTRY NUMBERS 1192171-69-9 and 6ECDCA.

6. The method of claim 1, wherein the subject has failed to respond to a previous treatment for HBV infection.

7. The method of claim 6, wherein the previous treatment is selected from the group consisting of lamivudine (Epivir), adefovir (Hepsera), tenofovir (Viread), telbivudine (Tyzeka), entecavir (Baraclude), interferon alpha-2a, PEGylated interferon alpha-2a (Pegasys) and interferon alpha-2b (ViraferonPeg or Introna).

8. The method of claim 1, wherein the FXR agonist is administered in combination with a treatment selected from the group consisting of lamivudine (Epivir), adefovir (Hepsera), tenofovir (Viread), telbivudine (Tyzeka), entecavir (Baraclude), interferon alpha-2a, PEGylated interferon alpha-2a (Pegasys) and interferon alpha-2b (ViraferonPeg or Introna).

9. A method for reducing synthesis and/or secretion of HBsAg and/or HBeAG or for reducing serum HBV DNA in a subject in need thereof, comprising administering to the subject a therapeutically effective amount of a farnesoid X receptor (FXR) agonist.

10. The method of claim 9, wherein the subject is infected with a hepatitis B virus genotype selected from genotype A, B, C, and D.

11. The method of claim 9, wherein the farnesoid X receptor (FXR) agonist is a selective FXR agonist.

12. The method of claim 9, wherein the farnesoid X receptor (FXR) agonist is selected from the group consisting of the compounds identified by the CAS REGISTRY NUMBERS 1192171-69-9, 6ECDCA, GW4064, PXL0914, and PXL0743.

13. The method of claim 9, wherein the farnesoid X receptor (FXR) agonist is selected from the group consisting of the compounds identified by the CAS REGISTRY NUMBERS 1192171-69-9 and 6ECDCA.

14. The method of claim 9, wherein the subject has failed to respond to a previous treatment for HBV infection.

15. The method of claim 14, wherein the previous treatment is selected from the group consisting of lamivudine (Epivir), adefovir (Hepsera), tenofovir (Viread), telbivudine (Tyzeka), entecavir (Baraclude), interferon alpha-2a, PEGylated interferon alpha-2a (Pegasys) and interferon alpha-2b (ViraferonPeg or Introna).

16. The method of claim 9, wherein the FXR agonist is administered in combination with a treatment selected from the group consisting of lamivudine (Epivir), adefovir (Hepsera), tenofovir (Viread), telbivudine (Tyzeka), entecavir (Baraclude), interferon alpha-2a, PEGylated interferon alpha-2a (Pegasys) and interferon alpha-2b (ViraferonPeg or Introna).

* * * * *